US007638334B2

(12) United States Patent
Nicolaides et al.

(10) Patent No.: US 7,638,334 B2
(45) Date of Patent: Dec. 29, 2009

(54) METHOD FOR GENERATING ENGINEERED CELLS BY HOMOLOGOUSLY RECOMBINING SEGMENTS HAVING INCREASED DEGENERACY

(75) Inventors: Nicholas C. Nicolaides, Boothwyn, PA (US); J. Bradford Kline, Norristown, PA (US); Luigi Grasso, Bala Cynwyd, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 0 days.

(21) Appl. No.: 10/348,074

(22) Filed: Jan. 17, 2003

(65) Prior Publication Data

US 2003/0176386 A1 Sep. 18, 2003

Related U.S. Application Data

(60) Provisional application No. 60/349,565, filed on Jan. 18, 2002.

(51) Int. Cl.
| | |
|---|---|
| C12N 15/87 | (2006.01) |
| C12N 1/12 | (2006.01) |
| C12N 15/74 | (2006.01) |
| A01N 63/00 | (2006.01) |
| A01N 65/00 | (2006.01) |
| A01N 63/04 | (2006.01) |
| A61K 48/00 | (2006.01) |
| C12Q 1/68 | (2006.01) |
| A01N 43/04 | (2006.01) |
| A61K 31/70 | (2006.01) |

(52) U.S. Cl. ............... 435/463; 424/93.1; 424/93.21; 514/44; 435/6; 435/252.1; 435/471

(58) Field of Classification Search .......... 514/44; 424/93.1; 536/23.1, 23.5
See application file for complete search history.

(56) References Cited

U.S. PATENT DOCUMENTS

| | | | |
|---|---|---|---|
| 5,272,071 A | 12/1993 | Chappel | |
| 5,681,744 A * | 10/1997 | Greenstein | 435/320.1 |
| 5,922,601 A | 7/1999 | Baetscher et al. | 435/456 |
| 5,965,415 A | 10/1999 | Radman et al. | 435/172.3 |
| 6,146,894 A | 11/2000 | Nicolaides et al. | 435/440 |
| 6,166,178 A | 12/2000 | Chech et al. | 530/324 |
| 6,355,412 B1 | 3/2002 | Stewart et al. | 435/4 |
| 6,596,541 B2 * | 7/2003 | Murphy et al. | 435/463 |
| 6,921,666 B2 * | 7/2005 | Nicolaides et al. | 435/483 |
| 7,026,119 B2 * | 4/2006 | Nicolaides et al. | 435/6 |
| 2002/0151059 A1 * | 10/2002 | Te Riele et al. | 435/455 |

FOREIGN PATENT DOCUMENTS

| | | | |
|---|---|---|---|
| WO | WO 97/05268 | | 2/1997 |
| WO | WO 99/29837 A2 * | | 6/1999 |
| WO | WO 01/59092 A3 | | 8/2001 |
| WO | WO 01/61012 A1 | | 8/2001 |
| WO | WO 01/68882 A2 | | 9/2001 |
| WO | WO 02/054856 A1 | | 7/2002 |
| WO | WO 03/072732 A2 | | 9/2003 |

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Stryer (1988) Biochemistry, 3$^{rd}$ Ed., WH Freeman & Co., New York, NY, pp. 77 and 82.*
mARTI, et al. (2002) J. Cell. Physiol., 191: 28-41.*
Flores-Rozas, et al. (2000) TIBS, 196-200.*
Henke, et al. (2002) Appl. Microbiol. Biotechnol., 60: 320-26.*
Warlick, et al. (2000) Biochem. Pharmacol., 59: 141-51.*
Allen, D.J., et al., "MutS mediates heteroduplex loop formation by a translocation mechanism," *EMBO J.*, 1997, 16(4), 4467-4476.
Baker, S.M., et al., "Male defective in the DNA mismatch repair gene PMS2 exhibit abnormal chromosome synapsis in meiosis," *Cell*, Jul. 28, 1995, 82, 309-319.
Belmont, P., et al., "Synthesis and study of a new adenine—acridine tandem, inhibitor of exonuclease III," *Bioorg. Med. Chem. Lett.*, 2000, 10, 293-295.
Bhaumik, S., et al., "Optical imaging of *Renilla* luciferase reporter gene expression in living mice," *Proc. Natl. Acad. Sci.* USA, Jan. 8, 2002, 99(1), 377-382.
Bjornson, K.P., et al., "Modulation of MutS ATP hydrolysis by DNA cofactors," *Biochem.*, 2000, 39, 3176-3183.
Brasier, A.R., et al., "Optimized use of the firefly luciferase assay as a reporter gene in mammalian cell lines," *BioTechniques*, 1989, 7(10),1116-1122.
Chino, M., et al., "Effect of a novel antibiotic, heliquinomycin, on DNA helicase and cell growth," *J. of Antibiot.*, May 1998, 51(5), 480-486.
Colcher, D., et al., "Use of monoclonal antibodies as radiopharmaceuticals for the localization of human carcinoma xenografts in athymic mice," *Meth. Enzymol.*, 1986, 121, 802-816.
De Wind, N., et al., "Inactivation of the mouse *Msh2* gene results in mismatch repair deficiency, methylation tolerance, hyperrecombination, and predisposition to cancer," *Cell*, Jul. 28, 1995, 82, 321-300.
Elliott, B., et al., "Repair of double-strand breaks by homologous recombination in Mismatch Repair-defective mammalian cells," *Mol. Cell Biol.*, Apr. 2001, 21(8), 2671-2682.

(Continued)

Primary Examiner—Robert M Kelly
(74) Attorney, Agent, or Firm—Woodcock Washburn, LLP

(57) ABSTRACT

Inhibitors of mismatch repair can be used to generate hypermutable cells and organisms. By inhibiting this process in cells, new cell lines and varieties with novel and useful properties can be prepared more efficiently than by relying on the natural rate of homologous recombination. These methods are useful for generating targeted loci that can alter the expression profiles of target genes as well as tag exons of a gene with a reporter marker to facilitate the monitoring of a given gene product when the host is grown under different conditions or exposed to biological and chemical entities.

46 Claims, 5 Drawing Sheets

OTHER PUBLICATIONS

Galio, L., et al., "ATP hydrolysis-dependent formation of a dynamic ternary nucleoprotein complex with *MutS* and *MutL*," *Nucl. Acids-Res.*, 1999, 27(11), 2325-2331.

Grasso, L., et al., "Molecular analysis of human interleukin-9 receptor transcripts in peripheral blood mononuclear cells. Identification of a splice variant encoding for a nonfunctional cell surface receptor," *J. Biol. Chem.*, Sep. 11, 1998, 273(37), 24016-24024.

Guarente, L., et al., "Fusion of *Escherichia coli* lacZ to the cytochrome c gene of *Saccharomyces cerevisiae*," *Proc. Natl. Acad. Sci. USA*, Apr. 1981, 78(4), 2199-2203.

Huang, Y-C., et al., "*N*-ethylmaleimide profiling of yeast NADP-dependent isocitrate dehydrogenase," *Arch. Biochem. Biophys.*, Jan. 10, 1995, 316(1), 485-492.

Igoucheva, O., et al., "Targeted gene correction by small single-stranded oligonucleotides in mammalian cells," *Gene Ther.*, 2001, 8, 391-399.

Inbar, O., et al., "The relationship between homology length and crossing over during the repair of a broken chromosome," *J. Biol. Chem.*, Oct. 6, 2000, 275(40), 30833-30838.

Jiricny, J., et al., "Mismatch repair defects in cancer," *Curr. Opon. Genet. Dev.*, 2000, 10, 157-161.

Kaufman, R.J., et al., "Improved vectors for stable expression of foreign genes in mammalian cells by use of the untranslated leader sequence from EMC virus," *Nucl. Acids Res.*, 1991, 19(16), 4485-4490.

Kukhanova, M., et al., "Unique inhibitory effect of 1-(2'-deoxy-2'fluoro-β-L-arabinofuranosyl)-5-methyluracil 5'-triphosphate on Epstein-barr virus and human DNA polymerases," *Biochem. Pharmacol.*, 1998, 55, 1181-1187.

Kuwakado, K., et al., "Aphidicolin potentiates apoptosis induced by arabinosyl nucleosides in human myeloid leukemia cell lines," *Biochem. Pharmacol.*, 1993, 46(11), 1909-1916.

Lehninger, A.L., The amino acid building blocks of proteins, *Biochemistry, 2nd Ed. Worth Publishers, Inc.*, 1975, Chapter 4, 72-77.

Lemaigre, F.P., et al., "Transcriptional control of genes that regulate glycolysis and gluconeogenesis in adult liver," *Biochem. J.*, 1994, 303, 1-14.

Lin, C.T., et al., "Suppression of gene amplification and chromosomal DNA integration by the DNA mismatch repair system," *Nucl. Acid Res.*, 2001, 29(16), 3304-3310.

Lipkin, S.M., et al., "MLH3: a DNA mismatch repair gene associated with mammalian microsatellite instability," *Nat. Genet.*, Jan. 2000, 24, XP-002165243, 27-35.

Liu, T., et al., "Microsatellite instability as a predictor of a mutation in a DNA mismatch repair gene in familial colorectal cancer," *Genes Chrom. Cancer*, 2000, 27, 17-25.

Loeken, M.R., "Effects of mutation of the CREB binding site of the somatostatin promoter on cyclic AMP responsiveness in CV-1 cells," *Gene Expr.*, 1993, 3(3), 253-264.

Ma, C., et al., "Sister chromatid fusion initiates amplification of the dihydrofolate reductase gene in Chinese hamster cells," *Genes Dev.*, 1993, 7, 605-620.

Martin, S.J., et al., "Induction of apoptosis (programmed cell death) in human leukemic HL-60 cells by inhibition of RNA or protein synthesis," *J. Immunol.*, Sep. 15, 1990, 145(6), 18591867.

McGehee, R.E., et al., "Differentiation-specific element: a *cis*-acting developmental switch required for the sustained transcriptional expression of the angiotensinogen gene during hormonal-induced differentiation of 3T3-L1 fibroblasts to adipocytes," *Mol. Endocrinol.*, 1993, 7, 551-560.

Mellon, P.L., et al., "Regulation of transcription by cyclic AMP-dependent protein kinase," *Proc. Natl. Acad. Sci. USA*, Jul. 1989, 86, 4887-4891.

Modrich, P., "Mismatch repair, genetic stability, and cancer," *Science*, Dec. 23, 1994, 266, 1959-1960.

Nicolaides, N.C., et al., "A naturally occurring *hPMS2* mutation can confer a dominant negative mutator phenotype," *Mol. Cell. Biol.*, Mar. 1998, 18(3), 1635-1641.

Nicolaides, N.C., et al., "Genomic organization of the human *PMS2* gene family," *Genomics*, 1995, 30, 195-206.

Nicolaides, N.C., et al., "Interleukin 9: a candidate gene for asthma," *Proc. Natl. Acad. Sci. USA*, Nov. 1997, 94, 13175-13180.

O'Reilly, M.A., et al., "Identification of an activating transcription factor (ATF) binding site in the human transforming growth factor-β2 promoter," *J. Biol. Chem.*, Oct. 5, 1992, 267(28), 19938-19943.

Ono, K., et al., "Inhibition of DNA polymerase α by 2',3'-dideoxyribonucleoside 5'-triphosphates: effect of manganese ion," *Biomed. Pharmacother.*, 1984, 38, 382-389.

Perucho, M., "Cancer of the microsatellite mutator phenotype," *Biol. Chem.*, Nov. 1996, 377, 675-684.

Potter, H., et al., "Enhancer-dependent expression of human κ immunoglobulin genes introduced into mouse pre-B lymphocytes by eletroporation," *Proc. Natl. Acad. Sci. USA*, Nov. 1984, 81, 7161-7165.

Prolla, T.A., et al., "MLH1, PMS1, and MSH2 interaction during the initiation of DNA mismatch repair in yeast," *Science*, Aug. 19, 1994, 264, 1091-1093.

Ray, P., et al., "Monitoring gene therapy with reporter gene imaging," *Semin. Nucl. Med.*, Oct. 2001, XXXI(4), 312-320.

Rayssigguier, C., et al., "The barrier to recombination between *Escherichia coli* and *Salmonella typhimurium* is disruptedin mismatch-repair mutants," *Nature*, Nov. 23, 1989, 342, 396-401.

Sambrook, et al., Molecular Cloning: A Laboratory Manual, *Cold Spring Harbor Press*, NY, 2000.

Schaffner, W., et al., "Direct transfer of cloned genes from bacteria to mammalian cells," *Proc. Natl. Acad. Sci. USA*, Apr. 1980, 77(4), 2163-2167.

Seed, B., et al., "A simple phase-extraction assay for chloramphenicol acyltransferase activity," *Gene*, 1988, 67, 271-277.

Selva, E., et al., "Mismatch correction acts as a barrier to homeologous recombination in *Saccharomyces cerevisiae*," *Genetics*, Mar. 1995, 139, 1175-1188.

Spampinato, C., et al., "The MutL ATPase is required for mismatch repair," *J. Biol. Chem.*, Mar. 31, 2000, 275(13), 9863-9869.

Strand, M., et al., "Destabilization of tracts of simple repetitive DNA in yeast by mutations affecting DNA mismatch repair," *Nature*, Sep. 16, 1993, 365, 274-276.

Todaka, M., et al., "The role of insulin in activation of two enhancers in the mouse GLUT1 gene," *J. Biol. Chem.*, Nov. 18, 1994, 269(46), 29265-29270.

Treisman, R., "The SRE: a growth factor responsive transcriptional regulator," *Seminars in Cancer Biol.*, 1990, 1, 47-58.

Waldman, T., et al., "p21 is necessary for the p53-mediated $G_1$ arrest in human cancer cells," *Cancer Res.*, Nov. 15, 1995, 55, 5187-5190.

Wang, Y., et al., "*Renilla* luciferase-*Aequorea* GFP (Ruc-GFP) fusion protein, a novel dual reporter for real-time imaging of gene expression in cell cultures and in live animals," *Mol. Genet. Genomics*, 2002, 268, 160-168.

Watson, et al. (Eds.), Molecular Biology of the Gene, 4th Ed., *The Benjamin/Cummings Publishing Co., Inc.*, Menlo Park, CA, 1987.

Wensel, et al., *Radioimmunoimaging and Radioimmunotherapy*, Esevier, NY, 1983.

Wigler, M., et al., "Transformation of mammalian cells with an amplifiable dominant-acting gene," *Proc. Natl. Acad. Sci. USA*, Jun. 1980, 77(6), 3567-3570.

Ye, J., et al., "Characterization of a silencer regulatory element in the human interferon-γ promoter," *J. Boil. Chem.*, Oct. 14, 1994, 269(41), 25728-25734.

Nicolaides, N.C., "Analysis of the 5' region of PMS2 reveals heterogeneous transcripts and a novel overlapping gene," Genomics, 1995, 29, 329-334.

Chen, P-C. et al., "Contributions by MutL Homologues *Mlh3* and *Pms2* to DNA Mismatch Repair and Tumor Suppression in the Mouse", *Cancer Res*, 2005, 65(19), 8662-8670.

\* cited by examiner

A: Hygromycin-green fluorescent fusion protein (Hyg-GFP) (SEQ ID NO: 46)

```
1    mkkpeltats vekfliekfd svsdlmqlse geesrafsfd vggrgyvlrv nscadgfykd
61   ryvyrhfasa alpipevldi gefsesltyc isrraqgvtl qdlpetelpa vlqpvaeamd
121  aiaaadlsqt sgfgpfgpqg igqyttwrdf icaiadphvy hwqtvmddtv sasvaqalde
181  lmlwaedcpe vrhlvhadfg snnvltdngr itavidwsea mfgdsqyeva niffwrpwla
241  cmeqqtryfe rrhpelagsp rlraymlrig ldqlyqslvd gnfddaawaq grcdaivrsg
301  agtvgrtqia rrsaavwtdg cvevladsgn rrpstrpdre mgeanmskge elftgvvpil
361  veldgdvhgh kfsvrgegeg dadygkleik ficttgklpv pwptlvttlg ygilcfaryp
421  ehmkmndffk sampegyiqe rtiffqddgk yktrgevkfe gdtlvnriel kgmdfkedgn
481  ilghkleynf nshnvyimpd kannglkvnf kirhnieggg vqladhyqtn vplgdgpvli
541  pinhylstqt aiskdrnetr dhmvfleffs acghthgmde lyk
```

Fig. 3A

B: Hygromycin-luciferase fusion protein (Hyg-Luc) (SEQ ID NO: 47)

```
1    mkkpeltats  vekfliekfd  svsdlmqlse  geesrafsfd  vggrgyvlrv  nscadgfykd
61   ryvyrhfasa  alpipevldi  gefsesltyc  isrraqgvtl  qdlpetelpa  vlqpvaeamd
121  aiaaadlsqt  sgfgpfgpqg  igqyttwrdf  icaiadphvy  hwqtvmddtv  sasvaqalde
181  lmlwaedcpe  vrhlvhadfg  snnvltdngr  itavidwsea  mfgdsqyeva  niffwrpwla
241  cmeqqtryfe  rrhpelagsp  rlraymlrig  ldqlyqslvd  gnfddaawaq  grcdaivrsg
301  agtvgrtqia  rrsaavwtdg  cvevladsgn  rrpstrpdre  mgeanmedak  nikkgpapfy
361  pledgtageq  lhkamkryal  vpgtiaftda  hievnityae  yfemsvrlae  amkryglntn
421  hrivvcsens  lqffmpvlga  lfigvavapa  ndiynerell  nsmnisqptv  vfvskkglqk
481  ilnvqkklpi  iqkiiimdsk  tdyqgfqsmy  tfvtshlppg  fneydfvpes  fdrdktiali
541  mnssgstglp  kgvalphrta  cvrfshardp  ifgnqiipdt  ailsvvpfhh  gfgmfttlgy
601  licgfrvvlm  yrfeeelflr  slqdykiqsa  llvptlfsff  akstlidkyd  lsnlheiasg
661  gaplskevge  avakrfhlpg  irqgygltet  tsailitpeg  ddkpgavgkv  vpffeakvvd
721  ldtgktlgvn  qrgelcvrgp  mimsgyvnnp  eatnalidkd  gwlhsgdiay  wdedehffiv
781  drlkslikyk  gyqvapaele  sillqhpnif  dagvaglpdd  dagelpaavv  vlehgktmte
841  keivdyvasq  vttakklrgg  vvfvdevpkg  ltgkldarki  reilikakkg  gkskl
```

Fig. 3B

SEQUENCE LISTING

<160> NUMBER OF SEQ ID NOS: 47

<210> SEQ ID NO 1
<211> LENGTH: 859
<212> TYPE: PRT
<213> ORGANISM: Mus musculus

<400> SEQUENCE: 1

Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60

Leu Ile Glu Val Ser Asp Asn Gly Cys Gly Val Glu Glu Glu Asn Phe
65                  70                  75                  80

-continued

```
Glu Gly Leu Ala Leu Lys His His Thr Ser Lys Ile Gln Glu Phe Ala
             85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr Arg Leu Val Phe Asp His Asn Gly Lys Ile Thr
    130                 135                 140

Gln Lys Thr Pro Tyr Pro Arg Pro Lys Gly Thr Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
        195                 200                 205

Gly Lys Arg His Ala Val Val Cys Thr Ser Gly Thr Ser Gly Met Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Arg Ala Ser
            260                 265                 270

Phe His Ser Ala Arg Thr Ala Pro Gly Val Gln Gln Thr Gly Ser
        275                 280                 285

Phe Ser Ser Ile Arg Gly Pro Val Thr Gln Gln Arg Ser Leu Ser
    290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Ala Asn
        355                 360                 365

Lys Leu Asn Val Asn Gln Gln Pro Leu Leu Asp Val Glu Gly Asn Leu
    370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
            420                 425                 430

Ile Lys Ser Arg Gly Pro Glu Thr Ala Glu Leu Thr Arg Ser Phe Pro
        435                 440                 445

Ser Glu Lys Arg Gly Val Leu Ser Ser Tyr Pro Ser Asp Val Ile Ser
    450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495
```

```
Leu Ser Ser Thr Ser Ala Gly Ser Glu Glu Phe Ser Thr Pro Glu
                500                 505                 510

Val Ala Ser Ser Phe Ser Ser Asp Tyr Asn Val Ser Ser Leu Glu Asp
            515                 520                 525

Arg Pro Ser Gln Glu Thr Ile Asn Cys Gly Asp Leu Asp Cys Arg Pro
        530                 535                 540

Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
                565                 570                 575

Lys Thr Glu Glu Arg Pro Ser Asn Val Asn Ile Ser Gln Arg Leu Pro
            580                 585                 590

Gly Pro Gln Ser Thr Ser Ala Ala Glu Val Asp Val Ala Ile Lys Met
        595                 600                 605

Asn Lys Arg Ile Val Leu Leu Glu Phe Ser Leu Ser Ser Leu Ala Lys
610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
                645                 650                 655

Ala Glu Asp Glu Leu Arg Lys Glu Ile Ser Lys Ser Met Phe Ala Glu
            660                 665                 670

Met Glu Ile Leu Gly Gln Phe Asn Leu Gly Phe Ile Val Thr Lys Leu
        675                 680                 685

Lys Glu Asp Leu Phe Leu Val Asp Gln His Ala Ala Asp Glu Lys Tyr
690                 695                 700

Asn Phe Glu Met Leu Gln Gln His Thr Val Leu Gln Ala Gln Arg Leu
705                 710                 715                 720

Ile Thr Pro Gln Thr Leu Asn Leu Thr Ala Val Asn Glu Ala Val Leu
                725                 730                 735

Ile Glu Asn Leu Glu Ile Phe Arg Lys Asn Gly Phe Asp Phe Val Ile
            740                 745                 750

Asp Glu Asp Ala Pro Val Thr Glu Arg Ala Lys Leu Ile Ser Leu Pro
        755                 760                 765

Thr Ser Lys Asn Trp Thr Phe Gly Pro Gln Asp Ile Asp Glu Leu Ile
770                 775                 780

Phe Met Leu Ser Asp Ser Pro Gly Val Met Cys Arg Pro Ser Arg Val
785                 790                 795                 800

Arg Gln Met Phe Ala Ser Arg Ala Cys Arg Lys Ser Val Met Ile Gly
                805                 810                 815

Thr Ala Leu Asn Ala Ser Glu Met Lys Lys Leu Ile Thr His Met Gly
            820                 825                 830

Glu Met Asp His Pro Trp Asn Cys Pro His Gly Arg Pro Thr Met Arg
        835                 840                 845

His Val Ala Asn Leu Asp Val Ile Ser Gln Asn
850                 855
```

<210> SEQ ID NO 2
<211> LENGTH: 3056
<212> TYPE: DNA
<213> ORGANISM: Mus musculus

<400> SEQUENCE: 2

```
gaattccggt gaaggtcctg aagaatttcc agattcctga gtatcattgg aggagacaga        60
taacctgtcg tcaggtaacg atggtgtata tgcaacagaa atgggtgttc ctggagacgc       120
gtcttttccc gagagcggca ccgcaactct cccgcggtga ctgtgactgg aggagtcctg       180
catccatgga gcaaaccgaa ggcgtgagta cagaatgtgc taaggccatc aagcctattg       240
atgggaagtc agtccatcaa atttgttctg ggcaggtgat actcagttta agcaccgctg       300
tgaaggagtt gatagaaaat agtgtagatg ctggtgctac tactattgat ctaaggctta       360
aagactatgg ggtggacctc attgaagttt cagacaatgg atgtggggta gaagaagaaa       420
actttgaagg tctagctctg aaacatcaca catctaagat tcaagagttt gccgacctca       480
cgcaggttga aactttcggc tttgggggga agctctgag ctctctgtgt gcactaagtg       540
atgtcactat atctacctgc cacgggtctg caagcgttgg gactcgactg gtgtttgacc       600
ataatgggaa aatcacccag aaaactccct acccccgacc taaaggaacc acagtcagtg       660
tgcagcactt attttataca ctacccgtgc gttacaaaga gtttcagagg aacattaaaa       720
aggagtattc caaaatggtg caggtcttac aggcgtactg tatcatctca gcaggcgtcc       780
gtgtaagctg cactaatcag ctcggacagg ggaagcggca cgctgtggtg tgcacaagcg       840
gcacgtctgg catgaaggaa aatatcgggt ctgtgtttgg ccagaagcag ttgcaaagcc       900
tcattccttt tgttcagctg cccctagtg acgctgtgtg tgaagagtac ggcctgagca       960
cttcaggacg ccacaaaacc ttttctacgt ttcgggcttc atttcacagt gcacgcacgg      1020
cgccgggagg agtgcaacag acaggcagtt tttcttcatc aatcagaggc cctgtgaccc      1080
agcaaaggtc tctaagcttg tcaatgaggt tttatcacat gtataaccgg catcagtacc      1140
catttgtcgt ccttaacgtt tccgttgact cagaatgtgt ggatattaat gtaactccag      1200
ataaaaggca aattctacta caagaagaga agctattgct ggccgttta aagacctcct      1260
tgataggaat gtttgacagt gatgcaaaca agcttaatgt caaccagcag ccactgctag      1320
atgttgaagg taacttagta aagctgcata ctgcagaact agaaaagcct gtgccaggaa      1380
agcaagataa ctctccttca ctgaagagca cagcagacga gaaaagggta gcatccatct      1440
ccaggctgag agaggccttt tctcttcatc ctactaaaga gatcaagtct aggggtccag      1500
agactgctga actgacacgg agttttccaa gtgagaaaag gggcgtgtta tcctcttatc      1560
cttcagacgt catctcttac agaggcctcc gtggctcgca ggacaaattg gtgagtccca      1620
cggacagccc tggtgactgt atggacagag agaaaataga aaaagactca gggctcagca      1680
gcacctcagc tggctctgag gaagagttca gcaccccaga agtggccagt agctttagca      1740
gtgactataa cgtgagctcc ctagaagaca gaccttctca ggaaaccata aactgtggtg      1800
acctggactg ccgtcctcca ggtacaggac agtccttgaa gccagaagac catggatatc      1860
aatgcaaagc tctacctcta gctcgtctgt cacccacaaa tgccaagcgc ttcaagacag      1920
aggaaagacc ctcaaatgtc aacatttctc aaagattgcc tggtcctcag agcacctcag      1980
cagctgaggt cgatgtagcc ataaaaatga ataagagaat cgtgctcctc gagttctctc      2040
tgagttctct agctaagcga atgaagcagt acagcacct aaaggcgcag aacaaacatg      2100
aactgagtta cagaaaattt agggccaaga tttgccctgg agaaaccaa gcagcagaag      2160
atgaactcag aaaagagatt agtaaatcga tgtttgcaga gatggagatc ttgggtcagt      2220
ttaacctggg atttatagta accaaactga aagaggacct cttcctggtg gaccagcatg      2280
ctgcggatga gaagtacaac tttgagatgc tgcagcagca cacggtgctc caggcgcaga      2340
```

-continued

```
ggctcatcac acccccagact ctgaacttaa ctgctgtcaa tgaagctgta ctgatagaaa    2400
atctggaaat attcagaaag aatggctttg actttgtcat tgatgaggat gctccagtca    2460
ctgaaagggc taaattgatt tccttaccaa ctagtaaaaa ctggaccttt ggaccccaag    2520
atatagatga actgatcttt atgttaagtg acagccctgg ggtcatgtgc cggccctcac    2580
gagtcagaca gatgtttgct tccagagcct gtcggaagtc agtgatgatt ggaacggcgc    2640
tcaatgcgag cgagatgaag aagctcatca cccacatggg tgagtggac caccctgga    2700 actgccccca cggcaggcca accatgaggc acgttgccaa tctggatgtc atctctcaga    2760
actgacacac cccttgtagc atagagttta ttacagattg ttcggtttgc aaagagaagg    2820
ttttaagtaa tctgattatc gttgtacaaa aattagcatg ctgctttaat gtactggatc    2880
catttaaaag cagtgttaag gcaggcatga tggagtgttc ctctagctca gctacttggg    2940
tgatccggtg ggagctcatg tgagcccagg actttgagac cactccgagc cacattcatg    3000
agactcaatt caaggacaaa aaaaaaaaga tatttttgaa gccttttaaa aaaaaa        3056
```

<210> SEQ ID NO 3
<211> LENGTH: 932
<212> TYPE: PRT
<213> ORGANISM: Homo sapiens

<400> SEQUENCE: 3

```
Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
    210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255
```

-continued

```
Arg Ser Phe Ile Phe Ile Asn Ser Arg Pro Val His Gln Lys Asp Ile
                260                 265                 270

Leu Lys Leu Ile Arg His His Tyr Asn Leu Lys Cys Leu Lys Glu Ser
            275                 280                 285

Thr Arg Leu Tyr Pro Val Phe Phe Leu Lys Ile Asp Val Pro Thr Ala
        290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
            340                 345                 350

Val Ser Ala Ala Asp Ile Val Leu Ser Lys Thr Ala Glu Thr Asp Val
        355                 360                 365

Leu Phe Asn Lys Val Glu Ser Ser Gly Lys Asn Tyr Ser Asn Val Asp
    370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
            420                 425                 430

Lys Asn Ala Phe Gln Asp Ile Ser Met Ser Asn Val Ser Trp Glu Asn
        435                 440                 445

Ser Gln Thr Glu Tyr Ser Lys Thr Cys Phe Ile Ser Ser Val Lys His
    450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
            500                 505                 510

Glu Pro Val Lys Ile Leu Val Pro Glu Lys Ser Leu Pro Cys Lys Val
        515                 520                 525

Ser Asn Asn Asn Tyr Pro Ile Pro Glu Gln Met Asn Leu Asn Glu Asp
    530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Pro Met Ser
                565                 570                 575

Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
        595                 600                 605

Trp Lys Thr Leu Ser Glu Glu Lys Leu Lys Tyr Glu Glu Lys Ala
    610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Ile Lys Pro
                645                 650                 655

Thr Ser Ala Trp Asn Leu Ala Gln Lys His Lys Leu Lys Thr Ser Leu
            660                 665                 670
```

```
Ser Asn Gln Pro Lys Leu Asp Glu Leu Leu Gln Ser Gln Ile Glu Lys
        675                 680                 685

Arg Arg Ser Gln Asn Ile Lys Met Val Gln Ile Pro Phe Ser Met Lys
        690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
                740                 745                 750

Glu Glu Ala Leu Leu Phe Lys Arg Leu Leu Glu Asn His Lys Leu Pro
                755                 760                 765

Ala Glu Pro Leu Glu Lys Pro Ile Met Leu Thr Glu Ser Leu Phe Asn
        770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
                820                 825                 830

Leu Glu Ile Glu Gly Met Ala Asn Cys Leu Pro Phe Tyr Gly Val Ala
        835                 840                 845

Asp Leu Lys Glu Ile Leu Asn Ala Ile Leu Asn Arg Asn Ala Lys Glu
        850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                885                 890                 895

Ile Gln Asp Ile Ile Tyr Arg Met Lys His Gln Phe Gly Asn Glu Ile
                900                 905                 910

Lys Glu Cys Val His Gly Arg Pro Phe Phe His His Leu Thr Tyr Leu
        915                 920                 925

Pro Glu Thr Thr
        930

<210> SEQ ID NO 4
<211> LENGTH: 2771
<212> TYPE: DNA
<213> ORGANISM: Homo sapiens

<400> SEQUENCE: 4
cgaggcggat cgggtgttgc atccatggag cgagctgaga gctcgagtac agaacctgct      60
aaggccatca aacctattga tcggaagtca gtccatcaga tttgctctgg gcaggtggta     120
ctgagtctaa gcactgcggt aaaggagtta gtagaaaaca gtctggatgc tggtgccact     180
aatattgatc taaagcttaa ggactatgga gtggatctta ttgaagtttc agacaatgga     240 tgtgggtag aagaagaaaa cttcgaaggc ttaactctga acatcacac atctaagatt       300 caagagtttg ccgacctaac tcaggttgaa acttttggct tcggggggga agctctgagc     360
tcactttgtg cactgagcga tgtcaccatt tctacctgcc acgcatcggc gaaggttgga     420
actcgactga tgtttgatca aatgggaaa attatccaga aaccccta cccccgcccc        480 agagggacca cagtcagcgt gcagcagtta ttttccacac tacctgtgcg ccataaggaa     540
tttcaaagga atattaagaa ggagtatgcc aaaatggtcc aggtcttaca tgcatactgt     600
```

-continued

```
atcatttcag caggcatccg tgtaagttgc accaatcagc ttggacaagg aaaacgacag      660
cctgtggtat gcacaggtgg aagccccagc ataaaggaaa atatcggctc tgtgtttggg      720
cagaagcagt tgcaaagcct cattccttt gttcagctgc ccctagtga ctccgtgtgt        780 gaagagtacg gtttgagctg ttcggatgct ctgcataatc ttttttacat ctcaggtttc      840
atttcacaat gcacgcatgg agttggaagg agttcaacag acagacagtt tttctttatc     900
aaccggcggc cttgtgaccc agcaaaggtc tgcagactcg tgaatgaggt ctaccacatg      960
tataatcgac accagtatcc atttgttgtt cttaacattt ctgttgattc agaatgcgtt     1020
gatatcaatg ttactccaga taaaaggcaa attttgctac aagaggaaaa gcttttgttg     1080
gcagttttaa agacctcttt gataggaatg tttgatagtg atgtcaacaa gctaaatgtc     1140
agtcagcagc cactgctgga tgttgaaggt aacttaataa aaatgcatgc agcggatttg     1200
gaaaagccca tggtagaaaa gcaggatcaa tccccttcat taaggactgg agaagaaaaa     1260
aaagacgtgt ccattccag actgcgagag gccttttctc ttcgtcacac aacagagaac      1320
aagcctcaca gcccaaagac tccagaacca agaaggagcc ctctaggaca gaaaaggggt     1380
atgctgtctt ctagcacttc aggtgccatc tctgacaaag gcgtcctgag acctcagaaa     1440
gaggcagtga gttccagtca cggacccagt gaccctacgg acagagcgga ggtggagaag     1500
gactcggggc acggcagcac ttccgtggat tctgaggggt tcagcatccc agacacgggc     1560
agtcactgca gcagcgagta tgcggccagc tccccagggg cagggggctc gcaggaacat     1620
gtggactctc aggagaaagc gcctgaaact gacgactctt tttcagatgt ggactgccat     1680
tcaaaccagg aagataccgg atgtaaattt cgagttttgc ctcagccaac taatctcgca     1740
accccaaaca caaagcgttt taaaaaagaa gaaattcttt ccagttctga catttgtcaa     1800
aagttagtaa atactcagga catgtcagcc tctcaggttg atgtagctgt gaaaattaat     1860
aagaaagttg tgccctgga cttttctatg agttctttag ctaaacgaat aaagcagtta     1920
catcatgaag cacagcaaag tgaaggggaa cagaattaca ggaagtttag ggcaaagatt     1980
tgtcctggag aaaatcaagc agccgaagat gaactaagaa aagagataag taaaacgatg     2040
tttgcagaaa tggaaatcat tggtcagttt aacctgggat ttataataac caaactgaat     2100
gaggatatct tcatagtgga ccagcatgcc acggacgaga agtataactt cgagatgctg     2160
cagcagcaca ccgtgctcca ggggcagagg ctcatagcac ctcagactct caacttaact     2220
gctgttaatg aagctgttct gatagaaaat ctggaaatat ttagaaagaa tggctttgat     2280
tttgttatcg atgaaaatgc tccagtcact gaaagggcta aactgatttc cttgccaact     2340
agtaaaaact ggaccttcgg accccaggac gtcgatgaac tgatcttcat gctgagcgac     2400
agccctgggg tcatgtgccg gccttcccga gtcaagcaga tgtttgcctc cagagcctgc     2460
cggaagtcgg tgatgattgg gactgctctt aacacaagcg agatgaagaa actgatcacc     2520
cacatggggg agatggacca ccctggaac tgtccccatg gaaggccaac catgagacac      2580
atcgccaacc tgggtgtcat ttctcagaac tgaccgtagt cactgtatgg aataattggt     2640
tttatcgcag attttttatgt tttgaaagac agagtcttca ctaaccttt ttgttttaaa     2700 atgaaacctg ctacttaaaa aaaatacaca tcacacccat ttaaaagtga tcttgagaac     2760 ctttttcaaac c                                                          2771
```

<210> SEQ ID NO 5
<211> LENGTH: 932
<212> TYPE: PRT
<213> ORGANISM: Homo sapiens

```
<400> SEQUENCE: 5

Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
        275                 280                 285

Thr Arg Leu Tyr Pro Val Phe Phe Leu Lys Ile Asp Val Pro Thr Ala
290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
            340                 345                 350

Val Ser Ala Ala Asp Ile Val Leu Ser Lys Thr Ala Glu Thr Asp Val
        355                 360                 365

Leu Phe Asn Lys Val Glu Ser Ser Gly Lys Asn Tyr Ser Asn Val Asp
370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415
```

```
Gly Tyr Gly His Cys Ser Ser Glu Ile Ser Asn Ile Asp Lys Asn Thr
            420                 425                 430

Lys Asn Ala Phe Gln Asp Ile Ser Met Ser Asn Val Ser Trp Glu Asn
        435                 440                 445

Ser Gln Thr Glu Tyr Ser Lys Thr Cys Phe Ile Ser Ser Val Lys His
    450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
            500                 505                 510

Glu Pro Val Lys Ile Leu Val Pro Glu Lys Ser Leu Pro Cys Lys Val
        515                 520                 525

Ser Asn Asn Asn Tyr Pro Ile Pro Glu Gln Met Asn Leu Asn Glu Asp
    530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
        595                 600                 605

Trp Lys Thr Leu Ser Glu Glu Lys Leu Lys Tyr Glu Glu Lys Ala
    610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Lys Ile Lys Pro
                645                 650                 655

Thr Ser Ala Trp Asn Leu Ala Gln Lys His Lys Leu Lys Thr Ser Leu
            660                 665                 670

Ser Asn Gln Pro Lys Leu Asp Glu Leu Leu Gln Ser Gln Ile Glu Lys
        675                 680                 685

Arg Arg Ser Gln Asn Ile Lys Met Val Gln Ile Pro Phe Ser Met Lys
    690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
            740                 745                 750

Glu Glu Ala Leu Leu Phe Lys Arg Leu Leu Glu Asn His Lys Leu Pro
        755                 760                 765

Ala Glu Pro Leu Glu Lys Pro Ile Met Leu Thr Glu Ser Leu Phe Asn
    770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
            820                 825                 830
```

```
Leu Glu Ile Glu Gly Met Ala Asn Cys Leu Pro Phe Tyr Gly Val Ala
        835                 840                 845
Asp Leu Lys Glu Ile Leu Asn Ala Ile Leu Asn Arg Asn Ala Lys Glu
    850                 855                 860
Val Tyr Glu Cys Arg Pro Arg Lys Val Ile Ser Tyr Leu Glu Gly Glu
865                 870                 875                 880
Ala Val Arg Leu Ser Arg Gln Leu Pro Met Tyr Leu Ser Lys Glu Asp
                885                 890                 895
Ile Gln Asp Ile Ile Tyr Arg Met Lys His Gln Phe Gly Asn Glu Ile
            900                 905                 910
Lys Glu Cys Val His Gly Arg Pro Phe Phe His His Leu Thr Tyr Leu
        915                 920                 925
Pro Glu Thr Thr
        930

<210> SEQ ID NO 6
<211> LENGTH: 3063
<212> TYPE: DNA
<213> ORGANISM: Homo sapiens

<400> SEQUENCE: 6
ggcacgagtg gctgcttgcg gctagtggat ggtaattgcc tgcctcgcgc tagcagcaag      60
ctgctctgtt aaaagcgaaa atgaaacaat tgcctgcggc aacagttcga ctcctttcaa     120
gttctcagat catcacttcg gtggtcagtg ttgtaaaaga gcttattgaa aactccttgg     180
atgctggtgc cacaagcgta gatgttaaac tggagaacta tggatttgat aaaattgagg     240
tgcgagataa cggggagggt atcaaggctg ttgatgcacc tgtaatggca atgaagtact     300
acacctcaaa aataaatagt catgaagatc ttgaaaattt gacaacttac ggttttcgtg     360
gagaagcctt ggggtcaatt tgttgtatag ctgaggtttt aattacaaca gaacggctg     420
ctgataattt tagcacccag tatgttttag atggcagtgg ccacatactt tctcagaaac     480
cttcacatct tggtcaaggt acaactgtaa ctgctttaag attatttaag aatctacctg     540
taagaaagca gttttactca actgcaaaaa aatgtaaaga tgaaataaaa aagatccaag     600
atctcctcat gagctttggt atccttaaac ctgacttaag gattgtcttt gtacataaca     660
aggcagttat ttggcagaaa agcagagtat cagatcacaa gatggctctc atgtcagttc     720
tggggactgc tgttatgaac aatatggaat cctttcagta ccactctgaa gaatctcaga     780
tttatctcag tggatttctt ccaaagtgtg atgcagacca ctctttcact agtctttcaa     840
caccagaaag aagtttcatc ttcataaaca gtcgaccagt acatcaaaaa gatatcttaa     900
gttaatccg acatcattac aatctgaaat gcctaaagga atctactcgt ttgtatcctg     960
tttctttct gaaatcgat gttcctacag ctgatgttga tgtaaattta acaccagata    1020
aaagccaagt attattacaa aataaggaat ctgtttaat tgctcttgaa atctgatga    1080
cgacttgtta tggaccatta cctagtacaa attcttatga aataataaa acagatgttt    1140
ccgcagctga catcgttctt agtaaaacag cagaaacaga tgtgcttttt aataaagtgg    1200
aatcatctgg aaagaattat tcaaatgttg atacttcagt cattccattc caaaatgata    1260
tgcataatga tgaatctgga aaaacactg atgattgttt aaatcaccag ataagtattg    1320
gtgactttgg ttatggtcat tgtagtagtg aaatttctaa cattgataaa aacactaaga    1380
atgcatttca ggacatttca atgagtaatg tatcatggga gaactctcag acggaatata    1440
gtaaaacttg ttttataagt tccgttaagc acacccagtc agaaaatggc aataaagacc    1500
```

-continued

```
atatagatga gagtgggaa aatgaggaag aagcaggtct tgaaaactct tcggaaattt      1560
ctgcagatga gtggagcagg ggaaatatac ttaaaaattc agtgggagag aatattgaac    1620
ctgtgaaaat tttagtgcct gaaaaaagtt taccatgtaa agtaagtaat aataattatc    1680
caatccctga acaaatgaat cttaatgaag attcatgtaa caaaaaatca aatgtaatag    1740
ataataaatc tggaaaagtt acagcttatg atttacttag caatcgagta atcaagaaac    1800
ccatgtcagc aagtgctctt tttgttcaag atcatcgtcc tcagtttctc atagaaaatc    1860
ctaagactag tttagaggat gcaacactac aaattgaaga actgtggaag acattgagtg    1920
aagaggaaaa actgaaatat gaagagaagg ctactaaaga cttggaacga tacaatagtc    1980
aaatgaagag agccattgaa caggagtcac aaatgtcact aaaagatggc agaaaaaaga    2040
taaacccac cagcgcatgg aatttggccc agaagcacaa gttaaaaacc tcattatcta     2100
atcaaccaaa acttgatgaa ctccttcagt cccaaattga aaaagaagg agtcaaaata     2160
ttaaaatggt acagatcccc ttttctatga aaacttaaa aataaatttt aagaaacaaa    2220
acaaagttga cttagaagag aaggatgaac cttgcttgat ccacaatctc aggtttcctg    2280
atgcatggct aatgacatcc aaaacagagg taatgttatt aaatccatat agagtagaag    2340
aagccctgct atttaaaaga cttcttgaga atcataaact tcctgcagag ccactggaaa    2400
agccaattat gttaacagag agtctttta atggatctca ttatttagac gttttatata    2460
aaatgacagc agatgaccaa agatacagtg gatcaactta cctgtctgat cctcgtctta    2520
cagcgaatgg tttcaagata aaattgatac caggagtttc aattactgaa aattacttgg    2580
aaatagaagg aatggctaat tgtctcccat tctatggagt agcagattta aaagaaattc    2640
ttaatgctat attaaacaga aatgcaaagg aagtttatga atgtagacct cgcaaagtga    2700
taagttattt agagggagaa gcagtgcgtc tatccagaca attacccatg tacttatcaa    2760
aagaggacat ccaagacatt atctacagaa tgaagcacca gtttggaaat gaaattaaag    2820
agtgtgttca tggtcgccca ttttttcatc atttaaccta tcttccagaa actacatgat    2880
taaatatgtt taagaagatt agttaccatt gaaattggtt ctgtcataaa acagcatgag    2940
tctggtttta aattatcttt gtattatgtg tcacatggtt attttttaaa tgaggattca    3000
ctgacttgtt tttatattga aaaagttcc acgtattgta gaaaacgtaa ataaactaat     3060
aac                                                                 3063
```

<210> SEQ ID NO 7
<211> LENGTH: 934
<212> TYPE: PRT
<213> ORGANISM: Homo sapiens

<400> SEQUENCE: 7

```
Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95
```

```
Gln Tyr Arg Val Glu Val Tyr Lys Asn Arg Ala Gly Asn Lys Ala Ser
            100                 105                 110
Lys Glu Asn Asp Trp Tyr Leu Ala Tyr Lys Ala Ser Pro Gly Asn Leu
        115                 120                 125
Ser Gln Phe Glu Asp Ile Leu Phe Gly Asn Asn Asp Met Ser Ala Ser
    130                 135                 140
Ile Gly Val Val Gly Val Lys Met Ser Ala Val Asp Gly Gln Arg Gln
145                 150                 155                 160
Val Gly Val Gly Tyr Val Asp Ser Ile Gln Arg Lys Leu Gly Leu Cys
                165                 170                 175
Glu Phe Pro Asp Asn Asp Gln Phe Ser Asn Leu Glu Ala Leu Leu Ile
            180                 185                 190
Gln Ile Gly Pro Lys Glu Cys Val Leu Pro Gly Gly Glu Thr Ala Gly
        195                 200                 205
Asp Met Gly Lys Leu Arg Gln Ile Ile Gln Arg Gly Gly Ile Leu Ile
    210                 215                 220
Thr Glu Arg Lys Lys Ala Asp Phe Ser Thr Lys Asp Ile Tyr Gln Asp
225                 230                 235                 240
Leu Asn Arg Leu Leu Lys Gly Lys Lys Gly Glu Gln Met Asn Ser Ala
                245                 250                 255
Val Leu Pro Glu Met Glu Asn Gln Val Ala Val Ser Ser Leu Ser Ala
            260                 265                 270
Val Ile Lys Phe Leu Glu Leu Leu Ser Asp Asp Ser Asn Phe Gly Gln
        275                 280                 285
Phe Glu Leu Thr Thr Phe Asp Phe Ser Gln Tyr Met Lys Leu Asp Ile
    290                 295                 300
Ala Ala Val Arg Ala Leu Asn Leu Phe Gln Gly Ser Val Glu Asp Thr
305                 310                 315                 320
Thr Gly Ser Gln Ser Leu Ala Ala Leu Leu Asn Lys Cys Lys Thr Pro
                325                 330                 335
Gln Gly Gln Arg Leu Val Asn Gln Trp Ile Lys Gln Pro Leu Met Asp
            340                 345                 350
Lys Asn Arg Ile Glu Glu Arg Leu Asn Leu Val Glu Ala Phe Val Glu
        355                 360                 365
Asp Ala Glu Leu Arg Gln Thr Leu Gln Glu Asp Leu Leu Arg Arg Phe
    370                 375                 380
Pro Asp Leu Asn Arg Leu Ala Lys Lys Phe Gln Arg Gln Ala Ala Asn
385                 390                 395                 400
Leu Gln Asp Cys Tyr Arg Leu Tyr Gln Gly Ile Asn Gln Leu Pro Asn
                405                 410                 415
Val Ile Gln Ala Leu Glu Lys His Glu Gly Lys His Gln Lys Leu Leu
            420                 425                 430
Leu Ala Val Phe Val Thr Pro Leu Thr Asp Leu Arg Ser Asp Phe Ser
        435                 440                 445
Lys Phe Gln Glu Met Ile Glu Thr Thr Leu Asp Met Asp Gln Val Glu
    450                 455                 460
Asn His Glu Phe Leu Val Lys Pro Ser Phe Asp Pro Asn Leu Ser Glu
465                 470                 475                 480
Leu Arg Glu Ile Met Asn Asp Leu Glu Lys Lys Met Gln Ser Thr Leu
                485                 490                 495
Ile Ser Ala Ala Arg Asp Leu Gly Leu Asp Pro Gly Lys Gln Ile Lys
            500                 505                 510
```

```
Leu Asp Ser Ser Ala Gln Phe Gly Tyr Tyr Phe Arg Val Thr Cys Lys
            515                 520                 525

Glu Glu Lys Val Leu Arg Asn Asn Lys Asn Phe Ser Thr Val Asp Ile
530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Ala Gln Asp Ala
            565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
            595                 600                 605

Ala His Val Ser Asn Gly Ala Pro Val Pro Tyr Val Arg Pro Ala Ile
            610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
            645                 650                 655

Phe Glu Lys Asp Lys Gln Met Phe His Ile Ile Thr Gly Pro Asn Met
            660                 665                 670

Gly Gly Lys Ser Thr Tyr Ile Arg Gln Thr Gly Val Ile Val Leu Met
            675                 680                 685

Ala Gln Ile Gly Cys Phe Val Pro Cys Glu Ser Ala Glu Val Ser Ile
            690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
            725                 730                 735

Arg Ser Ala Thr Lys Asp Ser Leu Ile Ile Ile Asp Glu Leu Gly Arg
            740                 745                 750

Gly Thr Ser Thr Tyr Asp Gly Phe Gly Leu Ala Trp Ala Ile Ser Glu
            755                 760                 765

Tyr Ile Ala Thr Lys Ile Gly Ala Phe Cys Met Phe Ala Thr His Phe
770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
            805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
            835                 840                 845

Leu Glu Leu Glu Glu Phe Gln Tyr Ile Gly Glu Ser Gln Gly Tyr Asp
850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
            885                 890                 895

Thr Glu Met Ser Glu Glu Asn Ile Thr Ile Lys Leu Lys Gln Leu Lys
            900                 905                 910
```

```
          Ala Glu Val Ile Ala Lys Asn Asn Ser Phe Val Asn Glu Ile Ile Ser
                  915                 920                 925

Arg Ile Lys Val Thr Thr
              930

<210> SEQ ID NO 8
<211> LENGTH: 3145
<212> TYPE: DNA
<213> ORGANISM: Homo sapiens

<400> SEQUENCE: 8
ggcgggaaac agcttagtgg gtgtggggtc gcgcattttc ttcaaccagg aggtgaggag         60
gtttcgacat ggcggtgcag ccgaaggaga cgctgcagtt ggagagcgcg gccgaggtcg        120
gcttcgtgcg cttctttcag ggcatgccgg agaagccgac caccacagtg cgccttttcg        180 accgggcga cttctatacg gcgcacggcg aggacgcgct gctggccgcc cgggaggtgt         240
tcaagaccca gggggtgatc aagtacatgg ggccggcagg agcaaagaat ctgcagagtg        300
ttgtgcttag taaatgaat tttgaatctt ttgtaaaaga tcttcttctg gttcgtcagt         360
atagagttga agtttataag aatagagctg aaataaggc atccaaggag aatgattggt         420
atttggcata taaggcttct cctggcaatc tctctcagtt tgaagacatt ctctttggta        480
acaatgatat gtcagcttcc attggtgttg tgggtgttaa aatgtccgca gttgatggcc        540
agagacaggt tggagttggg tatgtggatt ccatacagag gaaactagga ctgtgtgaat        600
tccctgataa tgatcagttc tccaatcttg aggctctcct catccagatt ggaccaaagg        660
aatgtgtttt acccggagga gagactgctg agacatggg gaaactgaga cagataattc         720
aaagaggagg aattctgatc acagaaagaa aaaagctga cttttccaca aaagacattt         780
atcaggacct caaccggttg ttgaaaggca aaagggaga gcagatgaat agtgctgtat         840
tgccagaaat ggagaatcag gttgcagttt catcactgtc tgcggtaatc aagtttttag        900
aactcttatc agatgattcc aactttggac agtttgaact gactactttt gacttcagcc        960
agtatatgaa attggatatt gcagcagtca gagcccttaa cctttttcag ggttctgttg       1020
aagataccac tggctctcag tctctggctg ccttgctgaa taagtgtaaa accccctcaag      1080 gacaaagact tgttaaccag tggattaagc agcctctcat ggataagaac agaatagagg       1140
agagattgaa tttagtggaa gcttttgtag aagatgcaga attgaggcag actttacaag       1200
aagatttact tcgtcgattc ccagatctta accgacttgc caagaagttt caaagacaag       1260
cagcaaactt acaagattgt taccgactct atcagggtat aaatcaacta cctaatgtta       1320
tacaggctct ggaaaaacat gaaggaaaac accagaaatt attgttggca gtttttgtga       1380
ctcctcttac tgatcttcgt tctgacttct ccaagtttca ggaaatgata gaaacaactt       1440
tagatatgga tcaggtggaa aaccatgaat tccttgtaaa accttcattt gatcctaatc       1500
tcagtgaatt aagagaaata atgaatgact ggaaaagaa gatgcagtca acattaataa        1560
gtgcagccag agatcttggc ttggaccctg gcaaacagat taaactggat tccagtgcac       1620
agtttggata ttactttcgt gtaacctgta aggaagaaaa agtccttcgt aacaataaaa       1680
actttagtac tgtagatatc cagaagaatg gtgttaaatt taccaacagc aaattgactt       1740 cttttaaatga agagtatacc aaaaataaaa cagaatatga gaagcccag gatgccattg        1800 ttaaagaaat tgtcaatatt tcttcaggct atgtagaacc aatgcagaca ctcaatgatg       1860
tgttagctca gctagatgct gttgtcagct tgctcacgt gtcaaatgga gcacctgttc        1920
catatgtacg accagccatt ttggagaaag gacaaggaag aattatatta aaagcatcca       1980
```

-continued

```
ggcatgcttg tgttgaagtt caagatgaaa ttgcatttat tcctaatgac gtatactttg    2040
aaaaagataa acagatgttc cacatcatta ctggccccaa tgggaggt aaatcaacat      2100 atattcgaca aactggggtg atagtactca tggcccaaat tgggtgtttt gtgccatgtg    2160
agtcagcaga agtgtccatt gtggactgca tcttagcccg agtaggggct ggtgacagtc    2220
aattgaaagg agtctccacg ttcatggctg aaatgttgga aactgcttct atcctcaggt    2280
ctgcaaccaa agattcatta ataatcatag atgaattggg aagaggaact tctacctacg    2340
atggatttgg gttagcatgg gctatatcag aatacattgc aacaaagatt ggtgcttttt    2400
gcatgtttgc aacccatttt catgaactta ctgccttggc caatcagata ccaactgtta    2460
ataatctaca tgtcacagca ctcaccactg aagagacctt aactatgctt tatcaggtga    2520
agaaaggtgt ctgtgatcaa gttttggga ttcatgttgc agagcttgct aatttcccta     2580
agcatgtaat agagtgtgct aaacagaaag ccctggaact tgaggagttt cagtatattg    2640
gagaatcgca aggatatgat atcatggaac agcagcaaa gaagtgctat ctggaaagag     2700
agcaaggtga aaaaattatt caggagttcc tgtccaaggt gaaacaaatg cccttactg     2760 aaatgtcaga gaaaacatc acaataaagt taaacagct aaaagctgaa gtaatagcaa      2820
agaataatag ctttgtaaat gaaatcattt cacgaataaa agttactacg tgaaaaatcc    2880
cagtaatgga atgaaggtaa tattgataag ctattgtctg taatagtttt atattgtttt    2940
atattaaccc ttttccata gtgttaactg tcagtgccca tgggctatca acttaataag    3000
atatttagta atattttact ttgaggacat tttcaaagat ttttatttg aaaaatgaga     3060 gctgtaactg aggactgttt gcaattgaca taggcaataa taagtgatgt gctgaatttt    3120
ataaataaaa tcatgtagtt tgtgg                                           3145
```

<210> SEQ ID NO 9
<211> LENGTH: 756
<212> TYPE: PRT
<213> ORGANISM: Homo sapiens

<400> SEQUENCE: 9

| Met | Ser | Phe | Val | Ala | Gly | Val | Ile | Arg | Arg | Leu | Asp | Glu | Thr | Val | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

-continued

```
Thr Arg Arg Lys Ala Leu Lys Asn Pro Ser Glu Glu Tyr Gly Lys Ile
                165                 170                 175
Leu Glu Val Val Gly Arg Tyr Ser Val His Asn Ala Gly Ile Ser Phe
            180                 185                 190
Ser Val Lys Lys Gln Gly Glu Thr Val Ala Asp Val Arg Thr Leu Pro
        195                 200                 205
Asn Ala Ser Thr Val Asp Asn Ile Arg Ser Ile Phe Gly Asn Ala Val
    210                 215                 220
Ser Arg Glu Leu Ile Glu Ile Gly Cys Glu Asp Lys Thr Leu Ala Phe
225                 230                 235                 240
Lys Met Asn Gly Tyr Ile Ser Asn Ala Asn Tyr Ser Val Lys Lys Cys
                245                 250                 255
Ile Phe Leu Leu Phe Ile Asn His Arg Leu Val Glu Ser Thr Ser Leu
            260                 265                 270
Arg Lys Ala Ile Glu Thr Val Tyr Ala Ala Tyr Leu Pro Lys Asn Thr
        275                 280                 285
His Pro Phe Leu Tyr Leu Ser Leu Glu Ile Ser Pro Gln Asn Val Asp
    290                 295                 300
Val Asn Val His Pro Thr Lys His Glu Val His Phe Leu His Glu Glu
305                 310                 315                 320
Ser Ile Leu Glu Arg Val Gln Gln His Ile Glu Ser Lys Leu Leu Gly
                325                 330                 335
Ser Asn Ser Ser Arg Met Tyr Phe Thr Gln Thr Leu Leu Pro Gly Leu
            340                 345                 350
Ala Gly Pro Ser Gly Glu Met Val Lys Ser Thr Thr Ser Leu Thr Ser
        355                 360                 365
Ser Ser Thr Ser Gly Ser Ser Asp Lys Val Tyr Ala His Gln Met Val
    370                 375                 380
Arg Thr Asp Ser Arg Glu Gln Lys Leu Asp Ala Phe Leu Gln Pro Leu
385                 390                 395                 400
Ser Lys Pro Leu Ser Ser Gln Pro Gln Ala Ile Val Thr Glu Asp Lys
                405                 410                 415
Thr Asp Ile Ser Ser Gly Arg Ala Arg Gln Gln Asp Glu Glu Met Leu
            420                 425                 430
Glu Leu Pro Ala Pro Ala Glu Val Ala Ala Lys Asn Gln Ser Leu Glu
        435                 440                 445
Gly Asp Thr Thr Lys Gly Thr Ser Glu Met Ser Glu Lys Arg Gly Pro
    450                 455                 460
Thr Ser Ser Asn Pro Arg Lys Arg His Arg Glu Asp Ser Asp Val Glu
465                 470                 475                 480
Met Val Glu Asp Asp Ser Arg Lys Glu Met Thr Ala Ala Cys Thr Pro
                485                 490                 495
Arg Arg Arg Ile Ile Asn Leu Thr Ser Val Leu Ser Leu Gln Glu Glu
            500                 505                 510
Ile Asn Glu Gln Gly His Glu Val Leu Arg Glu Met Leu His Asn His
        515                 520                 525
Ser Phe Val Gly Cys Val Asn Pro Gln Trp Ala Leu Ala Gln His Gln
    530                 535                 540
Thr Lys Leu Tyr Leu Leu Asn Thr Thr Lys Leu Ser Glu Glu Leu Phe
545                 550                 555                 560
Tyr Gln Ile Leu Ile Tyr Asp Phe Ala Asn Phe Gly Val Leu Arg Leu
                565                 570                 575
```

```
Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
        595                 600                 605

Glu Tyr Ile Val Glu Phe Leu Lys Lys Ala Glu Met Leu Ala Asp
    610                 615                 620

Tyr Phe Ser Leu Glu Ile Asp Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
        755

<210> SEQ ID NO 10
<211> LENGTH: 2484
<212> TYPE: DNA
<213> ORGANISM: Homo sapiens

<400> SEQUENCE: 10
cttggctctt ctggcgccaa aatgtcgttc gtggcagggg ttattcggcg gctggacgag     60
acagtggtga accgcatcgc ggcgggggaa gttatccagc ggccagctaa tgctatcaaa    120
gagatgattg agaactgttt agatgcaaaa tccacaagta ttcaagtgat tgttaaagag    180
ggaggcctga gttgattca gatccaagac aatggcaccg ggatcaggaa agaagatctg    240
gatattgtat gtgaaaggtt cactactagt aaactgcagt cctttgagga tttagccagt    300
atttctacct atggctttcg aggtgaggct ttggccagca taagccatgt ggctcatgtt    360
actattacaa cgaaaacagc tgatggaaag tgtgcataca gagcaagtta ctcagatgga    420
aaactgaaag cccctcctaa accatgtgct ggcaatcaag ggacccagat cacggtggag    480 gaccttttt acaacatagc cacgaggaga aagctttaa aaaatccaag tgaagaatat    540 ggaaaattt tggaagttgt tggcaggtat tcagtacaca atgcaggcat tagtttctca    600
gttaaaaaac aaggagagac agtagctgat gttaggacac tacccaatgc ctcaaccgtg    660
gacaatattc gctccatctt tggaaatgct gttagtcgag aactgataga aattggatgt    720
gaggataaaa ccctagcctt caaaatgaat ggttacatat ccaatgcaaa ctactcagtg    780
aagaagtgca tcttcttact cttcatcaac catcgtctgg tagaatcaac ttccttgaga    840
aaagccatag aaacagtgta tgcagcctat ttgcccaaaa acacacaccc attcctgtac    900
ctcagtttag aaatcagtcc ccagaatgtg gatgttaatg tgcaccccac aaagcatgaa    960
gttcacttcc tgcacgagga gagcatcctg gagcgggtgc agcagcacat cgagagcaag   1020
ctcctgggct ccaattcctc caggatgtac ttcacccaga cttttgctacc aggacttgct   1080
```

-continued

```
ggcccctctg gggagatggt taaatccaca acaagtctga cctcgtcttc tacttctgga    1140
agtagtgata aggtctatgc ccaccagatg gttcgtacag attcccggga acagaagctt    1200
gatgcatttc tgcagcctct gagcaaaccc ctgtccagtc agccccaggc cattgtcaca    1260
gaggataaga cagatatttc tagtggcagg gctaggcagc aagatgagga gatgcttgaa    1320
ctcccagccc ctgctgaagt ggctgccaaa aatcagagct tggaggggga tacaacaaag    1380
gggacttcag aaatgtcaga agagagagga cctacttcca gcaaccccag aaagagacat    1440
cgggaagatt ctgatgtgga aatggtggaa gatgattccc gaaaggaaat gactgcagct    1500 tgtaccccc ggagaaggat cattaacctc actagtgttt tgagtctcca ggaagaaatt    1560
aatgagcagg gacatgaggt tctccgggag atgttgcata accactcctt cgtgggctgt    1620
gtgaatcctc agtgggcctt ggcacagcat caaaccaagt tataccttct caacaccacc    1680
aagcttagtg aagaactgtt ctaccagata tcatttatg attttgccaa ttttggtgtt    1740
ctcaggttat cggagccagc accgctcttt gaccttgcca tgcttgcctt agatagtcca    1800
gagagtggct ggacagagga agatggtccc aaagaaggac ttgctgaata cattgttgag    1860
tttctgaaga agaaggctga gatgcttgca gactatttct cttttggaaat tgatgaggaa    1920 gggaacctga ttggattacc ccttctgatt gacaactatg tgccccttt ggagggactg    1980 cctatcttca ttcttcgact agccactgag gtgaattggg acgaagaaaa ggaatgtttt    2040
gaaagcctca gtaaagaatg cgctatgttc tattccatcc ggaagcagta catatctgag    2100
gagtcgaccc tctcaggcca gcagagtgaa gtgcctggct ccattccaaa ctcctggaag    2160
tggactgtgg aacacattgt ctataaagcc ttgcgctcac acattctgcc tcctaaacat    2220
ttcacagaag atggaaatat cctgcagctt gctaacctgc ctgatctata caaagtcttt    2280
gagaggtgtt aaatatggtt atttatgcac tgtgggatgt gttcttcttt ctctgtattc    2340
cgatacaaag tgttgtatca aagtgtgata tacaaagtga ccaacataa gtgttggtag    2400 cacttaagac ttatacttgc cttctgatag tattcccttta tacacagtgg attgattata    2460
aataaataga tgtgtcttaa cata    2484
```

```
<210> SEQ ID NO 11
<211> LENGTH: 133
<212> TYPE: PRT
<213> ORGANISM: Homo sapiens

<400> SEQUENCE: 11

Met Lys Gln Leu Pro Ala Ala Thr Val Arg Leu Leu Ser Ser Gln
1               5                   10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
    50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95

Leu Gly Ser Ile Cys Cys Ile Ala Glu Val Leu Ile Thr Thr Arg Thr
            100                 105                 110
```

Ala Ala Asp Asn Phe Ser Thr Gln Tyr Val Leu Asp Gly Ser Gly His
        115                 120                 125

Ile Leu Ser Gln Lys
    130

<210> SEQ ID NO 12
<211> LENGTH: 426
<212> TYPE: DNA
<213> ORGANISM: Homo sapiens

<400> SEQUENCE: 12
cgaggcggat cgggtgttgc atccatggag cgagctgaga gctcgagtac agaacctgct    60
aaggccatca aacctattga tcggaagtca gtccatcaga tttgctctgg gcaggtggta   120
ctgagtctaa gcactgcggt aaaggagtta gtagaaaaca gtctggatgc tggtgccact   180
aatattgatc taaagcttaa ggactatgga gtggatctta ttgaagtttc agacaatgga   240 tgtgggtag aagaagaaaa cttcgaaggc ttaactctga acatcacac atctaagatt    300 caagagtttg ccgacctaac tcaggttgaa acttttggct ttcgggggga agctctgagc   360
tcactttgtg cactgagcga tgtcaccatt tctacctgcc acgcatcggc gaaggttgga   420
acttga                                                             426

<210> SEQ ID NO 13
<211> LENGTH: 100
<212> TYPE: DNA
<213> ORGANISM: Artificial Sequence
<220> FEATURE:
<223> OTHER INFORMATION: Oligonucleotide Primer

<400> SEQUENCE: 13
ttcagagtag aaaactaaat atgatgaata actaaaaata atttctcaaa ttttttttctg   60 atggttcctt ctgcttcatc cccgtggccc gttgctcgcg                         100

<210> SEQ ID NO 14
<211> LENGTH: 100
<212> TYPE: DNA
<213> ORGANISM: Artificial Sequence
<220> FEATURE:
<223> OTHER INFORMATION: Oligonucleotide Primer

<400> SEQUENCE: 14
gccccagttg gaccctgagg tcgtactcac cccaacagct cagcgccccc tctccagcgc    60
cgccataagc tacccagctt ctagagatct gacggttcac                         100

<210> SEQ ID NO 15
<211> LENGTH: 100
<212> TYPE: DNA
<213> ORGANISM: Artificial Sequence
<220> FEATURE:
<223> OTHER INFORMATION: Oligonucleotide Primer

<400> SEQUENCE: 15
tgtgtgtgtg ttgtggtcag tggggctgga ataaaagtag aatagacctg cacctgctgt    60
ggcatccatt ctgcttcatc cccgtggccc gttgctcgcg                         100

<210> SEQ ID NO 16
<211> LENGTH: 100
<212> TYPE: DNA
<213> ORGANISM: Artificial Sequence
<220> FEATURE:
<223> OTHER INFORMATION: Oligonucleotide Primer

<400> SEQUENCE: 16
tcaggagtca ggtgcaccat ggtgtctgtt tgaggttgct agtgaacaca gttgtgtcag    60
aagcaaatgt tacccagctt ctagagatct gacggttcac                        100

<210> SEQ ID NO 17
<211> LENGTH: 100
<212> TYPE: DNA
<213> ORGANISM: Artificial Sequence
<220> FEATURE:
<223> OTHER INFORMATION: Oligonucleotide Primer

<400> SEQUENCE: 17
gttctctgga cgtaattttt cttgagcaga gcaacagtag agctttgtat gcaacaatgt    60
aatttttaca ctgcttcatc cccgtggccc gttgctcgcg                        100

<210> SEQ ID NO 18
<211> LENGTH: 100
<212> TYPE: DNA
<213> ORGANISM: Artificial Sequence
<220> FEATURE:
<223> OTHER INFORMATION: Oligonucleotide Primer

<400> SEQUENCE: 18
atcaggtcca aaggacttaa ctgatctttc tcttctaata gctgatcttc agatgatcag    60
aacaatgtgc tacccagctt ctagagatct gacggttcac                        100

<210> SEQ ID NO 19
<211> LENGTH: 100
<212> TYPE: DNA
<213> ORGANISM: Artificial Sequence
<220> FEATURE:
<223> OTHER INFORMATION: Oligonucleotide Primer

<400> SEQUENCE: 19
tggcaggagc ggaagcaaga gagggaaggg aggaggtgcc acacactttc aaacaaccag    60
atcttcagac ctgcttcatc cccgtggccc gttgctcgcg                        100

<210> SEQ ID NO 20
<211> LENGTH: 100
<212> TYPE: DNA
<213> ORGANISM: Artificial Sequence
<220> FEATURE:
<223> OTHER INFORMATION: Oligonucleotide Primer

<400> SEQUENCE: 20
gctcggctga atccgcgcc ccttagaagt cacggtgcgc gagcagagac tggacggatt    60
ctagcgggat tacccagctt ctagagatct gacggttcac                        100

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 21
cagatctcta gaagctgggt                                               20

<210> SEQ ID NO 22
<211> LENGTH: 25
<212> TYPE: DNA
<213> ORGANISM: Artificial Sequence

```
<220> FEATURE:
<223> OTHER INFORMATION: Oligonucleotide Primer

<400> SEQUENCE: 22
atgactgagt acaaactggt ggtgg                                  25

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 23
cattcggtac tggcgtattt ctc                                    23

<210> SEQ ID NO 24
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 24
atggtgcacc tgactcctga ggag                                   24

<210> SEQ ID NO 25
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 25
gttggactta gggaacaaag gaac                                   24

<210> SEQ ID NO 26
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 26
atgctggtga gcatcttcac cctg                                   24

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 27
ctgaagagga aggaagccgg cgtc                                   24

<210> SEQ ID NO 28
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 28
atgaaatata caagttatat cttggc                                 26
```

<210> SEQ ID NO 29
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 29
caggacaacc attactggga tgc    23

<210> SEQ ID NO 30
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 30
atgaaaaagc tgaactcac cgcgacgtct    30

<210> SEQ ID NO 31
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 31
tttatataat tcatccatac catgtgtgtg    30

<210> SEQ ID NO 32
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 32
atgaaaaagc tgaactcac cgcgacgtct    30

<210> SEQ ID NO 33
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 33
caatttggac tttccgccct tcttggcctt    30

<210> SEQ ID NO 34
<211> LENGTH: 550
<212> TYPE: PRT
<213> ORGANISM: Photinus pyralis

<400> SEQUENCE: 34

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60
```

-continued

```
Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                 85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
            115                 120                 125

Ser Lys Lys Gly Leu Gln Lys Ile Leu Asn Val Gln Lys Lys Leu Pro
130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
            275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
            435                 440                 445

Val Ala Pro Ala Glu Leu Glu Ser Ile Leu Leu Gln His Pro Asn Ile
450                 455                 460

Phe Asp Ala Gly Val Ala Gly Leu Pro Asp Asp Asp Ala Gly Glu Leu
465                 470                 475                 480
```

| Pro | Ala | Ala | Val | Val | Val | Leu | Glu | His | Gly | Lys | Thr | Met | Thr | Glu | Lys |
|---|---|---|---|---|---|---|---|---|---|---|---|---|---|---|---|
| | | | | 485 | | | | | 490 | | | | | 495 | |

| Glu | Ile | Val | Asp | Tyr | Val | Ala | Ser | Gln | Val | Thr | Thr | Ala | Lys | Lys | Leu |
|---|---|---|---|---|---|---|---|---|---|---|---|---|---|---|---|
| | | | 500 | | | | | 505 | | | | | 510 | | |

| Arg | Gly | Gly | Val | Val | Phe | Val | Asp | Glu | Val | Pro | Lys | Gly | Leu | Thr | Gly |
|---|---|---|---|---|---|---|---|---|---|---|---|---|---|---|---|
| | | 515 | | | | | 520 | | | | | 525 | | | |

| Lys | Leu | Asp | Ala | Arg | Lys | Ile | Arg | Glu | Ile | Leu | Ile | Lys | Ala | Lys | Lys |
|---|---|---|---|---|---|---|---|---|---|---|---|---|---|---|---|
| | 530 | | | | | 535 | | | | | 540 | | | | |

| Gly | Gly | Lys | Ser | Lys | Leu |
|---|---|---|---|---|---|
| 545 | | | | 550 | |

<210> SEQ ID NO 35
<211> LENGTH: 2387
<212> TYPE: DNA
<213> ORGANISM: Photinus pyralis

<400> SEQUENCE: 35

```
ctgcagaaat aactaggtac taagcccgtt tgtgaaaagt ggccaaaccc ataaatttgg      60
caattacaat aaagaagcta aaattgtggt caaactcaca acatttttta ttatatacat     120
tttagtagct gatgcttata aaagcaatat ttaaatcgta acaacaaat aaaataaaat      180
ttaaacgatg tgattaagag ccaaaggtcc tctagaaaaa ggtatttaag caacggaatt     240
cctttgtgtt acattcttga atgtcgctcg cagtgacatt agcattccgg tactgttggt     300
aaaatggaag acgccaaaaa cataaagaaa ggcccggcgc cattctatcc tctagaggat     360
ggaaccgctg gagagcaact gcataaggct atgaagagat acgccctggt tcctggaaca     420
attgctttg tgagtatttc tgtctgattt ctttcgagtt aacgaaatgt tcttatgttt       480
ctttagacag atgcacatat cgaggtgaac atcacgtacg cggaatactt cgaaatgtcc      540
gttcggttgg cagaagctat gaacgatatg ggctgaata caaatcacag aatcgtcgta      600
tgcagtgaaa actctcttca attctttatg ccggtgttgg gcgcgttatt tatcggagtt      660
gcagttgcgc ccgcgaacga catttataat gaacgtaagc accctcgcca tcagaccaaa      720
gggaatgacg tatttaattt ttaaggtgaa ttgctcaaca gtatgaacat ttcgcagcct      780
accgtagtgt ttgttccaa aaggggttg caaaaaattt tgaacgtgca aaaaaaatta       840
ccaataatcc agaaaattat tatcatggat ctaaaacgg attaccaggg atttcagtcg      900
atgtacacgt tcgtcacatc tcatctacct cccggttta tgaatacga ttttgtacca       960
gagtcctttg atcgtgacaa acaattgca ctgataatga attcctctgg atctactggg     1020
ttacctaagg gtgtggccct tccgcataga actgcctgcg tcagattctc gcatgccagg    1080
tatgtcgtat aacaagagat taagtaatgt tgctacacac attgtagaga tcctattttt    1140
ggcaatcaaa tcattccgga tactgcgatt ttaagtgttg ttccattcca tcacggtttt    1200
ggaatgttta ctacactcgg atatttgata tgtggatttc gagtcgtctt aatgtataga    1260
tttgaagaag agctgttttt acgatccctt caggattaca aaattcaaag tgcgttgcta    1320
gtaccaaccc tattttcatt cttcgccaaa agcactctga ttgacaaata cgatttatct    1380
aatttacacg aaattgcttc tgggggcgca cctctttcga agaagtcgg ggaagcggtt     1440
gcaaaacggt gagttaagcg cattgctagt atttcaaggc tctaaaacgg cgcgtagctt    1500
ccatcttcca gggatacgac aaggatatgg gctcactgag actacatcag ctattctgat    1560
tacacccgag ggggatgata aaccgggcgc ggtcggtaaa gttgttccat tttttgaagc    1620
gaaggttgtg gatctggata ccgggaaaac gctgggcgtt aatcagagag gcgaattatg    1680
```

```
tgtcagagga cctatgatta tgtccggtta tgtaaacaat ccggaagcga ccaacgcctt    1740
gattgacaag gatggatggc tacattctgg agacatagct tactgggacg aagacgaaca    1800
cttcttcata gttgaccgct tgaagtcttt aattaaatac aaaggatatc aggtaatgaa    1860
gatttttaca tgcacacacg ctacaatacc tgtaggtggc ccccgctgaa ttggaatcga    1920
tattgttaca acaccccaac atcttcgacg cgggcgtggc aggtcttccc gacgatgacg    1980
ccggtgaact tcccgccgcc gttgttgttt tggagcacgg aaagacgatg acggaaaaag    2040
agatcgtgga ttacgtcgcc agtaaatgaa ttcgttttac gttactcgta ctacaattct    2100
tttcataggt caagtaacaa ccgcgaaaaa gttgcgcgga ggagttgtgt ttgtggacga    2160
agtaccgaaa ggtcttaccg gaaaactcga cgcaagaaaa atcagagaga tcctcataaa    2220
ggccaagaag ggcggaaagt ccaaattgta aaatgtaact gtattcagcg atgacgaaat    2280
tcttagctat tgtaatatta tatgcaaatt gatgaatggt aattttgtaa ttgtgggtca    2340
ctgtactatt ttaacgaata ataaaatcag gtataggtaa ctaaaaa                  2387
```

<210> SEQ ID NO 36
<211> LENGTH: 238
<212> TYPE: PRT
<213> ORGANISM: Aequorea victoria

<400> SEQUENCE: 36

Met Ser Lys Gly Glu Glu Leu Phe Thr Gly Val Val Pro Ile Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

Tyr Asn Ser His Asn Val Tyr Ile Met Ala Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220

Thr Ala Ala Gly Ile Thr His Gly Met Asp Glu Leu Tyr Lys
225                 230                 235

<210> SEQ ID NO 37
<211> LENGTH: 922
<212> TYPE: DNA
<213> ORGANISM: Aequorea victoria

<400> SEQUENCE: 37

```
tacacacgaa taaaagataa caaagatgag taaaggagaa gaacttttca ctggagttgt     60
cccaattctt gttgaattag atggcgatgt taatgggcaa aaattctctg tcagtggaga    120
gggtgaaggt gatgcaacat acggaaaact tacccttaaa tttatttgca ctactgggaa    180
gctacctgtt ccatggccaa cacttgtcac tactttctct tatggtgttc aatgcttttc    240
aagataccca gatcatatga acagcatga cttttttcaag agtgccatgc ccgaaggtta    300
tgtacaggaa agaactatat tttacaaaga tgacggaaac tacaagacac gtgctgaagt    360
caagtttgaa ggtgataccc ttgttaatag aatcgagtta aaaggtattg attttaaaga    420
agatggaaac attcttggac acaaaatgga atacaactat aactcacata atgtatacat    480
catggcagac aaaccaaaga tggaatcaa agttaacttc aaaattagac acaacattaa    540
agatggaagc gttcaattag cagaccatta tcaacaaaat actccaattg gcgatggccc    600
tgtcctttta ccagacaacc attacctgtc cacacaatct gccctttcca agatcccaa    660
cgaaaagaga gatcacatga tccttcttga gtttgtaaca gctgctggga ttacacatgg    720
catggatgaa ctatacaaat aaatgtccag acttccaatt gacactaaag tgtccgaaca    780
attactaaat tctcagggtt cctggttaaa ttcaggctga actttatttt atatatttat    840
agattcatta aaattttatg aataattat tgatgttatt aatagggct attttcttat    900
taaataggct actggagtgt at                                             922
```

<210> SEQ ID NO 38
<211> LENGTH: 311
<212> TYPE: PRT
<213> ORGANISM: Renilla reniformis

<400> SEQUENCE: 38

```
Met Thr Ser Lys Val Tyr Asp Pro Glu Gln Arg Lys Arg Met Ile Thr
1               5                  10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175
```

```
Glu Asn Asn Phe Phe Val Glu Thr Met Leu Pro Ser Lys Ile Met Arg
                180                 185                 190

Lys Leu Glu Pro Glu Glu Phe Ala Ala Tyr Leu Glu Pro Phe Lys Glu
            195                 200                 205

Lys Gly Glu Val Arg Arg Pro Thr Leu Ser Trp Pro Arg Glu Ile Pro
        210                 215                 220

Leu Val Lys Gly Gly Lys Pro Asp Val Val Gln Ile Val Arg Asn Tyr
225                 230                 235                 240

Asn Ala Tyr Leu Arg Ala Ser Asp Asp Leu Pro Lys Met Phe Ile Glu
                245                 250                 255

Ser Asp Pro Gly Phe Phe Ser Asn Ala Ile Val Glu Gly Ala Lys Lys
            260                 265                 270

Phe Pro Asn Thr Glu Phe Val Lys Val Lys Gly Leu His Phe Ser Gln
        275                 280                 285

Glu Asp Ala Pro Asp Glu Met Gly Lys Tyr Ile Lys Ser Phe Val Glu
    290                 295                 300

Arg Val Leu Lys Asn Glu Gln
305                 310

<210> SEQ ID NO 39
<211> LENGTH: 1196
<212> TYPE: DNA
<213> ORGANISM: Renilla reniformis

<400> SEQUENCE: 39
agcttaaaga tgacttcgaa agtttatgat ccagaacaaa ggaaacggat gataactggt      60
ccgcagtggt gggccagatg taaacaaatg aatgttcttg attcatttat taattattat     120
gattcagaaa acatgcaga aaatgctgtt attttttttac atggtaacgc ggcctcttct     180
tatttatggc gacatgttgt gccacatatt gagccagtag cgcggtgtat tataccagat     240
cttattggta tgggcaaatc aggcaaatct ggtaatggtt cttataggtt acttgatcat     300
tacaaatatc ttactgcatg gtttgaactt cttaatttac caaagaagat cattttttgtc    360 ggccatgatt ggggtgcttg tttggcattt cattatagct atgagcatca agataagatc     420
aaagcaatag ttcacgctga agtgtagta gatgtgattg aatcatggga tgaatggcct     480
gatattgaag aagatattgc gttgatcaaa tctgaagaag agaaaaaat ggttttggag      540 aataacttct tcgtggaaac catgttgcca tcaaaaatca tgagaaagtt agaaccagaa     600
gaatttgcag catatcttga accattcaaa gagaaaggtg aagttcgtcg tccaacatta     660
tcatggcctc gtgaaatccc gttagtaaaa ggtggtaaac ctgacgttgt acaaattgtt     720
aggaattata atgcttatct acgtgcaagt gatgatttac aaaaatgtt tattgaatcg      780 gatccaggat tctttttccaa tgctattgtt gaaggcgcca agaagttttcc taatactgaa    840 tttgtcaaag taaaaggtct tcattttcg caagaagatg cacctgatga atgggaaaa      900 tatatcaaat cgttcgttga gcgagttctc aaaaatgaac aataattact ttggttttt      960 atttacattt ttcccgggtt taataatata aatgtcattt tcaacaattt tatttttaact    1020 gaatatttca cagggaacat tcatatatgt tgattaattt agctcgaact ttactctgtc    1080
atatcatttt ggaatattac ctcttttcaat gaaactttat aaacagtggt tcaattaatt    1140
aatatatatt ataattacat ttgttatgta ataaactcgg ttttattata aaaaaa         1196
```

<210> SEQ ID NO 40
<211> LENGTH: 1360
<212> TYPE: PRT
<213> ORGANISM: Homo sapiens

<400> SEQUENCE: 40

```
Met Ser Arg Gln Ser Thr Leu Tyr Ser Phe Pro Lys Ser Pro Ala
1               5                   10                  15

Leu Ser Asp Ala Asn Lys Ala Ser Ala Arg Ala Ser Arg Glu Gly Gly
            20                  25                  30

Arg Ala Ala Ala Pro Gly Ala Ser Pro Ser Pro Gly Gly Asp Ala
        35                  40                      45

Ala Trp Ser Glu Ala Gly Pro Gly Pro Arg Pro Leu Ala Arg Ser Ala
50                  55                  60

Ser Pro Pro Lys Ala Lys Asn Leu Asn Gly Leu Arg Arg Ser Val
65                  70                  75                  80

Ala Pro Ala Ala Pro Thr Ser Cys Asp Phe Ser Pro Gly Asp Leu Val
                85                  90                  95

Trp Ala Lys Met Glu Gly Tyr Pro Trp Trp Pro Cys Leu Val Tyr Asn
                100                 105                 110

His Pro Phe Asp Gly Thr Phe Ile Arg Glu Lys Gly Lys Ser Val Arg
            115                 120                 125

Val His Val Gln Phe Phe Asp Asp Ser Pro Thr Arg Gly Trp Val Ser
    130                 135                 140

Lys Arg Leu Leu Lys Pro Tyr Thr Gly Ser Lys Ser Lys Glu Ala Gln
145                 150                 155                 160

Lys Gly Gly His Phe Tyr Ser Ala Lys Pro Glu Ile Leu Arg Ala Met
                165                 170                 175

Gln Arg Ala Asp Glu Ala Leu Asn Lys Asp Lys Ile Lys Arg Leu Glu
            180                 185                 190

Leu Ala Val Cys Asp Glu Pro Ser Glu Pro Glu Glu Glu Glu Met
            195                 200                 205

Glu Val Gly Thr Thr Tyr Val Thr Asp Lys Ser Glu Glu Asp Asn Glu
    210                 215                 220

Ile Glu Ser Glu Glu Glu Val Gln Pro Lys Thr Gln Gly Ser Arg Arg
225                 230                 235                 240

Ser Ser Arg Gln Ile Lys Lys Arg Arg Val Ile Ser Asp Ser Glu Ser
                245                 250                 255

Asp Ile Gly Gly Ser Asp Val Glu Phe Lys Pro Asp Thr Lys Glu Glu
            260                 265                 270

Gly Ser Ser Asp Glu Ile Ser Ser Gly Val Gly Asp Ser Glu Ser Glu
        275                 280                 285

Gly Leu Asn Ser Pro Val Lys Val Ala Arg Lys Arg Lys Met Val
        290                 295                 300

Thr Gly Asn Gly Ser Leu Lys Arg Lys Ser Arg Lys Glu Thr Pro
305                 310                 315                 320

Ser Ala Thr Lys Gln Ala Thr Ser Ile Ser Ser Glu Thr Lys Asn Thr
                325                 330                 335

Leu Arg Ala Phe Ser Ala Pro Gln Asn Ser Glu Ser Gln Ala His Val
            340                 345                 350

Ser Gly Gly Gly Asp Asp Ser Ser Arg Pro Thr Val Trp Tyr His Glu
        355                 360                 365

Thr Leu Glu Trp Leu Lys Glu Glu Lys Arg Arg Asp Glu His Arg Arg
370                 375                 380
```

```
Arg Pro Asp His Pro Asp Phe Asp Ala Ser Thr Leu Tyr Val Pro Glu
385                 390                 395                 400

Asp Phe Leu Asn Ser Cys Thr Pro Gly Met Arg Lys Trp Trp Gln Ile
            405                 410                 415

Lys Ser Gln Asn Phe Asp Leu Val Ile Cys Tyr Lys Val Gly Lys Phe
            420                 425                 430

Tyr Glu Leu Tyr His Met Asp Ala Leu Ile Gly Val Ser Glu Leu Gly
        435                 440                 445

Leu Val Phe Met Lys Gly Asn Trp Ala His Ser Gly Phe Pro Glu Ile
    450                 455                 460

Ala Phe Gly Arg Tyr Ser Asp Ser Leu Val Gln Lys Gly Tyr Lys Val
465                 470                 475                 480

Ala Arg Val Glu Gln Thr Glu Thr Pro Glu Met Met Glu Ala Arg Cys
                485                 490                 495

Arg Lys Met Ala His Ile Ser Lys Tyr Asp Arg Val Val Arg Arg Glu
                500                 505                 510

Ile Cys Arg Ile Ile Thr Lys Gly Thr Gln Thr Tyr Ser Val Leu Glu
            515                 520                 525

Gly Asp Pro Ser Glu Asn Tyr Ser Lys Tyr Leu Leu Ser Leu Lys Glu
        530                 535                 540

Lys Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
                565                 570                 575

Arg His Cys Ser Arg Phe Arg Thr Leu Val Ala His Tyr Pro Pro Val
                580                 585                 590

Gln Val Leu Phe Glu Lys Gly Asn Leu Ser Lys Glu Thr Lys Thr Ile
            595                 600                 605

Leu Lys Ser Ser Leu Ser Cys Ser Leu Gln Glu Gly Leu Ile Pro Gly
        610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
                645                 650                 655

Gln Val Leu Lys Gly Met Thr Ser Glu Ser Asp Ser Ile Gly Leu Thr
            660                 665                 670

Pro Gly Glu Lys Ser Glu Leu Ala Leu Ser Ala Leu Gly Gly Cys Val
        675                 680                 685

Phe Tyr Leu Lys Lys Cys Leu Ile Asp Gln Glu Leu Leu Ser Met Ala
    690                 695                 700

Asn Phe Glu Glu Tyr Ile Pro Leu Asp Ser Asp Thr Val Ser Thr Thr
705                 710                 715                 720

Arg Ser Gly Ala Ile Phe Thr Lys Ala Tyr Gln Arg Met Val Leu Asp
                725                 730                 735

Ala Val Thr Leu Asn Asn Leu Glu Ile Phe Leu Asn Gly Thr Asn Gly
            740                 745                 750

Ser Thr Glu Gly Thr Leu Leu Glu Arg Val Asp Thr Cys His Thr Pro
        755                 760                 765

Phe Gly Lys Arg Leu Leu Lys Gln Trp Leu Cys Ala Pro Leu Cys Asn
    770                 775                 780

His Tyr Ala Ile Asn Asp Arg Leu Asp Ala Ile Glu Asp Leu Met Val
785                 790                 795                 800
```

-continued

```
Val Pro Asp Lys Ile Ser Glu Val Val Glu Leu Leu Lys Lys Leu Pro
                805                 810                 815
Asp Leu Glu Arg Leu Leu Ser Lys Ile His Asn Val Gly Ser Pro Leu
                820                 825                 830
Lys Ser Gln Asn His Pro Asp Ser Arg Ala Ile Met Tyr Glu Glu Thr
                835                 840                 845
Thr Tyr Ser Lys Lys Lys Ile Ile Asp Phe Leu Ser Ala Leu Glu Gly
                850                 855                 860
Phe Lys Val Met Cys Lys Ile Gly Ile Met Glu Glu Val Ala Asp
865                 870                 875                 880
Gly Phe Lys Ser Lys Ile Leu Lys Gln Val Ile Ser Leu Gln Thr Lys
                885                 890                 895
Asn Pro Glu Gly Arg Phe Pro Asp Leu Thr Val Glu Leu Asn Arg Trp
                900                 905                 910
Asp Thr Ala Phe Asp His Glu Lys Ala Arg Lys Thr Gly Leu Ile Thr
                915                 920                 925
Pro Lys Ala Gly Phe Asp Ser Asp Tyr Asp Gln Ala Leu Ala Asp Ile
                930                 935                 940
Arg Glu Asn Glu Gln Ser Leu Leu Glu Tyr Leu Glu Lys Gln Arg Asn
945                 950                 955                 960
Arg Ile Gly Cys Arg Thr Ile Val Tyr Trp Gly Ile Gly Arg Asn Arg
                965                 970                 975
Tyr Gln Leu Glu Ile Pro Glu Asn Phe Thr Thr Arg Asn Leu Pro Glu
                980                 985                 990
Glu Tyr Glu Leu Lys Ser Thr Lys Lys Gly Cys Lys Arg Tyr Trp Thr
                995                 1000                1005
Lys Thr Ile Glu Lys Lys Leu Ala Asn Leu Ile Asn Ala Glu Glu
                1010                1015                1020
Arg Arg Asp Val Ser Leu Lys Asp Cys Met Arg Arg Leu Phe Tyr
                1025                1030                1035
Asn Phe Asp Lys Asn Tyr Lys Asp Trp Gln Ser Ala Val Glu Cys
                1040                1045                1050
Ile Ala Val Leu Asp Val Leu Leu Cys Leu Ala Asn Tyr Ser Arg
                1055                1060                1065
Gly Gly Asp Gly Pro Met Cys Arg Pro Val Ile Leu Leu Pro Glu
                1070                1075                1080
Asp Thr Pro Pro Phe Leu Glu Leu Lys Gly Ser Arg His Pro Cys
                1085                1090                1095
Ile Thr Lys Thr Phe Phe Gly Asp Asp Phe Ile Pro Asn Asp Ile
                1100                1105                1110
Leu Ile Gly Cys Glu Glu Glu Gln Glu Asn Gly Lys Ala Tyr
                1115                1120                1125
Cys Val Leu Val Thr Gly Pro Asn Met Gly Gly Lys Ser Thr Leu
                1130                1135                1140
Met Arg Gln Ala Gly Leu Leu Ala Val Met Ala Gln Met Gly Cys
                1145                1150                1155
Tyr Val Pro Ala Glu Val Cys Arg Leu Thr Pro Ile Asp Arg Val
                1160                1165                1170
Phe Thr Arg Leu Gly Ala Ser Asp Arg Ile Met Ser Gly Glu Ser
                1175                1180                1185
Thr Phe Phe Val Glu Leu Ser Glu Thr Ala Ser Ile Leu Met His
                1190                1195                1200
```

| | | | | | | | | | | |
|---|---|---|---|---|---|---|---|---|---|---|
| Ala | Thr | Ala | His | Ser | Leu | Val | Leu | Val | Asp | Glu | Leu | Gly | Arg | Gly |
| | 1205 | | | | 1210 | | | | 1215 | |

Thr Ala Thr Phe Asp Gly Thr Ala Ile Ala Asn Ala Val Val Lys
    1220              1225              1230

Glu Leu Ala Glu Thr Ile Lys Cys Arg Thr Leu Phe Ser Thr His
    1235              1240              1245

Tyr His Ser Leu Val Glu Asp Tyr Ser Gln Asn Val Ala Val Arg
    1250              1255              1260

Leu Gly His Met Ala Cys Met Val Glu Asn Glu Cys Glu Asp Pro
    1265              1270              1275

Ser Gln Glu Thr Ile Thr Phe Leu Tyr Lys Phe Ile Lys Gly Ala
    1280              1285              1290

Cys Pro Lys Ser Tyr Gly Phe Asn Ala Ala Arg Leu Ala Asn Leu
    1295              1300              1305

Pro Glu Glu Val Ile Gln Lys Gly His Arg Lys Ala Arg Glu Phe
    1310              1315              1320

Glu Lys Met Asn Gln Ser Leu Arg Leu Phe Arg Glu Val Cys Leu
    1325              1330              1335

Ala Ser Glu Arg Ser Thr Val Asp Ala Glu Ala Val His Lys Leu
    1340              1345              1350

Leu Thr Leu Ile Lys Glu Leu
    1355              1360

<210> SEQ ID NO 41
<211> LENGTH: 4264
<212> TYPE: DNA
<213> ORGANISM: Homo sapiens

<400> SEQUENCE: 41

```
atttcccgcc agcaggagcc gcgcggtaga tgcggtgctt ttaggagctc cgtccgacag      60
aacggttggg ccttgccggc tgtcggtatg tcgcgacaga gcaccctgta cagcttcttc     120
cccaagtctc cggcgctgag tgatgccaac aaggcctcgg ccagggcctc acgcgaaggc     180
ggccgtgccg ccgctgcccc cggggcctct ccttccccag gcggggatgc ggcctggagc     240
gaggctgggc ctgggcccag gcccttggcg cgatccgcgt caccgcccaa ggcgaagaac     300
ctcaacggag gctgcggag atcggtagcg cctgctgccc ccaccagttg tgacttctca     360
ccaggagatt tggtttgggc caagatggag ggttacccct ggtggccttg tctggtttac     420
aaccacccct tgatggaac attcatccgc gagaaaggga atcagtccg tgttcatgta      480
cagttttttg atgacagccc aacaaggggc tgggttagca aaaggctttt aaagccatat     540
acaggttcaa aatcaaagga agcccagaag ggaggtcatt tttacagtgc aaagcctgaa     600
atactgagag caatgcaacg tgcagatgaa gccttaaata agacaagat taagaggctt      660
gaattggcag tttgtgatga gccctcagag ccagaagagg aagaagagat ggaggtaggc     720
acaacttacg taacagataa gagtgaagaa gataatgaaa ttgagagtga agaggaagta     780
cagcctaaga cacaaggatc taggcgaagt agccgccaaa taaaaaaacg aagggtcata     840
tcagattctg agagtgacat tggtggctct gatgtgaatt taagccaga cactaaggag     900
gaaggaagca gtgatgaaat aagcagtgga gtggggata gtgagagtga aggcctgaac     960
agccctgtca agttgctcg aaagcggaag agaatggtga ctggaaatgg ctctcttaaa    1020
aggaaaagct ctaggaagga aacgccctca gccaccaaac aagcaactag catttcatca    1080
gaaaccaaga atactttgag agctttctct gcccctcaaa attctgaatc ccaagcccac    1140
```

-continued

```
gttagtggag gtggtgatga cagtagtcgc cctactgttt ggtatcatga aactttagaa    1200
tggcttaagg aggaaaagag aagagatgag cacaggagga ggcctgatca ccccgatttt    1260
gatgcatcta cactctatgt gcctgaggat ttcctcaatt cttgtactcc tgggatgagg    1320
aagtggtggc agattaagtc tcagaacttt gatcttgtca tctgttacaa ggtggggaaa    1380
ttttatgagc tgtaccacat ggatgctctt attggagtca gtgaactggg gctggtattc    1440
atgaaaggca actgggccca ttctggcttt cctgaaattg catttggccg ttattcagat    1500
tccctggtgc agaagggcta taaagtagca cgagtggaac agactgagac tccagaaatg    1560
atggaggcac gatgtagaaa gatggcacat atatccaagt atgatagagt ggtgaggagg    1620
gagatctgta ggatcattac caagggtaca cagacttaca gtgtgctgga aggtgatccc    1680
tctgagaact acagtaagta tcttcttagc ctcaaagaaa aagaggaaga ttcttctggc    1740
catactcgtg catatggtgt gtgctttgtt gatacttcac tgggaaagtt tttcataggt    1800
cagttttcag atgatcgcca ttgttcgaga tttaggactc tagtggcaca ctatccccca    1860
gtacaagttt tatttgaaaa aggaaatctc tcaaggaaaa ctaaaacaat tctaaagagt    1920
tcattgtcct gttctcttca ggaaggtctg atacccggct cccagttttg ggatgcatcc    1980
aaaactttga gaactctcct tgaggaagaa tattttaggg aaaagctaag tgatggcatt    2040
ggggtgatgt taccccaggt gcttaaaggt atgacttcag agtctgattc cattgggttg    2100
acaccaggag agaaaagtga attggccctc tctgctctag gtggttgtgt cttctacctc    2160
aaaaaatgcc ttattgatca ggagctttta tcaatggcta attttgaaga atatattccc    2220
ttggattctg acacagtcag cactacaaga tctggtgcta tcttcaccaa agcctatcaa    2280
cgaatggtgc tagatgcagt gacattaaac aacttggaga tttttctgaa tggaacaaat    2340
ggttctactg aaggaaccct actagagagg gttgatactt gccatactcc ttttggtaag    2400
cggctcctaa agcaatggct ttgtgcccca ctctgtaacc attatgctat taatgatcgt    2460
ctagatgcca tagaagacct catggttgtg cctgacaaaa tctccgaagt tgtagagctt    2520
ctaaagaagc ttccagatct tgagaggcta ctcagtaaaa ttcataatgt tgggtctccc    2580
ctgaagagtc agaaccaccc agacagcagg gctataatgt atgaagaaac tacatacagc    2640
aagaagaaga ttattgattt tctttctgct ctggaaggat tcaaagtaat gtgtaaaatt    2700
atagggatca tggaagaagt tgctgatggt tttaagtcta aaatccttaa gcaggtcatc    2760
tctctgcaga caaaaaatcc tgaaggtcgt tttcctgatt tgactgtaga attgaaccga    2820
tgggatacag cctttgacca tgaaaaggct cgaaagactg gacttattac tcccaaagca    2880
ggctttgact ctgattatga ccaagctctt gctgacataa gagaaaatga acagagcctc    2940
ctggaatacc tagagaaaca gcgcaacaga attggctgta ggaccatagt ctattggggg    3000
attggtagga accgttacca gctggaaatt cctgagaatt tcaccactcg caatttgcca    3060
gaagaatacg agttgaaatc taccaagaag ggctgtaaac gatactggac caaaactatt    3120
gaaaagaagt tggctaatct cataaatgct gaagaacgga gggatgtatc attgaaggac    3180
tgcatgcggc gactgttcta taactttgat aaaaattaca aggactggca gtctgctgta    3240
gagtgtatcg cagtgttgga tgttttactg tgcctggcta actatagtcg aggggtgat    3300
ggtcctatgt gtcgcccagt aattctgttc ccggaagata ccccccctt cttagagctt    3360
aaaggatcac gccatccttg cattacgaag acttttttttg gagatgattt tattcctaat    3420
gacattctaa taggctgtga ggaagaggag caggaaaatg gcaaagccta ttgtgtgctt    3480
gttactggac caaatatggg gggcaagtct acgcttatga gacaggctgg cttattagct    3540
```

-continued

```
gtaatggccc agatgggttg ttacgtccct gctgaagtgt gcaggctcac accaattgat    3600
agagtgttta ctagacttgg tgcctcagac agaataatgt caggtgaaag tacatttttt    3660
gttgaattaa gtgaaactgc cagcatactc atgcatgcaa cagcacattc tctggtgctt    3720
gtggatgaat taggaagagg tactgcaaca tttgatggga cggcaatagc aaatgcagtt    3780
gttaaagaac ttgctgagac tataaaatgt cgtacattat tttcaactca ctaccattca    3840
ttagtagaag attattctca aaatgttgct gtgcgcctag acatatggc atgcatggta     3900
gaaaatgaat gtgaagaccc cagccaggag actattacgt tcctctataa attcattaag    3960
ggagcttgtc ctaaaagcta tggctttaat gcagcaaggc ttgctaatct cccagaggaa    4020
gttattcaaa agggacatag aaaagcaaga gaatttgaga agatgaatca gtcactacga    4080
ttatttcggg aagtttgcct ggctagtgaa aggtcaactg tagatgctga agctgtccat    4140
aaattgctga ctttgattaa ggaattatag actgactaca ttggaagctt tgagttgact    4200
tctgaccaaa ggtggtaaat tcagacaaca ttatgatcta ataaactttta tttttaaaa    4260
atga                                                                  4264
```

<210> SEQ ID NO 42
<211> LENGTH: 389
<212> TYPE: PRT
<213> ORGANISM: Homo sapiens

<400> SEQUENCE: 42

```
Met Ala Gln Pro Lys Gln Glu Arg Val Ala Arg Ala Arg His Gln Arg
1               5                   10                  15

Ser Glu Thr Ala Arg His Gln Arg Ser Glu Thr Ala Lys Thr Pro Thr
            20                  25                  30

Leu Gly Asn Arg Gln Thr Pro Thr Leu Gly Asn Arg Gln Thr Pro Arg
        35                  40                  45

Leu Gly Ile His Ala Arg Pro Arg Arg Arg Ala Thr Thr Ser Leu Leu
    50                  55                  60

Thr Leu Leu Leu Ala Phe Gly Lys Asn Ala Val Arg Cys Ala Leu Ile
65                  70                  75                  80

Gly Pro Gly Ser Leu Thr Ser Arg Thr Arg Pro Leu Thr Glu Pro Leu
                85                  90                  95

Gly Glu Lys Glu Arg Arg Glu Val Phe Phe Pro Arg Pro Glu Arg
            100                 105                 110

Val Glu His Asn Val Glu Ser Ser Arg Trp Glu Pro Arg Arg Gly
        115                 120                 125

Ala Cys Gly Ser Arg Gly Gly Asn Phe Pro Ser Pro Arg Gly Gly Ser
    130                 135                 140

Gly Val Ala Ser Leu Glu Arg Ala Glu Asn Ser Ser Thr Glu Pro Ala
145                 150                 155                 160

Lys Ala Ile Lys Pro Ile Asp Arg Lys Ser Val His Gln Ile Cys Ser
                165                 170                 175

Gly Pro Val Val Pro Ser Leu Arg Pro Asn Ala Val Lys Glu Leu Val
            180                 185                 190

Glu Asn Ser Leu Asp Ala Gly Ala Thr Asn Val Asp Leu Lys Leu Lys
        195                 200                 205

Asp Tyr Gly Val Asp Leu Ile Glu Val Ser Gly Asn Gly Cys Gly Val
    210                 215                 220

Glu Glu Glu Asn Phe Glu Gly Phe Thr Leu Lys His Thr Cys Lys
225                 230                 235                 240
```

```
Ile Gln Glu Phe Ala Asp Leu Thr Gln Val Glu Thr Phe Gly Phe Arg
            245                 250                 255
Gly Glu Ala Leu Ser Ser Leu Cys Ala Leu Ser Asp Val Thr Ile Ser
        260                 265                 270
Thr Cys Arg Val Ser Ala Lys Val Gly Thr Arg Leu Val Phe Asp His
    275                 280                 285
Tyr Gly Lys Ile Ile Gln Lys Thr Pro Tyr Pro Arg Pro Arg Gly Met
290                 295                 300
Thr Val Ser Val Lys Gln Leu Phe Ser Thr Leu Pro Val His His Lys
305                 310                 315                 320
Glu Phe Gln Arg Asn Ile Lys Lys Lys Arg Ala Cys Phe Pro Phe Ala
                325                 330                 335
Phe Cys Arg Asp Cys Gln Phe Pro Glu Ala Ser Pro Ala Met Leu Pro
            340                 345                 350
Val Gln Pro Val Glu Leu Thr Pro Arg Ser Thr Pro Pro His Pro Cys
        355                 360                 365
Ser Leu Glu Asp Asn Val Ile Thr Val Phe Ser Val Lys Asn Gly
    370                 375                 380
Pro Gly Ser Ser Arg
385

<210> SEQ ID NO 43
<211> LENGTH: 1408
<212> TYPE: DNA
<213> ORGANISM: Homo sapiens

<400> SEQUENCE: 43
```

| | | | | | |
|---|---|---|---|---|---|
| ggcgctccta | cctgcaagtg | gctagtgcca | agtgctgggc | cgccgctcct | gccgtgcatg | 60 |
| ttggggagcc | agtacatgca | ggtgggctcc | acacggagag | gggcgcagac | ccggtgacag | 120 |
| ggctttacct | ggtacatcgg | catggcgcaa | ccaaagcaag | agagggtggc | gcgtgccaga | 180 |
| caccaacggt | cggaaaccgc | cagacaccaa | cggtcggaaa | ccgccaagac | caacgctc | 240 |
| ggaaaccgcc | agacaccaac | gctcggaaac | cgccagacac | caaggctcgg | aatccacgcc | 300 |
| aggccacgac | ggagggcgac | tacctcccct | ctgaccctgc | tgctggcgtt | cggaaaaaac | 360 |
| gcagtccggt | gtgctctgat | tggtccaggc | tctttgacgt | cacggactcg | acctttgaca | 420 |
| gagccactag | gcgaaaagga | gagacgggaa | gtattttttc | cgccccgccc | ggaaagggtg | 480 |
| gagcacaacg | tcgaaagcag | ccgttgggag | cccaggaggc | ggggcgcctg | tgggagccgt | 540 |
| ggagggaact | ttcccagtcc | ccgaggcgga | tccggtgttg | catccttgga | gcgagctgag | 600 |
| aactcgagta | cagaacctgc | taaggccatc | aaacctattg | atcggaagtc | agtccatcag | 660 |
| atttgctctg | ggccggtggt | accgagtcta | aggccgaatg | cggtgaagga | gttagtagaa | 720 |
| aacagtctgg | atgctggtgc | cactaatgtt | gatctaaagc | ttaaggacta | tggagtggat | 780 |
| ctcattgaag | tttcaggcaa | tggatgtggg | gtagaagaag | aaaacttcga | aggctttact | 840 |
| ctgaaacatc | acacatgtaa | gattcaagag | tttgccgacc | taactcaggt | ggaaactttt | 900 |
| ggctttcggg | gggaagctct | gagctcactt | tgtgcactga | gtgatgtcac | catttctacc | 960 |
| tgccgtgtat | cagcgaaggt | tgggactcga | ctggtgtttg | atcactatgg | gaaaatcatc | 1020 |
| cagaaaaccc | cctaccccg | ccccagaggg | atgacagtca | gcgtgaagca | gttatttct | 1080 |
| acgctacctg | tgcaccataa | agaatttcaa | aggaatatta | agaagaaacg | tgcctgcttc | 1140 |
| cccttcgcct | tctgccgtga | ttgtcagttt | cctgaggcct | ccccagccat | gcttcctgta | 1200 |
| cagcctgtag | aactgactcc | tagaagtacc | ccaccccacc | cctgctcctt | ggaggacaac | 1260 |

```
gtgatcactg tattcagctc tgtcaagaat ggtccaggtt cttctagatg atctgcacaa    1320
atggttcctc tcctccttcc tgatgtctgc cattagcatt ggaataaagt tcctgctgaa    1380
aatccaaaaa aaaaaaaaaa aaaaaaaa                                        1408
```

<210> SEQ ID NO 44
<211> LENGTH: 264
<212> TYPE: PRT
<213> ORGANISM: Homo sapiens

<400> SEQUENCE: 44

```
Met Cys Pro Trp Arg Pro Arg Leu Gly Arg Arg Cys Met Val Ser Pro
1               5                   10                  15

Arg Glu Ala Asp Leu Gly Pro Gln Lys Asp Thr Arg Leu Asp Leu Pro
            20                  25                  30

Arg Ser Pro Ala Arg Ala Pro Arg Glu Gln Asn Ser Leu Gly Glu Val
        35                  40                  45

Asp Arg Arg Gly Pro Arg Glu Gln Thr Arg Ala Pro Ala Thr Ala Ala
    50                  55                  60

Pro Pro Arg Pro Leu Gly Ser Arg Gly Ala Glu Ala Ala Glu Pro Gln
65                  70                  75                  80

Glu Gly Leu Ser Ala Thr Val Ser Ala Cys Phe Gln Glu Gln Gln Glu
                85                  90                  95

Met Asn Thr Leu Gln Gly Pro Val Ser Phe Lys Asp Val Ala Val Asp
            100                 105                 110

Phe Thr Gln Glu Glu Trp Arg Gln Leu Asp Pro Asp Glu Lys Ile Ala
        115                 120                 125

Tyr Gly Asp Val Met Leu Glu Asn Tyr Ser His Leu Val Ser Val Gly
    130                 135                 140

Tyr Asp Tyr His Gln Ala Lys His His Gly Val Glu Val Lys Glu
145                 150                 155                 160

Val Glu Gln Gly Glu Glu Pro Trp Ile Met Glu Gly Glu Phe Pro Cys
                165                 170                 175

Gln His Ser Pro Glu Pro Ala Lys Ala Ile Lys Pro Ile Asp Arg Lys
            180                 185                 190

Ser Val His Gln Ile Cys Ser Gly Pro Val Val Leu Ser Leu Ser Thr
        195                 200                 205

Ala Val Lys Glu Leu Val Glu Asn Ser Leu Asp Ala Gly Ala Thr Asn
    210                 215                 220

Ile Asp Leu Lys Leu Lys Asp Tyr Gly Val Asp Leu Ile Glu Val Ser
225                 230                 235                 240

Asp Asn Gly Cys Gly Val Glu Glu Asn Phe Glu Gly Leu Ile Ser
                245                 250                 255

Phe Ser Ser Glu Thr Ser His Met
            260
```

<210> SEQ ID NO 45
<211> LENGTH: 1785
<212> TYPE: DNA
<213> ORGANISM: Homo sapiens

<400> SEQUENCE: 45

```
tttttagaaa ctgatgttta ttttccatca accatttttc catgctgctt aagagaatat      60
gcaagaacag cttaagacca gtcagtggtt gctcctaccc attcagtggc ctgagcagtg     120
gggagctgca gaccagtctt ccgtggcagg ctgagcgctc cagtcttcag tagggaattg     180
```

-continued

```
ctgaataggc acagagggca cctgtacacc ttcagaccag tctgcaacct caggctgagt    240
agcagtgaac tcaggagcgg gagcagtcca ttcaccctga aattcctcct tggtcactgc    300
cttctcagca gcagcctgct cttcttttc aatctcttca ggatctctgt agaagtacag     360
atcaggcatg acctcccatg ggtgttcacg ggaaatggtg ccacgcatgc gcagaacttc    420
ccgagccagc atccaccaca ttaaacccac tgagtgagct cccttgttgt tgcatgggat    480
ggcaatgtcc acatagcgca gaggagaatc tgtgttacac agcgcaatgg taggtaggtt    540
aacataagat gcctccgtga gaggcgaagg ggcggcggga cccgggcctg cccgtatgt     600 gtccttggcg gcctagacta ggccgtcgct gtatggtgag ccccagggag gcggatctgg    660
gcccccagaa ggacacccgc ctggatttgc cccgtagccc ggcccgggcc cctcgggagc    720
agaacagcct tggtgaggtg gacaggaggg gacctcgcga gcagacgcgc gcgccagcga    780
cagcagcccc gccccggcct ctcgggagcc gggggggcaga ggctgcggag ccccaggagg    840
gtctatcagc cacagtctct gcatgtttcc aagagcaaca ggaaatgaac acattgcagg    900
ggccagtgtc attcaaagat gtggctgtgg atttcaccca ggaggagtgg cggcaactgg    960
accctgatga agatagca tacggggatg tgatgttgga gaactacagc catctagttt      1020
ctgtggggta tgattatcac caagccaaac atcatcatgg agtggaggtg aaggaagtgg    1080
agcagggaga ggagccgtgg ataatggaag gtgaatttcc atgtcaacat agtccagaac    1140
ctgctaaggc catcaaacct attgatcgga agtcagtcca tcagatttgc tctgggccag    1200
tggtactgag tctaagcact gcagtgaagg agttagtaga aaacagtctg gatgctggtg    1260
ccactaatat tgatctaaag cttaaggact atggagtgga tctcattgaa gtttcagaca    1320
atggatgtgg ggtagaagaa gaaaactttg aaggcttaat ctctttcagc tctgaaacat    1380
cacacatgta agattcaaga gtttgccgac ctaactgaag ttgaaacttt cggttttcag    1440
ggggaagctc tgagctcact gtgtgcactg agcgatgtca ccatttctac ctgccacgcg    1500
ttggtgaagg ttgggactcg actggtgttt gatcacgatg ggaaaatcat ccaggaaacc    1560
ccctaccccc accccagagg gaccacagtc agcgtgaagc agttattttc tacgctacct    1620
gtgcgccata aggaatttca aggaatatt aagaagacgt gcctgcttcc ccttcgcctt     1680
ctgccgtgat tgtcagtttc ctgaggcctc cccagccatg cttcctgtac agcctgcaga    1740
actgtgagtc aattaaacct cttttcttca taaattaaaa aaaaa                    1785
```

<210> SEQ ID NO 46
<211> LENGTH: 583
<212> TYPE: PRT
<213> ORGANISM: Artificial Sequence
<220> FEATURE:
<223> OTHER INFORMATION: Chimera: Hyg from Escherichia coli; GFP from Aequoria victoria

<400> SEQUENCE: 46

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80
```

-continued

```
Gly Glu Phe Ser Glu Ser Leu Thr Tyr Cys Ile Ser Arg Arg Ala Gln
                 85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Asp Arg Glu Met Gly Glu Ala Asn Met Ser Lys Gly Glu Glu Leu
            340                 345                 350

Phe Thr Gly Val Val Pro Ile Leu Val Glu Leu Asp Gly Asp Val His
        355                 360                 365

Gly His Lys Phe Ser Val Arg Gly Glu Gly Glu Gly Asp Ala Asp Tyr
    370                 375                 380

Gly Lys Leu Glu Ile Lys Phe Ile Cys Thr Thr Gly Lys Leu Pro Val
385                 390                 395                 400

Pro Trp Pro Thr Leu Val Thr Thr Leu Gly Tyr Gly Ile Leu Cys Phe
                405                 410                 415

Ala Arg Tyr Pro Glu His Met Lys Met Asn Asp Phe Phe Lys Ser Ala
            420                 425                 430

Met Pro Glu Gly Tyr Ile Gln Glu Arg Thr Ile Phe Phe Gln Asp Asp
        435                 440                 445

Gly Lys Tyr Lys Thr Arg Gly Glu Val Lys Phe Glu Gly Asp Thr Leu
    450                 455                 460

Val Asn Arg Ile Glu Leu Lys Gly Met Asp Phe Lys Glu Asp Gly Asn
465                 470                 475                 480

Ile Leu Gly His Lys Leu Glu Tyr Asn Phe Asn Ser His Asn Val Tyr
                485                 490                 495
```

-continued

```
Ile Met Pro Asp Lys Ala Asn Asn Gly Leu Lys Val Asn Phe Lys Ile
            500                 505                 510

Arg His Asn Ile Glu Gly Gly Val Gln Leu Ala Asp His Tyr Gln
            515                 520                 525

Thr Asn Val Pro Leu Gly Asp Gly Pro Val Leu Ile Pro Ile Asn His
            530                 535                 540

Tyr Leu Ser Thr Gln Thr Ala Ile Ser Lys Asp Arg Asn Glu Thr Arg
545                 550                 555                 560

Asp His Met Val Phe Leu Glu Phe Phe Ser Ala Cys Gly His Thr His
                565                 570                 575

Gly Met Asp Glu Leu Tyr Lys
            580

<210> SEQ ID NO 47
<211> LENGTH: 895
<212> TYPE: PRT
<213> ORGANISM: Artificial Sequence
<220> FEATURE:
<223> OTHER INFORMATION: Chimera: Luc from Photinus pyralis; HYG from
      Escherichia coli

<400> SEQUENCE: 47

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270
```

-continued

```
Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
        290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Asp Arg Glu Met Gly Glu Ala Asn Met Glu Asp Ala Lys Asn Ile
            340                 345                 350

Lys Lys Gly Pro Ala Pro Phe Tyr Pro Leu Glu Asp Gly Thr Ala Gly
        355                 360                 365

Glu Gln Leu His Lys Ala Met Lys Arg Tyr Ala Leu Val Pro Gly Thr
        370                 375                 380

Ile Ala Phe Thr Asp Ala His Ile Glu Val Asn Ile Thr Tyr Ala Glu
385                 390                 395                 400

Tyr Phe Glu Met Ser Val Arg Leu Ala Glu Ala Met Lys Arg Tyr Gly
                405                 410                 415

Leu Asn Thr Asn His Arg Ile Val Val Cys Ser Glu Asn Ser Leu Gln
            420                 425                 430

Phe Phe Met Pro Val Leu Gly Ala Leu Phe Ile Gly Val Ala Val Ala
        435                 440                 445

Pro Ala Asn Asp Ile Tyr Asn Glu Arg Glu Leu Leu Asn Ser Met Asn
450                 455                 460

Ile Ser Gln Pro Thr Val Val Phe Val Ser Lys Lys Gly Leu Gln Lys
465                 470                 475                 480

Ile Leu Asn Val Gln Lys Lys Leu Pro Ile Ile Gln Lys Ile Ile Ile
                485                 490                 495

Met Asp Ser Lys Thr Asp Tyr Gln Gly Phe Gln Ser Met Tyr Thr Phe
            500                 505                 510

Val Thr Ser His Leu Pro Pro Gly Phe Asn Glu Tyr Asp Phe Val Pro
        515                 520                 525

Glu Ser Phe Asp Arg Asp Lys Thr Ile Ala Leu Ile Met Asn Ser Ser
        530                 535                 540

Gly Ser Thr Gly Leu Pro Lys Gly Val Ala Leu Pro His Arg Thr Ala
545                 550                 555                 560

Cys Val Arg Phe Ser His Ala Arg Asp Pro Ile Phe Gly Asn Gln Ile
                565                 570                 575

Ile Pro Asp Thr Ala Ile Leu Ser Val Val Pro Phe His His Gly Phe
            580                 585                 590

Gly Met Phe Thr Thr Leu Gly Tyr Leu Ile Cys Gly Phe Arg Val Val
        595                 600                 605

Leu Met Tyr Arg Phe Glu Glu Glu Leu Phe Leu Arg Ser Leu Gln Asp
        610                 615                 620

Tyr Lys Ile Gln Ser Ala Leu Leu Val Pro Thr Leu Phe Ser Phe Phe
625                 630                 635                 640

Ala Lys Ser Thr Leu Ile Asp Lys Tyr Asp Leu Ser Asn Leu His Glu
                645                 650                 655

Ile Ala Ser Gly Gly Ala Pro Leu Ser Lys Glu Val Gly Glu Ala Val
            660                 665                 670

Ala Lys Arg Phe His Leu Pro Gly Ile Arg Gln Gly Tyr Gly Leu Thr
        675                 680                 685
```

-continued

```
Glu Thr Thr Ser Ala Ile Leu Ile Thr Pro Glu Gly Asp Asp Lys Pro
    690                 695                 700
Gly Ala Val Gly Lys Val Val Pro Phe Phe Glu Ala Lys Val Val Asp
705                 710                 715                 720
Leu Asp Thr Gly Lys Thr Leu Gly Val Asn Gln Arg Gly Glu Leu Cys
                725                 730                 735
Val Arg Gly Pro Met Ile Met Ser Gly Tyr Val Asn Asn Pro Glu Ala
            740                 745                 750
Thr Asn Ala Leu Ile Asp Lys Asp Gly Trp Leu His Ser Gly Asp Ile
        755                 760                 765
Ala Tyr Trp Asp Glu Asp Glu His Phe Phe Ile Val Asp Arg Leu Lys
    770                 775                 780
Ser Leu Ile Lys Tyr Lys Gly Tyr Gln Val Ala Pro Ala Glu Leu Glu
785                 790                 795                 800
Ser Ile Leu Leu Gln His Pro Asn Ile Phe Asp Ala Gly Val Ala Gly
                805                 810                 815
Leu Pro Asp Asp Asp Ala Gly Glu Leu Pro Ala Ala Val Val Val Leu
            820                 825                 830
Glu His Gly Lys Thr Met Thr Glu Lys Glu Ile Val Asp Tyr Val Ala
        835                 840                 845
Ser Gln Val Thr Thr Ala Lys Lys Leu Arg Gly Gly Val Val Phe Val
    850                 855                 860
Asp Glu Val Pro Lys Gly Leu Thr Gly Lys Leu Asp Ala Arg Lys Ile
865                 870                 875                 880
Arg Glu Ile Leu Ile Lys Ala Lys Lys Gly Gly Lys Ser Lys Leu
                885                 890                 895
```

METHOD FOR GENERATING ENGINEERED CELLS BY HOMOLOGOUSLY RECOMBINING SEGMENTS HAVING INCREASED DEGENERACY

CROSS-REFERENCE TO RELATED APPLICATIONS

This Application claims the benefit of U.S. Provisional Application No. 60/349,565, filed Jan. 18, 2002, the disclosure of which is incorporated herein by reference in its entirety.

TECHNICAL FIELD OF THE INVENTION

The invention is related to the area of homologous recombination in eukaryotic cells for studying gene function, gene expression, and generating over-producer clones for high protein production. In particular it is related to the field of therapeutic target discovery, pharmacologic compound screening and protein manufacturing.

BACKGROUND OF THE INVENTION

The use of specific gene targeting in eukaryotic cell-based model systems provides an effective and selective strategy for studying the function of a particular gene in response to biological or chemical molecules as well as for model systems to produce biochemicals for therapeutic use. In particular is the use of homologous recombination to: (1) inactivate gene function to study downstream functions; (2) introduce reporter gene molecules into targeted loci to facilitate the screening of gene expression in response to biomolecules and/or pharmaceutical compounds; (3) generate stable, steady-state expression of target genes via the introduction of constitutively active heterologous promoter elements or through chromosomal site-specific gene amplification.

Standard methods for introducing targeting genes to a locus of interest are known by those skilled in the art. Gene targeting in prokaryotes and lower organisms has been well established, and methods for in vivo gene targeting in animal models have also been described (de Wind N. et al. (1995) "Inactivation of the mouse Msh2 gene results in mismatch repair deficiency, methylation tolerance, hyperrecombination, and predisposition to cancer" Cell 82:321-300).

The generation of knockouts in somatic cells, however, is more problematic due to low efficiency of transfection and endogenous biochemical activities that monitor for DNA strand exchange. Work done by Waldman et al. (Waldman, T., Kinzler, K. W., and Vogelstein, B. (1995) Cancer Res. 55:5187-5190) demonstrated the ability to generate somatic cell knockouts in a human cell line called HCT116 at relatively high rate. In the described studies, the authors used a targeting vector containing the neomycin (neo) resistance gene to knockout a locus of interest. Using this cell line the authors reported 37% of the neo resistant clones tested were found to contain a targeting vector within the homologous locus in the genome of the host.

Similar studies using other cell lines by these authors have been less successful. While the reason(s) for the lack or significant reduction in the frequency of recombination in somatic cell lines are not clear, some factors, such as the degree of transfection as well as the differences that may occur within the intracellular milieu of the host may play critical roles with regard to recombination efficiency. In the studies performed by Waldman et al., the cell line that the authors used was inherently defective for mismatch repair (MMR), a process involved in monitoring homologous recombination (de Wind N. et al. (1995) Cell 82:321-300). One proposed method for the high degree of recombination in this line was the lack of MMR, which has been implicated as a critical biochemical pathway for monitoring recombination (Reile, T E et al. WO 97/05268; Rayssigguier, C., et al. (1989) Nature 342:396-401; Selva, E., et al. (1995) Genetics 139: 1175-1188; U.S. Pat. No. 5,965,415 to Radman). Indeed, studies using mammalian and prokaryotic cells defective for MMR have previously demonstrated the increased chromosomal recombination with DNA fragments having up to 30% difference in sequence identity.

Nevertheless, homologous recombination in mammalian somatic cell lines has been and remains problematic due to the low efficiency of recombination. Although it is believed by many skilled in the art that low rate of homologous recombination may be overcome by the blockade of MMR (Reile, T E et al. WO 97/05268; Rayssigguier, C., et al. (1989) Nature 342:396-401; Selva, E., et al. (1995) Genetics 139:1175-1188; U.S. Pat. No. 5,965,415 to Radman; Beth Elliott and Maria Jasin, "Repair of Double-Strand Breaks by Homologous Recombination in Mismatch Repair-Defective Mammalian Cells" (2001) Mol. Cell Biol., 21:2671-2682) these methods teach the use of using MMR defective unicellular organisms to increase homologous recombination. A significant bottleneck to this approach is the need to clone large segments of homologous DNA from the target locus. Moreover, while it has been reported that short oligonucleotides are capable of homologously recombining at site-specific regions of the genome (Igoucheva O, Alexeev V, Yoon K., (2001) "Targeted gene correction by small single-stranded oligonucleotides in mammalian cells" Gene Ther. 8:391-399), the ability to integrate larger fragments with short terminal regions of homology remains elusive. In fact, recent studies by Inbar et al. (Inbar O, Liefshitz B, Bitan G, Kupiec M., (2000) "The Relationship between Homology Length and Crossing Over during the Repair of a Broken Chromosome" J. Biol. Chem. 275:30833-30838) demonstrated that fragments that contained only 123 bps of homologous sequence were not sufficient to induce homologous exchange of large DNA fragments in yeast. It has not been heretofore demonstrated that larger DNA fragments, such as those containing regulated or constitutively active promoter elements, gene inserts or reporter genes could be integrated into the exon of a locus in somatic mammalian cell lines with short, homologous terminal ends, such as fragments of only 20-120 nucleotides.

SUMMARY OF THE INVENTION

The ability to generate site-directed "knock-ins" in eukaryotic cells, in particular mammalian cells, used for drug screening or development of custom cell lines for constitutive gene expression is of great value for pharmaceutical drug product development as well as for compound screening. Compounds can be of a low molecular weight, a complex macromolecule or protein. The compound can be targeted to a gene of interest whose expression is altered either positively or negatively by directly or indirectly affecting the activity of promoter and/or enhancer elements that are involved in regulating the expression of a specific gene locus. One method taught in this application is the "knock-in" of constitutively active promoter elements (such as but not limited to viral promoters, i.e. SV40 early or late promoters, CMV, LTR, etc. or promoters from constitutively expressed housekeeping genes such as the elongation factor or actin) into a desired locus. The ability to direct constitutive gene expression from a host organisms genome may lead to the establishment of cell lines such as but not limited to those that overproduce therapeutic targets for drug binding studies, gene function studies as well as lines that overproduce therapeutic proteins for product manufacturing applications.

It is an object of the present invention to teach the process of rapidly generating gene-targeting fragments for eukaryotic cells, in particular somatic mammalian cells that can result in the site-specific chromosomal targeting of regulatory sequences that can alter endogenous gene expression of a given locus for function studies and gene product production. In addition, it is another object of the invention to teach the process of rapidly generating gene targeting fragments for eukaryotic cells that are capable of targeting a single exon of a chromosomal locus with a marker that can be used for monitoring gene expression to elucidate gene function with respect to disease and to monitor gene expression of a given locus in response to biological and pharmacological agents. It is another object of the invention to teach the process of generating locus-specific targeting fragments containing the dihydrofolate reductase (DHFR) gene for rapid, site-specific chromosomal integration and site-specific gene amplification as a tool for enhancing protein production for development and/or manufacturing applications.

The invention provides methods for introducing a locus specific targeting fragment into the genome of a cell through homologous recombination comprising: inhibiting endogenous mismatch repair of the cell; introducing a locus specific targeting fragment into the cell; wherein the locus specific targeting fragment is a polynucleotide comprising at least one promoter, a selectable marker and 5' and 3' flanking regions of about 20 to about 120 nucleotides; wherein the 5' and 3' flanking regions are homologous to a selected portion of the genome of the cell; and wherein the locus specific targeting fragment integrates into the genome of the cell by homologous recombination.

The invention also provides methods for genetically altering a cell to overproduce a selected polypeptide comprising: inhibiting endogenous mismatch repair of the cell; introducing a locus specific targeting fragment into the cell; wherein the locus specific targeting fragment is a polynucleotide comprising at least one promoter sequence, a selectable marker and 5' and 3' flanking regions of about 20 to about 120 nucleotides, wherein the 5' and 3' flanking regions are homologous to a selected portion of the genome of the cell, and wherein the locus specific targeting fragment integrates into the genome of the cell by homologous recombination; and selecting the cell that overproduces the selected polypeptide.

The invention also provides methods for tagging an exon of a cell for screening gene expression in response to biochemical or pharmaceutical compounds comprising: inhibiting endogenous mismatch repair of the cell; and introducing a locus specific targeting fragment into the cell; wherein the locus specific targeting fragment is a polynucleotide comprising a reporter element, a selectable marker and 5' and 3' flanking regions of about 20 to about 120 nucleotides, wherein the 5' and 3' flanking regions are homologous to a selected portion of the genome of the cell; wherein the locus specific targeting fragment integrates within a targeted gene's exon by homologous recombination; and wherein the cells containing genes with tagged exons are used for screening gene expression in response to biochemical or pharmaceutical compounds.

The invention also provides methods for tagging a specific chromosomal site for locus-specific gene amplification comprising: inhibiting endogenous mismatch repair of the cell; and introducing a locus specific targeting fragment into the cell; wherein the locus specific targeting fragment is a polynucleotide comprising, operatively linked: a dihydrofolate reductase gene, a promoter, and 5' and 3' flanking regions of about 20 to about 120 nucleotides, wherein the 5' and 3' flanking regions are homologous to a selected portion of the genome of the cell; wherein the locus specific targeting fragment integrates into the genome of the cell by homologous recombination; and wherein the specific chromosomal site is tagged for locus specific gene amplification.

In some embodiments of the method of the invention, the method further comprises restoring mismatch repair activity of the cell.

In some embodiments of the methods of the invention, the promoter may be a CMV promoter, an SV40 promoter, elongation factor, LTR sequence, a pIND promoter sequence, a tetracycline promoter sequence, or a MMTV promoter sequence.

In some embodiments of the methods of the invention, the selectable marker may be a hygromycin resistance gene, a neomycin resistance gene or a zeocin resistance gene.

In some embodiments of the methods of the invention, the 5' and 3' flanking regions are about 30 to about 100 nucleotides in length. In other embodiments of the methods of the invention, the 5' and 3' flanking regions are about 40 to about 90 nucleotides in length. In other embodiments of the methods of the invention, the 5' and 3' flanking regions are about 50 to about 80 nucleotides in length. In other embodiments of the methods of the invention, the 5' and 3' flanking regions are about 50 to about 70 nucleotides in length.

In some embodiments of the methods of the invention, the cell may be a vertebrate cell, an invertebrate cell, a mammalian cell, a reptilian cell, a fungal cell, or a yeast cell.

In some embodiments of the methods of the invention, the 5' and 3' flanking regions are homologous to a 5' flanking region of a selected chromosomal locus of the cell.

In some embodiments of the methods of the invention, the mismatch repair is inhibited by introducing into the cell a dominant negative allele of a mismatch repair gene. In other embodiments, mismatch repair is inhibited using a chemical inhibitor of mismatch repair. In embodiments using a dominant negative allele of a mismatch repair gene, the allele may be a dominant negative form of a PMS2 (SEQ ID NO:2 and SEQ ID NO:4), PMS1 (SEQ ID NO:6), MSH2 (SEQ ID NO:8), MSH6 (SEQ ID NO:41), MLH1 (SEQ ID NO:10), PMSR2 (SEQ ID NO:43), or a PMSR3 (also known as PMSL9) (SEQ ID NO:45). In some embodiments, the dominant negative form of the PMS2 gene is a PMS2-134 gene (SEQ ID NO:12), a PMSR2 gene (SEQ ID NO:43), or a PMSR3 gene (SEQ ID NO:45).

Some embodiments of the method may comprise a polynucleotide that also comprises a reporter element, including, but not limited to a form of luciferase or a green fluorescent protein. In some embodiments, the reporter element is fused in frame to the selectable marker.

In some embodiments, the locus specific targeting fragment further comprises a selectable marker and a second promoter operatively linked to the selectable marker.

The invention also provides locus specific targeting fragments comprising: a dihydrofolate reductase gene operatively linked to a promoter, and 5' and 3' flanking regions of about 20 to about 120 nucleotides wherein the 5' and 3' flanking sequences are homologous to a selected portion of a genome of a cell.

The invention also provides locus specific targeting fragments comprising: a reporter element, a selectable marker operatively linked to a promoter, and 5' and 3' flanking regions of about 20 to about 120 nucleotides.

The invention also provides locus specific targeting fragments comprising: at least one promoter sequence, a selectable marker and 5' and 3' flanking regions of about 20 to about 120 nucleotides.

In some embodiments of the compositions of the invention, the locus specific targeting fragment further comprises a selectable marker operatively linked to a second promoter sequence. The compositions may further comprise an IRES sequence between two protein encoding sequences such as between a dihydrofolate reductase gene and a selectable marker, for example.

In some embodiments the 5' and 3' flanking regions of the locus specific targeting sequence are about 30 to about 100 nucleotides in length. In other embodiments the 5' and 3' flanking regions of the locus specific targeting sequence are about 40 to about 90 nucleotides in length. In other embodiments the 5' and 3' flanking regions of the locus specific targeting sequence are about 50 to about 80 nucleotides in length. In other embodiments the 5' and 3' flanking regions of the locus specific targeting sequence are about 50 to about 70 nucleotides in length.

The invention also provides methods for producing a locus specific targeting fragment comprising amplifying a nucleic acid construct comprising a promoter and a selectable marker with a 5' and 3' primer in a polymerase chain reaction, wherein the 5' primer comprises about 20 to about 120 nucleotides that are homologous to a portion of the genome of a cell positioned 5' of a target locus, and wherein the 3' primer comprises about 20 to about 120 nucleotides that are homologous to a portion of the genome of a cell positioned 3' of the target locus.

In some embodiments of the method of the invention, the nucleic acid construct further comprises a second protein encoding sequence operatively linked to a second promoter. In some embodiments, the second protein encoding sequences is a dihydrofolate reductase sequence.

In some embodiments, the method further comprises the step of selecting the cells based on resistance to methotrexate. In some embodiments, the locus specific targeting fragment further comprises an operatively positioned locus control region.

The invention also provides methods for introducing a locus specific targeting fragment into the genome of a cell through homologous recombination comprising: introducing a locus specific targeting fragment into a mismatch repair-deficient cell; wherein the locus specific targeting fragment is a polynucleotide comprising a nucleic acid sequence to be incorporated into the genome of the mismatch repair deficient cell; wherein the polynucleotide comprises portions of about 20 to about 120 nucleotides, each flanking the 5' and 3' portion of the nucleic acid sequence to be incorporated into the genome; wherein the 5' and 3' flanking regions are homologous to a selected portion of the genome of the cell; and wherein the locus specific targeting fragment integrates into the genome of the mismatch repair deficient cell by homologous recombination.

The invention described herein is directed to the use of a process for the rapid generation of locus specific targeting fragments (LSTFs) that are capable of integrating within a given locus, to regulate the expression of a specific gene locus in a host cells for product manufacturing, studying gene function, and/or expression profiling gene expression under homeostatic, pathogenic, or environmentally altered conditions. Promoter targeted eukaryotic cell lines are generated by using 50-150 nucleotide (nt) primers whereby the 3' termini of each primer (last 30 nts) are specific for the 5' and 3' end of a plasmid cassette containing a expression element (i.e., constitutive promoter) juxtaposed to a constitutively expressed, selectable marker gene (i.e., neomycin-, hygromycin-resistant, etc., gene). The 5' sequence (20 to 120 nts) of each primer preferably contains 100% homology to the chromosomal target area of interest. In the case of generating tagged exons within a targeted locus, a similar method is employed as above, except that the cassette contains a reporter element such as, but not limited to, firefly luciferase (shown by nucleic acid sequence, SEQ ID NO:35, and amino acid sequence, SEQ ID NO:34), green fluorescent protein (shown by nucleic acid sequence, SEQ ID NO:37, and amino acid sequence, SEQ ID NO:36), bacterial luciferases; Renilla luciferase (shown by nucleic acid sequence, SEQ ID NO:39, and amino acid sequence, SEQ ID NO:38), a bifunctional ruc-gfp chimera (comprising a cDNA for Renilla luciferase (ruc) in-frame with a cDNA encoding the "humanized" GFP (gfp) from Aequorea (Wang et al. (2002) Mol. Genet. Genomics 268(2):160-168)), and the like, fused in-frame to a selectable marker for selection. Finally, LSTFs can be used to deliver a DNA fragment encoding a constitutively expressed dihydrofolate reductase gene (DHFR) juxtaposed to a constitutively expressed selection marker into a specific chromosomal site. Upon integration of the DHFR-LSTF, cells can be chemically selected for locus amplification via drug resistance using methods know by those skilled in the art, which in turn will result in amplification of a gene locus and potentially over expression of its encoded gene product.

The homologous recombination of small overlapping DNA regions is difficult to achieve, however, it is taught by this application that the use of inhibiting mismatch repair (MMR) in eukaryotic somatic cells increases the efficiency of homologous recombination that allows for the rapid generation of recombination using homologous regions as short as 20, 25, 30, 35, 40, 45, 50, 55, 60, 65, 70, 75, 80, 85, 90, 95, 100, 105, 110, 115, or 120 nucleotides in length. In some embodiments, the homologous regions are as short as about 25 to about 115 nucleotides in length. In other embodiments, the homologous regions are as short as about 30 to about 110 nucleotides in length. In other embodiments, the homologous regions are as short as about 35 to about 105 nucleotides in length. In other embodiments, the homologous regions are as short as about 40 to about 100 nucleotides in length. In other embodiments, the homologous regions are as short as about 45 to about 95 nucleotides in length. In other embodiments, the homologous regions are as short as about 50 to about 90 nucleotides in length. In other embodiments, the homologous regions are about 50 to about 85 nucleotides in length. In other embodiments, the homologous regions are about 50 to about 80 nucleotides in length. In other embodiments, the homologous regions are about 50 to about 75 nucleotides in length. In other embodiments, the homologous regions are about 50 to about 70 nucleotides in length.

The inhibition of MMR in such hosts can be achieved by using dominant negative mutant MMR genes as described (Nicolaides, N. C. et al. (1998) "A naturally occurring hPMS2 mutation can confer a dominant negative mutator phenotype" Mol. Cell. Biol. 18:1635-1641; U.S. Pat. No. 6,146,894 to Nicolaides et al.) or through the use of chemicals that can inhibit MMR of a host organism. Once the targeting vector is introduced, MMR is restored by removal of the dominant negative allele or removal of the MMR inhibitor and hosts are selected for integrated fragments by selection of the appropriate marker gene.

The use of somatic eukaryotic cells containing knocked-in expression control elements or exon-tags, or DHFR amplification units as taught by this application, will facilitate studies on elucidating unknown gene function by the ability to over express genomic loci at will under a variety of experimental growth conditions in the presence or absence of exogenous biological or pharmacological factors. Moreover, the use of such an approach to specifically tag a gene's exon will facilitate the profile of gene expression under certain growth conditions in wild type and pathogenic cells grown in the presence or absence of biological or pharmaceutical factors. Finally, the ability to specifically amplify chromosomal regions can facilitate enhanced protein production in a given host organism for discovery, development, and/or manufacturing or a given gene product.

The invention described herein is directed to the creation of genetically modified eukaryotic cells, in particular, somatic mammalian cells containing targeted loci with regulated or constitutively active expression elements for the use in uncovering gene function or polypeptide production as well as the use of targeting vectors that can tag an exon of a locus which can subsequently be monitored in response to biological or pharmaceutical molecules. The ability to generate such cells are facilitated by the use of targeting cassettes containing elements that are rapidly modified to target a given locus via PCR-mediated synthesis using locus specific primers containing 20-120 nts, specifically 50-70 nts, of homologous sequence to the chromosomal target site in combination with the use of agents that can block the endogenous MMR of the host during DNA integration to increase recombination efficiency of short homologous sequences (Nicholas Nicolaides, personal observation).

The present invention describes the facilitated synthesis of gene targeting fragments for controlling gene expression from the chromosomal site within eukaryotic cells as well as the use of exon-tagging fragments to study gene expression in the presence of biological or pharmaceutical agents. The advantages of the present invention are further described in the examples and figures described herein.

The present invention provides methods for generating somatic eukaryotic cells with altered gene expression profiles via homologous recombination in vivo, whereby gene expression is altered by the integration of DNA sequences containing constitutive promoter elements and a selectable marker. One method for generating such a cell line is through the use of DNA fragments containing 20-120 nts of homologous terminal sequences that are specific for a gene locus of interest in cells devoid of MMR.

The invention also provides methods for generating somatic eukaryotic cells containing genes with a tagged exon, whereby the cell is generated via the integration of DNA sequences containing reporter elements fused to a selectable marker. One method for generating such a cell line is through the use of DNA fragments containing 20-120 nts of homologous terminal sequence to a specific gene locus of interest in cells devoid of MMR.

The invention also provides methods for generating genetically engineered somatic cell lines that over produce polypeptides through the use of promoter targeting fragments to chromosomal loci.

The invention also provides methods for generating genetically engineered somatic cell lines that have a chromosomal site-specific integration of a constitutively expressed DHFR gene through the use of locus targeting fragments to chromosomal loci for selection of amplified loci through chemical-induced gene amplification using methods known by those skilled in the art.

In some embodiments, the invention provides methods for generating genetically altered cell lines that overproduce polypeptides for function studies. In other embodiments, the invention provides methods for generating genetically altered cell lines that overproduce polypeptides for production purposes. In other embodiments, the invention provides methods for generating genetically altered cell lines with genes whose exons are tagged for screening purposes.

In some embodiments, the invention provides methods of enhancing the frequency of homologous recombination of a DNA fragment within a specific chromosomal locus in eukaryotic cells by blocking the MMR activity of the somatic cell host.

In some embodiments, the invention provides methods of creating targeted eukaryotic cell lines with chromosomal loci containing DHFR expression vector for locus-specific gene amplification.

These and other objects of the invention are provided by one or more of the embodiments described below.

In one embodiment of the invention, a method for making a somatic eukaryotic cell line MMR defective, followed by the introduction of a locus specific targeting fragment that results in the constitutive expression of a chromosomal locus is provided. A polynucleotide encoding a dominant negative allele of a MMR gene is introduced into a target cell. The cell becomes hypermutable as a result of the introduction of the gene. A targeting fragment is generated by PCR using primers containing sequences homologous to the chromosomal locus of interest. The fragment is introduced into the host by transfection. Cell pools are then selected for clones with integrated fragments. Selected clones are further analyzed by any number of means to assess expression and/or genome integration of a specific site. Upon confirmation of site-desired integration, MMR is restored in clones and the cells are useful for functional studies or for generating high levels of protein for product development and/or manufacturing applications.

In another embodiment of the invention, a cell line with a targeted exon is provided. A somatic eukaryotic cell line is rendered MMR defective by introduction of a dominant negative MMR gene allele, followed by the introduction of a targeting fragment containing a reporter gene fused to a selectable marker that results in the tagging of an endogenous gene's exon is provided. A polynucleotide encoding a dominant negative allele of a MMR gene is introduced into a target cell. The cell becomes hypermutable as a result of the introduction of the gene. A targeting fragment is generated by PCR using primers containing sequences homologous to the chromosomal locus of interest. The fragment is introduced into the host by transfection. Cell pools are then selected for clones with integrated fragments. Selected clones are further analyzed by any number of means to assess expression and/or genome integration of a specific site. Upon confirmation of site-desired integration, MMR is restored in clones and the cells are useful for functional studies to profile endogenous gene expression in the presence or absence of biological or pharmacological factors.

Yet in another embodiment of the invention, a cell line with a targeted locus is provided. A somatic eukaryotic cell line is rendered MMR defective by introduction of a dominant negative MMR gene allele, followed by the introduction of a targeting fragment containing a DHFR gene and a selectable marker that results in the specific tagging of a chromosomal site is described. A polynucleotide encoding a dominant negative allele of a MMR gene is introduced into a target cell. The cell becomes hypermutable as a result of the introduction of the gene. A targeting fragment is generated by PCR using primers containing sequences homologous to the chromosomal locus of interest. The fragment is introduced into the host by transfection. Cell pools are then selected for clones with integrated fragments. Selected clones are further analyzed by any number of means to assess expression and/or genome integration of a specific site. Upon confirmation of site-desired integration, cells are selected for methotrexate (MTX) resistance. MTX-resistant cells are then analyzed for chromosomal site amplification using any means useful to those skilled in the art such as but not limited to genomic analysis by southern blot, RNA expression analysis or protein expression analysis. Upon successful amplification, MMR is restored in clones and the cells are useful for functional studies to profile endogenous gene expression in the presence or absence of biological or pharmacological factors as well as for production strains.

These and other embodiments of the invention provide the art with methods that can rapidly generate gene targeted eukaryotic cells whereby the locus of interest can have altered expression profiles to study gene function and/or enhanced production levels for manufacturing. Moreover, the invention provides the art with methods to tag an exon of a gene that is useful for monitoring gene expression within a given host.

BRIEF DESCRIPTION OF THE DRAWINGS

FIG. 3A shows the sequence of the fusion gene hygromycin-green fluorescence binding protein for exon tagging of somatic cells (SEQ ID NO:46). The sequence in bold encodes for the hygromycin resistance gene, while the sequence in normal font encodes the green fluorescence binding protein.

FIG. 3B shows the sequence of the fusion gene hygromycin-luciferase for exon tagging of somatic cells (SEQ ID NO:47). The sequence in bold encodes for the hygromycin resistance gene, while the sequence in normal font encodes the luciferase protein.

DETAILED DESCRIPTION OF THE INVENTION

Figure 1:
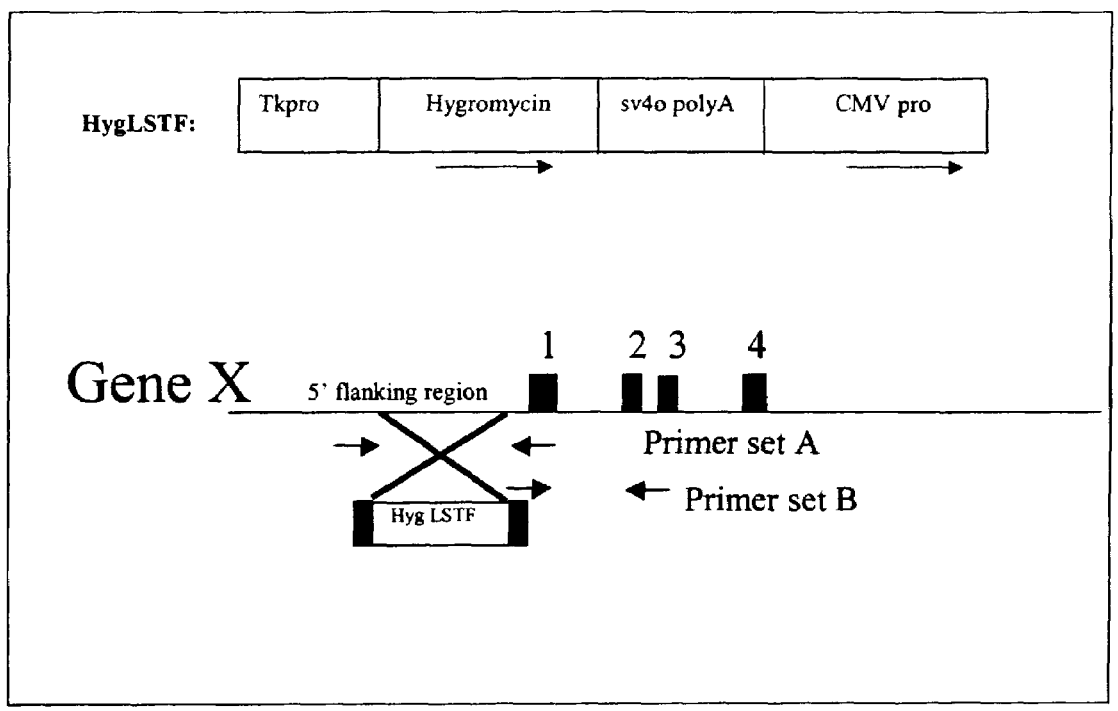
FIG. 1 shows a schematic diagram of promoter locus-specific targeting fragments (LSTF) and the genomic organization of a target gene. Primer Set A indicates the primer position of the oligonucleotides used to generate the LSTF for each gene that is useful for genome analysis. Primer Set B indicates the primer position of oligonucleotides used to analyze each target gene to confirm locus specific integration. The box below each gene represents the LSTF, where the shaded areas represent the areas of homology to the target gene, whereby the homologous region is 50-70 nts in length. The black boxes in the gene diagram represents exons that are numbered with respect to homology to the target gene whereby sensitive RT-PCR can be used to assay for fusion spliced cDNAs consisting of CMV leader sequence located 3' to the CMV promoter elements. The targeting cassette is used for generating constitutive expression from a eukaryotic host's genome.

Various definitions are provided herein. Most words and terms have the meaning that would be attributed to those words by one skilled in the art. Words or terms specifically defined herein have the meaning provided in the context of the present invention as a whole and as are typically understood by those skilled in the art. Any conflict between an art-understood definition of a word or term and a definition of the word or term as specifically taught herein shall be resolved in favor of the latter. Headings used herein are for convenience and are not to be construed as limiting.

As used herein, "MMR" refers to mismatch repair.

As used herein, "inhibitor of mismatch repair" refers to an agent that interferes with at least one function of the mismatch repair system of a cell and thereby renders the cell more susceptible to mutation.

As used herein, "hypermutable" refers to a state in which a cell in vitro or in vivo is made more susceptible to mutation through a loss or impairment of the mismatch repair system.

As used herein, "agents," "chemicals," and "inhibitors" when used in connection with inhibition of MMR refers to chemicals, oligonucleotides, analogs of natural substrates, and the like that interfere with normal function of MMR.

The term "gene" is used herein to denote a DNA segment encoding a polypeptide, and includes genomic DNA (with or without intervening sequences), cDNA, and synthetic DNA. Genes may include non-coding sequences, including promoter elements.

As used herein, "operably linked", when referring to DNA segments, indicates that the segments are arranged so that they function in concert for their intended purposes, e.g., transcription initiates in the promoter and proceeds through the coding segment to the terminator.

As used herein, the term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

As used herein, the term "promoter elements" is used to denote sequences within promoters that function in the initiation of transcription and which are often characterized by consensus nucleotide sequences. Promoter elements include RNA polymerase binding sites; TATA sequences; CAAT sequences; differentiation-specific elements (DSEs; McGehee et al. (1993) *Mol. Endocrinol.* 7:551-560; cyclic AMP response elements (CREs); serum response elements (SREs; Treisman (1990) *Seminars in Cancer Biol.* 1:47-58); glucocorticoid response elements (GREs); and binding sites for other transcription factors, such as CRE/ATF (O'Reilly et al. (1992) *J. Biol. Chem.* 267:19938-19943), AP2 (Ye et al. (1994) *J. Biol. Chem.* 269:25728-25734), SP1, cAMP response element binding protein (CREB; Loeken (1993) *Gene Expr.* 3:253-264) and octamer factors. See, in general, Watson et al. eds., MOLECULAR BIOLOGY OF THE GENE, 4TH ED., The Benjamin/Cummings Publishing Company, Inc., Menlo Park, Calif., 1987; and Lemaigre and Rousseau, (1994) *Biochem. J.* 303:1-14.

"Transcription regulatory elements" are promoter-associated DNA sequences that bind regulatory molecules, resulting in the modulation of the frequency with which transcription is initiated. Transcription regulatory elements can be classified as enhancers or suppressors of transcription.

As used herein, the term "reporter gene" is used herein to denote a gene that, when expressed in a cell, produces a quantifiable phenotypic change in the cell. Preferred reporter genes include genes encoding enzymes. Particularly preferred enzymes are luciferase, β-galactosidase, and chloramphenicol acetyltransferase. Assays for these enzymes are known in the art. See, for example, Seed and Sheen (1988) *Gene* 67:271-277; Todaka et al. (1994) *J. Biol. Chem.* 269: 29265-29270; Guarente et al. (1981) *Proc. Natl. Acad. Sci. USA* 78:2199-2203; Mellon et al. (1989) *Proc. Natl. Acad. Sci. USA* 86:4887-4891; and Brasier et al. (1989) *BioTechniques* 7:1116-1122, which are incorporated herein by reference in their entirety. Reporter genes, assay kits, and other materials are available commercially from suppliers such as Promega Corp. (Madison, Wis.) and GIBCO BRL (Gaithersburg, Md.).

The inventors have discovered a method for developing a rapid method for knocking in DNA fragments into target loci of interest to regulate gene expression and/or function as well as the ability to rapidly tag an exon of a gene to study expression as well as for enhancing chromosomal site-specific gene amplification. The process entails the use of targeting cassettes that are generated via PCR using primers containing 20, 25, 30, 35, 40, 45, 50, 55, 60, 65, 70, 75, 80, 85, 90, 95, 100, 105, 110, 115, or 120 nucleotides of sequence with homology to a particular chromosomal locus. Each promoter expression cassette contains DNA elements that can produce constitutive-, inducible- or suppressed-expression, which are juxtaposed to a constitutively expressed selectable marker (See FIG. 1). Each exon-tag cassette contains DNA sequences encoding for reporter elements that can be monitored using a number of detection methods such as but not limited to green fluorescent protein, luciferase, etc., which is fused in-frame to a selectable marker (See FIG. 4). Each DHFR expression cassette contains DNA elements that constitutively express DHFR which are juxtaposed to a constitutively active selectable marker. In all cases, targeting fragments are generated and transfected into eukaryotic cell hosts.

Enhanced site-specific homologous recombination of LSTFs is facilitated in each target cell by suppressing the endogenous MMR of the host via the expression of a dominant negative MMR gene mutants or through exposure to chemical inhibitors as described (Nicolaides, N. C. et al. (1998) "A naturally occurring hPMS2 mutation can confer a dominant negative mutator phenotype" *Mol. Cell. Biol.* 18:1635-1641; U.S. Pat. No. 6,146,894 to Nicolaides et al.; Lipkin et al. (2000) "MLH3: a DNA mismatch repair gene associated with mammalian microsatellite instability" *Nat. Genet.* 24:27-35).

In one aspect of the invention, the methods taught here are useful for the generation of cells that over express or suppress the expression of a gene(s) to elucidate gene function. Such cells may be used as tools to identify compounds that can alter the activity of a given gene product and/or induced pathway in comparison to parental lines. The cell host may be derived from a variety of sources, for example, normal or pathogenic tissues or organisms. The targeting fragment may be used, for example, to prevent, inhibit or terminate expression of a particular gene to elucidate its function, if any, in a particular disease-associated pathway. Moreover, such cell lines may now be used to screen compound libraries to identify molecules that act as agonists or antagonists for pharmaceutical product development. One such example is the ability to over express orphan G coupled receptors (GCR) in a cell line and expose the line to compound libraries to identify ligands or agonists. The ability to over express a GCR from the genome via enhanced promoter activity or chromosomal specific amplification is more beneficial than cloning and establishing stable transgenes, which in many instances produce very low or no expressed product. Finally, the ability to generate cell lines that can over produce a secreted or endogenous gene product from a host's genome enhances their use for biological product manufacturing thus bypassing the need for introducing multiple plasmid copies into host cell lines and establishing stable expression.

In another aspect of the invention, the methods are useful for the generation of cells with endogenous genes containing a tagged exon for monitoring gene expression profiles. Such cells may be used as tools to monitor physiological activity in the presence or absence of exogenous factors in comparison to control lines. The cell host may be derived from, for example, normal or pathogenic organisms to study the expression profile of disease associated genes under normal or stimulated conditions. Pharmacological studies can be performed in untreated cultures or in cultures treated with biological or chemical factors to screen for therapeutic molecules. The cell lines produced by the method of the invention containing tagged exons are also useful for monitoring compound toxicity and efficacy of modulating gene expression.

Reporter elements may be included in the constructs of the invention. Reporter elements include assayable proteins which can be detected and/or quantified. Examples o f reporter genes include, but are not limited to luciferases, such as those known in the art, and may include firefly luciferase (amino acid, SEQ ID NO:34, nucleic acid SEQ ID NO:35); bacterial luciferases, and *Renilla* luciferase (amino acid, SEQ ID NO:38, nucleic acid SEQ ID NO:39) and green fluorecence protein (amino acid, SEQ ID NO:36, nucleic acid SEQ ID NO:37). Other reporter elements include genes encoding enzymes, which convert a substrate that is subsequently detected. Examples include, but are not limited to β-galactosidase, and chloramphenicol acetyl transferase.

The reporter gene may be visualized in a variety of assays including both in vivo and in vitro assays. For example, but not by way of limitation, reporter genes can be visualized by positron emission tomography (PET), single photon emission computed tomography (SPECT), magnetic resonance imaging (MRI), and fluorescence with wild-type and mutant green fluorescent protein and luciferase (see Ray et al. (2001) "Monitoring gene therapy with reporter gene imaging" *Semin. Nucl. Med.* 31 (4):312-320).

For example, in living animals it has been shown that *Renilla* luciferase reporter gene could be used and detected to follow gene expression in vivo (Bhaumik and Gambhir (2002) *Proc. Natl. Acad. Sci. USA* 99(1):377-382). In this study, a highly sensitive cooled charge-coupled device (CCD) camera provided images of photon counting. Such a device is suitable for use in the present invention, and is available from Xenogen (In Vivo Imaging System "IVIS"). A description of the protocols used to image the reporter gene is known in the art (Bhaumik and Gambhir (2002) *Proc. Natl. Acad. Sci. USA* 99(1):377-382) and are suitable for use in the present invention as assays to monitor expression of reporter genes.

In another example, a bifunctional molecule comprising *Renilla* luciferase and Green Fluorescent Protein may be used as a reporter gene to monitor the integration and/or expression of the LSTF construct. In a study describing the bifunctional construct, a ruc-gfp fusion gene construct was created by fusing cDNAs for *Renilla* luciferase (ruc) and "humanized" GFP (gfp) from Aequorea in frame, and the construct was subsequently expressed in mammalian cells. The transformed cells exhibited both *Renilla* luciferase activity in the presence of the substrate, coelenterazine, and GFP fluorescence upon excitation with UV light. In animal experiments, the light emission from the fusion construct was detected externally in the organs and tissues of live animals (Wang et al. (2002) *Mol. Genet. Genomics* 268(2):160-168). Such a bifunctional construct is suitable for use in the present invention as a reporter gene.

In another embodiment of the invention, proteins expressed from LSTFs may be visualized in vitro or in vivo using labeled antibodies, or fragments thereof (such as Fab or F(ab')2 fragments) which specifically bind to the protein of interest. Antibodies may be labeled using any means known in the art that allow visualization or assaying. Such labels include, but are not limited to fluorescent conjugates, and radioactive conjugates. Fluorescent conjugates include luciferases, green fluorescent protein and derivatives, rhodamine, and fluorescein. Radioactive compounds include those containing $^{131}I$, $^{111}In$, $^{123}I$, $^{99m}Tc$, $^{32}P$, $^{125}I$, $^{3}H$, and $^{14}C$. The antibody or fragments thereof can be labeled with such reagents using techniques known in the art (see, for example, Wensel and Meares, Radioimmunoimaging and Radioimmunotherapy, Esevier, New York (1983); D. Colcher et al. (1986) "Use of Monoclonal Antibodies as Radiopharmaceuticals for the Localization of Human Carcinoma Xenografts in Athymic Mice" *Meth. Enzymol.* 121:802-816).

In yet another embodiment, signaling mechanisms that may be affected by proteins expressed by LSTFs may be monitored or assayed for functionality. In a non-limiting example, calcium flux may be measured in cells expressing receptors that affect calcium flux upon stimulation. Examples of protocols that measure calcium mobilization are the FLIPR® Calcium Assay Kit, and various protocols using the calcium binding, fluorescent dye, Fluo-3 AM. The protocols are known to those of skill in the art and may be used to measure calcium mobilization in cells expressing various proteins (such as G-protein coupled receptors, for example) which have been expressed from an LSTF.

The LSTF of the invention may be constructed to include a variety of genetic elements, depending on the application of the LSTF. For example, in some embodiments, a LSTF may include a promoter operatively linked to a selectable marker. In other embodiments, the LSTF may include a promoter operatively linked to a selectable marker and a second protein encoding sequence operatively linked to a second promoter. In constructs with more than one protein encoding sequence, an internal ribosome entry site (IRES) may also be included. An IRES element is a regulatory element found in some viral sequences and some cellular RNAs that enhances translation of a second gene product in a bicistronic eukaryotic expression cassette (Kaufman et al. (1991) *Nucl. Acids Res.* 19:4485). An IRES element may be engineered between two of the coding sequences of the LSTFs of the invention. In other embodiments in which it is not necessary that a protein sequence is expressed, a promoter is not required. In such embodiments (e.g., embodiments in which exons are tagged) it is sufficient that a nucleic acid sequence is present on the construct which may be detectable through molecular analysis. In embodiments in which chromosomal loci are targeted for amplification, constructs include a promoter operatively linked to a dihydrofolate reductase encoding sequence, preferably with a second promoter operatively linked to a selectable marker.

A selectable marker may be a gene conferring drug-resistance to the cell. Non-limiting examples of such drug resistance selectable markers are genes for neomycin resistance, hygromycin resistance and zeocin resistance.

In some embodiments of the invention, a locus control region (LCR) may be incorporated. An LCR is position and orientation dependent and may be used in a tissue specific manner. An LCR may be used in the LSTF of the invention in conjunction with a promoter in embodiments used for overproduction of protein. In a non-limiting example of use of an LCR, an LCR specific for lymphocytes may be used to produce high levels of antibodies in B cells using LSTFs that integrate through homologous recombination in the immunoglobulin locus. LCRs are known by persons skilled in the art.

The constructs are amplified in a polymerase chain reaction (PCR) using 5' and 3' primers that have been designed to include nucleic acid sequence that is homologous to a selected portion of the genome of a cell that is targeted for homologous recombination. For the 5' primer, which anneals to the (−) strand of the DNA in the PCR amplification, the 5'-most sequence of the 5' primer (about 20-120 nucleotides (nts)) is homologous to the selected portion of the genome targeted for homologous recombination. The 3' most portion of the 5' primer comprises nucleotides that are homologous to the 5' portion of the construct to be amplified. For the 3' primer, which anneals to the (+) strand of the DNA in the PCR reaction, the 5'-most sequence of about 20-120 nucleotides (nts) is homologous to the selected portion of the genome targeted for homologous recombination. The 3' most portion of the 3' primer comprises nucleotides that are homologous to the 3' portion of the construct to be amplified. The PCR reaction conditions are not particularly limited. PCR reactions and variations for optimization are well known in the are and routine optimization of the reactions, including choice of buffers, polymerases, additives, etc., are in the purview of the skilled artisan.

According to one aspect of the invention, a polynucleotide encoding for a dominant negative form of a MMR protein is introduced into a cell. The gene can be any dominant negative allele encoding a protein, which is part of a MMR complex. The dominant negative allele can be naturally occurring, or made in the laboratory. The dominant negative allele may be, for example a PMS2 allele and homologs thereof that confer a dominant negative phenotype. For example, the allele may be a PMS2-134 allele, a PMSR2 allele or a PMSR3 allele. The polynucleotide can be in the form of genomic DNA, cDNA, RNA, or a chemically synthesized polynucleotide.

The polynucleotide can be cloned into an expression vector containing a constitutively active promoter segment (such as but not limited to CMV, SV40, Elongation Factor (EF) or LTR sequences) or to inducible promoter sequences such as the steroid inducible pIND vector (Invitrogen), tetracycline, or mouse mammary tumor virus (MMTV), where the expression of the dominant negative MMR gene can be regulated. The polynucleotide can be introduced into the cell by transfection. As used herein, a "promoter" is a DNA sequence that encompasses binding sites for trans-acting transcription factors. Promoters, when positioned 5' of protein encoding sequences form a basic transcriptional unit.

According to another aspect of the invention, a targeting fragment containing 20, 25, 30, 35, 40, 45, 50, 55, 60, 65, 70, 75, 80, 85, 90, 95, 100, 105, 110, 115, or 120 nts of 5' and 3' homologous sequence is transfected into MMR deficient cell hosts, the cell is grown and screened for clones containing chromosomes whereby the targeting fragment has been integrated. MMR defective cells may be of human, primates, mammals, rodent, fish, plant, fungal, yeast or of the prokaryotic kingdom.

Transfection is any process whereby a polynucleotide is introduced into a cell. The process of transfection can be carried out in a living animal, e.g., using a vector for gene therapy, or it can be carried out in vitro, e.g., using a suspension of one or more isolated cells in culture. The cell can be any type of eukaryotic cell, including, for example, cells isolated from humans or other primates, mammals or other vertebrates, invertebrates, and single celled organisms such as protozoa, yeast, or bacteria.

In general, transfection will be carried out using a suspension of cells, or a single cell, but other methods can also be applied as long as a sufficient fraction of the treated cells or tissue incorporates the polynucleotide so as to allow transfected cells to be grown and utilized. Techniques for transfection are well known. Available techniques for introducing polynucleotides include but are not limited to electroporation (Potter et al. (1988) *Proc. Natl. Acad. Sci. USA* 81:7161), transduction, cell fusion, the use of calcium chloride Sambrook et al. MOLECULAR CLONING: A LABORATORY MANUAL, Cold Spring Harbor Press, New York, 2000) or calcium phosphate precipitation (Wigler et al. ( 1980) *Proc. Natl. Acad. Sci. USA* 77:3567), polyethylene-induced fusion of bacterial protoplasts with mammalian cells (Schaffner et al. (1980) *Proc. Natl. Acad. Sci. USA* 77:2163), and packaging of the polynucleotide together with lipid for fusion with the cells of interest (e.g., using Lipofectin® Reagent and Lipofectamine® Reagent (Gibco BRL, Gaithersburg, Md.). Once a cell has been transfected with the targeting fragment containing a selectable marker, the cell can be grown and reproduced in culture. If the transfection is stable, such that the selectable marker gene is expressed at a consistent level for many cell generations, then a cell line results. Upon chromosomal integration, MMR is restored in the host cell, and the genetic stability of the host is restored.

An isolated cell includes cells obtained from a tissue of humans, animals, plants or fungi by mechanically separating out individual cells and transferring them to a suitable cell culture medium, either with or without pretreatment of the tissue with enzymes, e.g., collagenase or trypsin. Such isolated cells are typically cultured in the absence of other types of cells. Cells selected for the introduction of a targeting fragment may be derived from a eukaryotic organism in the form of a primary cell culture or an immortalized cell line, or may be derived from suspensions of single-celled organisms.

Integration of the targeting fragment can be detected by analyzing the chromosomal locus of interest for alterations in the genotype of the cells or whole organisms, for example by examining the sequence of genomic DNA, cDNA, RNA, or polypeptides associated with the gene of interest. Integration can also be detected by screening for the expression levels of the targeted locus for altered expression profiles, or chimeric transcripts through biochemical methods or nucleic acid monitoring. Techniques for analyzing nucleic acids and proteins are well known in the art. Techniques include, but are not limited to Southern analysis, northern analysis, PCR, reverse transcriptase-PCR (rt-PCR), restriction digest mapping, western blot, enzyme-linked immunosorbent assays (ELISA), radioimmunoassay, immunoprecipitation, and well-known variations of these techniques.

Examples of mismatch repair proteins that can be used for dominant negative MMR inhibitors and nucleic acid sequences include the following: mouse PMS2 protein (SEQ ID NO:1); mouse PMS2 cDNA) (SEQ ID NO:2); human PMS2 protein (SEQ ID NO:3); human PMS2 cDNA (SEQ ID NO:4); human PMS1 protein (SEQ ID NO:5); human PMS1 cDNA (SEQ ID NO:6); human MSH2 protein (SEQ ID NO:7); human MSH2 cDNA (SEQ ID NO:8); human MLH1 cDNA (SEQ ID NO:10); human MLH1 cDNA (SEQ ID NO:9); human PMS2-134 protein (SEQ ID NO:11); human PMS2-134 cDNA (SEQ ID NO:12); human MSH6 protein (SEQ ID NO:40); human MSH6 cDNA (SEQ ID NO:41); human PMSR2 protein (SEQ ID NO:42); human PMSR2 cDNA (SEQ ID NO:43); human PMSR3 protein (SEQ ID NO:44); and human PMSR3 cDNA (SEQ ID NO:45).

The LSTFs of the invention may also be used to insert nucleic acid sequences through homologous recombination in cells that are naturally deficient in mismatch repair. Furthermore, cells may be rendered deficient in mismatch repair before, after or simultaneously with the introduction of the LSTFs.

The invention also employ chemical inhibitors of mismatch repair, such as described in WO 02/054856 Morphotek Inc. "Chemical Inhibitors of Mismatch Repair," which is specifically incorporated herein in it entirety. Chemicals that block MMR, and thereby render cells hypermutable, efficiently introduce mutations in cells and genes of interest as well as facilitate homologous recombination in treated cells. In addition to destabilizing the genome of cells exposed to chemicals that inhibit MMR activity may be done transiently, allowing cells to become hypermutable, and removing the chemical exposure after the desired effect (e.g., a mutation in a gene of interest) is achieved. The chemicals that inhibit MMR activity that are suitable for use in the invention include, but are not limited to, anthracene derivatives, nonhydrolyzable ATP analogs, ATPase inhibitors, antisense oligonucleotides that specifically anneal to polynucleotides encoding mismatch repair proteins, DNA polymerase inhibitors, and exonuclease inhibitors.

Examples of ATP analogs that are useful in blocking MMR activity include, but are not limited to, nonhydrolyzable forms of ATP such as AMP-PNP and ATP[gamma]S block the MMR activity (Galio et al. (1999) *Nucl. Acids Res.* 27:2325-2331; Allen et al. (1997) *EMBO J.* 16:4467-4476; Bjornson et al. (2000) *Biochem.* 39:3176-3183).

Examples of nuclease inhibitors that are useful in blocking MMR activity include, but are not limited to analogs of N-ethylmaleimide, an endonuclease inhibitor (Huang et al. (1995) *Arch. Biochem. Biophys.* 316:485), heterodimeric adeninechain-acridine compounds, exonulcease III inhibitors (Belmont et al. (2000) *Bioorg Med Chem Lett* (2000) 10:293-295), as well as antibiotic compounds such as heliquinomycin, which have helicase inhibitory activity (Chino et al. (1998) *J. Antibiot.* (Tokyo) 51:480-486).

Examples of DNA polymerase inhibitors that are useful in blocking MMR activity include, but are not limited to, analogs of actinomycin D (Martin et al. (1990) *J. Immunol.* 145:1859), aphidicolin (Kuwakado et al. (1993) *Biochem. Pharmacol.* 46:1909) 1-(2'-Deoxy-2'-fluoro-beta-L-arabinofuranosyl)-5-methyluracil (L-FMAU) (Kukhanova et al. (1998) *Biochem Pharmacol* 55:1181-1187), and 2',3'-dideoxyribonucleoside 5'-triphosphates (ddNTPs) (Ono et al. (1984) *Biomed. Pharmacother.* 38:382-389).

In yet another aspect of the invention, antisense oligonucleotides are administered to cells to disrupt at least one function of the mismatch repair process. The antisense polynucleotides hybridize to MMR polynucleotides. Both full-length and antisense polynucleotide frgaments are suitable for use. "Antisense polynucleotide fragments" of the invention include, but are not limited to polynuclotides that specifically hybridize to an MMR encoding RNA (as determined by sequence comparison of nucleotides encoding the MMR to nucleotides encoding other known molecules). Identification of sequences that are substantially unique to MMR-encoding polynucleotides can be ascertained by analysis of any publicly available sequence database and/or with any commercially available sequence comparison programs. Antisense molecules may be generated by any means including, but not limited to chemical synthesis, expression in an in vitro transcription reaction, through expression in a transformed cell comprising a vector that may be transcribed to produce antisense molecules, through restriction digestion and isolation, through the polymerase chain reaction, and the like.

Those of skill in the art recognize that the antisense oligonucleotides that inhibit mismatch repair activity may be predicted using any MMR genes. Specifically, antisense nucleic acid molecules comprise a sequence complementary to at least about 10, 15, 25, 50, 100, 250 or 500 nucleotides or an entire MMR encoding sequence. Preferably, the antisense oligonucleotides comprise a sequence complementary to about 15 consecutive nucleotides of the coding strand of the MMR encoding sequence.

In one embodiment, an antisense nucleic acid molecule is antisense to a "coding region" of the coding strand of a nucleotide sequence encoding an MMR protein. The coding strand may also include regulatory regions of the MMR sequence. The term "coding region" refers to the region of the nucleotide sequence comprising codons which are translated into amino acid residues (e.g., the protein coding region of human PMS2 corresponds to the coding region). In another embodiment, the antisense nucleic acid molecule is antisense to a "noncoding region" of the coding strand of a nucleotide sequence encoding an MMR protein. The term "noncoding region" refers to 5' and 3' sequences which flank the coding region that are not translated into amino acids (i.e., also referred to as 5' and 3' untranslated regions (UTR)).

Preferably, antisense oligonucleotides are directed to regulatory regions of a nucleotide sequence encoding an MMR protein, or mRNA corresponding thereto, including, but not limited to, the initiation codon, TATA box, enhancer sequences, and the like. Given the coding strand sequences provided herein, antisense nucleic acids of the invention can be designed according to the rules of Watson and Crick or Hoogsteen base pairing. The antisense nucleic acid molecule can be complementary to the entire coding region of an MMR mRNA, but more preferably is an oligonucleotide that is antisense to only a portion of the coding or noncoding region of an MMR mRNA. For example, the antisense oligonucleotide can be complementary to the region surrounding the translation start site of an MMR mRNA. An antisense oligonucleotide can be, for example, about 5, 10, 15, 20, 25, 30, 35, 40, 45 or 50 nucleotides in length.

As used herein the term "anthracene" refers to the compound anthracene. However, when referred to in the general sense, such as "anthracenes," "an anthracene" or "the anthracene," such terms denote any compound that contains the fused triphenyl core structure of anthracene, i.e.,

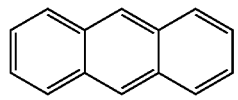

regardless of extent of substitution.

In certain preferred embodiments of the invention, the anthracene has the formula:

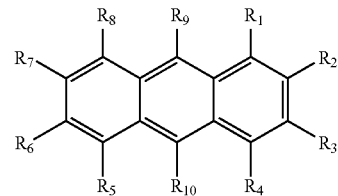

wherein $R_1$-$R_{10}$ are independently hydrogen, hydroxyl, amino, alkyl, substituted alkyl, alkenyl, substituted alkenyl, alkynyl, substituted alkynyl, O-alkyl, S-alkyl, N-alkyl, O-alkenyl, S-alkenyl, N-alkenyl,O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroalkyl, heteroaryl, and substituted heteroaryl contain at least one heteroatom that is oxygen, sulfur, a metal atom, phosphorus, silicon or nitrogen;

wherein said substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkyloxy, guanidino, alkoxycarbonyl, alkoxy, hydroxy, carboxy and amino; and wherein said amino groups optionally substituted with an acyl group, or 1 to 3 aryl or lower alkyl groups; or wherein any two of $R_1$-$R_{10}$ can together form a polyether;

or wherein any two of $R_1$-$R_{10}$ can, together with the intervening carbon atoms of the anthracene core, form a crown ether.

As used herein, "alkyl" refers to a hydrocarbon containing from 1 to about 20 carbon atoms. Alkyl groups may straight, branched, cyclic, or combinations thereof. Alkyl groups thus include, by way of illustration only, methyl, ethyl, propyl, isopropyl, butyl, isobutyl, cyclopentyl, cyclopentylmethyl, cyclohexyl, cyclohexylmethyl, and the like. Also included within the definition of "alkyl" are fused and/or polycyclic aliphatic cyclic ring systems such as, for example, adamantane. As used herein the term "alkenyl" denotes an alkyl group having at least one carbon-carbon double bond. As used herein the term "alkynyl" denotes an alkyl group having at least one carbon-carbon triple bond.

In some preferred embodiments, the alkyl, alkenyl, alkynyl, aryl, aryloxy, and heteroaryl substituent groups described above may bear one or more further substituent groups; that is, they may be "substituted". In some preferred embodiments these substituent groups can include halogens (for example fluorine, chlorine, bromine and iodine), CN, $NO_2$, lower alkyl groups, aryl groups, heteroaryl groups, aralkyl groups, aralkyloxy groups, guanidino, alkoxycarbonyl, alkoxy, hydroxy, carboxy and amino groups. In addition, the alkyl and aryl portions of aralkyloxy, arylalkyl, arylsulfonyl, alkylsulfonyl, alkoxycarbonyl, and aryloxycarbonyl groups also can bear such substituent groups. Thus, by way of example only, substituted alkyl groups include, for example, alkyl groups fluoro-, chloro-, bromo- and iodoalkyl groups, aminoalkyl groups, and hydroxyalkyl groups, such as hydroxymethyl, hydroxyethyl, hydroxypropyl, hydroxybutyl, and the like. In some preferred embodiments such hydroxyalkyl groups contain from 1 to about 20 carbons.

As used herein the term "aryl" means a group having 5 to about 20 carbon atoms and which contains at least one aromatic ring, such as phenyl, biphenyl and naphthyl. Preferred aryl groups include unsubstituted or substituted phenyl and naphthyl groups. The term "aryloxy" denotes an aryl group that is bound through an oxygen atom, for example a phenoxy group.

In general, the prefix "hetero" denotes the presence of at least one hetero (i.e., non-carbon) atom, which is in some preferred embodiments independently one to three O, N, S, P, Si or metal atoms. Thus, the term "heteroaryl" denotes an aryl group in which one or more ring carbon atom is replaced by such a heteroatom. Preferred heteroaryl groups include pyridyl, pyrimidyl, pyrrolyl, furyl, thienyl, and imidazolyl groups.

The term "aralkyl" (or "arylalkyl") is intended to denote a group having from 6 to 15 carbons, consisting of an alkyl group that bears an aryl group. Examples of aralkyl groups include benzyl, phenethyl, benzhydryl and naphthylmethyl groups.

The term "alkylaryl" (or "alkaryl") is intended to denote a group having from 6 to 15 carbons, consisting of an aryl group that bears an alkyl group. Examples of aralkyl groups include methylphenyl, ethylphenyl and methylnaphthyl groups.

The term "arylsulfonyl" denotes an aryl group attached through a sulfonyl group, for example phenylsulfonyl. The term "alkylsulfonyl" denotes an alkyl group attached through a sulfonyl group, for example methylsulfonyl.

The term "alkoxycarbonyl" denotes a group of formula —C(=O)—O—R where R is alkyl, alkenyl, or alkynyl, where the alkyl, alkenyl, or alkynyl portions thereof can be optionally substituted as described herein.

The term "aryloxycarbonyl" denotes a group of formula —C(=O)—O—R where R is aryl, where the aryl portion thereof can be optionally substituted as described herein.

The terms "arylalkyloxy" or "aralkyloxy" are equivalent, and denote a group of formula —O—R'—R", where R' is R is alkyl, alkenyl, or alkynyl which can be optionally substituted as described herein, and wherein R" denotes a aryl or substituted aryl group.

The terms "alkylaryloxy" or "alkaryloxy" are equivalent, and denote a group of formula —O—R'—R", where R' is an aryl or substituted aryl group, and R" is alkyl, alkenyl, or alkynyl which can be optionally substituted as described herein.

As used herein, the term "aldehyde group" denotes a group that bears a moiety of formula —C(=O)—H. The term "ketone" denotes a moiety containing a group of formula —R—C(=O)—R=, where R and R= are independently alkyl, alkenyl, alkynyl, aryl, heteroaryl, aralkyl, or alkaryl, each of which may be substituted as described herein.

As used herein, the term "ester" denotes a moiety having a group of formula —R—C(=O)—O—R= or —R—O—C (=O)—R= where R and R= are independently alkyl, alkenyl, alkynyl, aryl, heteroaryl, aralkyl, or alkaryl, each of which may be substituted as described herein.

The term "ether" denotes a moiety having a group of formula —R—O—R= or where R and R=are independently alkyl, alkenyl, alkynyl, aryl, heteroaryl, aralkyl, or alkaryl, each of which may be substituted as described herein.

The term "crown ether" has its usual meaning of a cyclic ether containing several oxygen atoms. As used herein the term "organosulfur compound" denotes aliphatic or aromatic sulfur containing compounds, for example thiols and disulfides. The term "organometallic group" denotes an organic molecule containing at least one metal atom.

The term "organosilicon compound" denotes aliphatic or aromatic silicon containing compounds, for example alkyl and aryl silanes.

The term "carboxylic acid" denotes a moiety having a carboxyl group, other than an amino acid.

As used herein, the term "amino acid" denotes a molecule containing both an amino group and a carboxyl group. In some preferred embodiments, the amino acids are α-, β-, γ- or δ-amino acids, including their stereoisomers and racemates. As used herein the term "L-amino acid" denotes an a-amino acid having the L configuration around the α-carbon, that is, a carboxylic acid of general formula $CH(COOH)(NH_2)$-(side chain), having the L-configuration. The term "D-amino acid" similarly denotes a carboxylic acid of general formula $CH(COOH)(NH_2)$-(side chain), having the D-configuration around the α-carbon. Side chains of L-amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, *Biochemistry, Second Edition*, Worth Publishers, Inc, 1975, pages 72-77, incorporated herein by reference. Amino acid substituents may be attached through their carbonyl groups through the oxygen or carbonyl carbon thereof, or through their amino groups, or through functionalities residing on their side chain portions.

As used herein "polynucleotide" refers to a nucleic acid molecule and includes genomic DNA cDNA, RNA, mRNA and the like.

As used herein "antisense oligonucleotide" refers to a nucleic acid molecule that is complementary to at least a portion of a target nucleotide sequence of interest and specifically hybridizes to the target nucleotide sequence under physiological conditions.

For further information on the background of the invention the following references may be consulted, each of which, along with other references cited herein, is incorporated herein by reference in its entirety:

References:

(1) Baker, S. M. et al. (1995) "Male defective in the DNA mismatch repair gene PMS2 exhibit abnormal chromosome synapsis in meiosis" *Cell* 82:309-319.

(2) Modrich, P. (1994) "Mismatch repair, genetic stability, and cancer" *Science* 266:1959-1960.

(3) Jiricny, J. and M. Nystrom-Lahti (2000) "Mismatch repair defects in cancer" *Curr. Opin. Genet. Dev.* 10:157-161.

(4) Prolla, T. A. et al. (1994) "MLH1, PMS1, and MSH2 interaction during the initiation of DNA mismatch repair in yeast" *Science* 264:1091-1093.

(5) Strand, M. et al. (1993) "Destabilization of tracts of simple repetitive DNA in yeast by mutations affecting DNA mismatch repair" *Nature* 365:274-276.

(6) Perucho, M. (1996) "Cancer of the microsatellite mutator phenotype" *Biol. Chem.* 377:675-684.

(7) Liu, T. et al. (2000) "Microsatellite instability as a predictor of a mutation in a DNA mismatch repair gene in familial colorectal cancer" *Genes Chrom. Cancer* 27:17-25.

(8) Nicolaides, N. C., et al. (1995) "Genomic organization of the human PMS2 gene family" *Genomics* 30:195-206.

The above disclosure generally describes the present invention. A more complete understanding can be obtained by reference to the following specific examples, which are pro-

EXAMPLES

Example 1

Stable Expression of Dominant Negative Mismatch Repair (MMR) Genes in Cells Results in MMR Inactivity.

Expression of a dominant negative allele in an otherwise mismatch repair (MMR) proficient cell can render these host cells MMR deficient (Nicolaides, N. C. et al. (1998) *Mol. Cell. Biol.* 18:1635-1641, U.S. Pat. No. 6,146,894 to Nicolaides et al.). The creation of MMR deficient cells can lead to the generation of genetic alterations throughout the entire genome of a host's offspring, yielding a population of genetically altered offspring or siblings that have an enhanced rate of homologous recombination. This patent application teaches of the use of dominant negative MMR genes in cells, including but not limited to rodent, human, primate, yeast, insect, fish and prokaryotic cells with enhanced rates of homologous recombination followed by the introduction of locus specific targeting fragments (LSTFs) that can alter the expression of a chromosomal locus or integrate into a given exon of a gene for facilitated analysis of gene expression.

To demonstrate the ability to create MMR defective mammalian cells with elevated rates of homologous recombination using dominant negative alleles of MMR genes, we first transfected a MMR proficient human cell line with an expression vector containing the human the previously published dominant negative PMS2 mutant referred herein a s PMS134 (cell line referred to as 293PMS134), or with no insert (cell line referred to as 293vec) into human embryonic kidney cells (HEK293). A fragment containing the PMS134 cDNA was cloned into the pEF expression vector, which contains the constitutively active elongation factor promoter along with the neomycin resistance gene as selectable marker. The results showed that the PMS134 mutant could exert a robust dominant negative effect, resulting in biochemical and genetic manifestations of MMR deficiency. A brief description of the methods is provided below.

A hallmark of MMR deficiency is the generation of unstable microsatellite repeats in the genome of host cells. This phenotype is referred to as microsatellite instability (MI). MI consists of deletions and/or insertions within repetitive mono-, di- and/or trinucleotide repetitive sequences throughout the entire genome of a host cell. Extensive genetic analysis eukaryotic cells have found that the only biochemical defect that is capable of producing MI is defective MMR. In light of this unique feature that defective MMR has on promoting MI, it is now used as a biochemical marker to survey for lack of MMR activity within host cells.

A method used to detect MMR deficiency in eukaryotic cells is to employ a reporter gene that has a polynucleotide repeat inserted within the coding region that disrupts its reading frame due to a frame shift. In the case where MMR is defective, the reporter gene will acquire random mutations (i.e. insertions and/or deletions) within the polynucleotide repeat yielding clones that contain a functional reporter gene. An example of the ability to alter desired genes via defective MMR comes from experiments using HEK293 cells (described above), where a mammalian expression construct containing a defective β-galactosidase gene (referred to as pCAR-OF) was transfected into 293PMS134 or 293vec cells as described above. The pCAR-OF vector consists of a β-galactosidase gene containing a 29-basepair poly-CA tract inserted at the 5' end of its coding region, which causes the wild-type reading frame to shift out-of-frame. This chimeric gene is cloned into the pCEP4, which contains the constitutively cytomegalovirus (CMV) promoter upstream of the cloning site and also contains the hygromycin-resistance (HYG) gene that allows for selection of cells containing this vector. The pCAR-OF reporter cannot generate β-galactosidase activity unless a frame-restoring mutation (i.e., insertion or deletion) arises following transfection into a host. Another reporter vector called pCAR-IF contains a β-galactosidase in which a 27-bp poly-CA repeat was cloned into the same site as the pCAR-OF gene, but it is biologically active because the removal of a single repeat restores the open reading frame and produces a functional chimeric β-galactosidase polypeptide (not shown). In these proof-of-concept studies, 293PMS134 and 293vec cells were transfected with the pCAR-OF reporter vector and selected for 17 days in neomycin plus hygromycin selection medium. After the 17$^{th}$ day, resistant colonies were stained for β-galactosidase production to determine the number of clones containing a genetically altered β-galactosidase gene. All conditions produced a relatively equal number of neomycin/hygromycin resistant cells, however, only the cells expressing the PMS134 dominant negative allele (293PMS134) contained a subset of clones that were positive for β-galactosidase activity (Table 1). Table 1 shows the data from these experiments, where cell colonies were stained in situ for β-galactosidase activity and scored for activity. Cells were scored positive if the colonies turned blue in the presence of X-gal substrate and scored negative if colonies remained white. Analysis of triplicate experiments showed a significant increase in the number of β-galactosidase positive cells in the 293PMS134 cultures, while no β-galactosidase cells were seen in the control 293vec cells.

TABLE 1

Number of 293PMS134 and 293vec cells containing functional β-galactosidase gene as a result of MMR deficiency.

| Cells | White Colonies | Blue Colonies | % Clones with altered β-gal |
|---|---|---|---|
| 293vec | 95 ± 17 | 0 | 0/95 = 0% |
| 293PMS134 | 88 ± 13 | 44 ± 8 | 44/132 = 33% |

Table 1. β-galactosidase expression of 293vec and 293PMS134134 cells transfected with pCAR-OF reporter vectors. Cells were transfected with the pCAR-OF β-galactosidase reporter plasmid. Transfected cells were selected in hygromycin and G418, expanded and stained with X-gal solution to measure for β-galactosidase activity (blue colored cells). 3 plates each were analyzed by microscopy. The results below represent the mean +/− standard deviation of these experiments.

293PMS134/pCAR-OF clones that were pooled and expanded also showed a number of cells that contained a functional β-galactosidase gene. No β-galactosidase positive cells were observed in 293vec cells transfected with the pCAR-OF vector (data not shown). These data demonstrate the ability of dominant negative alleles of MMR genes to suppress endogenous MMR activity. These cells are now primed for the introduction of locus specific targeting fragments for altering the expression or tagging the exon of specific genes within the chromosomal context of the host.

In situ X-Gal Staining

For in situ analysis, 100,000 cells are harvested and fixed in 1% gluteraldehyde, washed in phosphate buffered saline solution and incubated in 1 ml of X-gal substrate solution (0.15 M NaCl, 1 mM $MgCl_2$, 3.3 mM $K_4Fe(CN)_6$, 3.3 mM $K_3Fe(CN)_6$, 0.2% X-Gal ) in 24 well plates for 2 hours at 37°

C. Reactions are stopped in 500 mM sodium bicarbonate solution and transferred to microscope slides for analysis. Three plates each are counted for blue (β-galactosidase positive cells) or white (β-galactosidase negative cells) to assess for MMR inactivation. Table 1 shows the results from these studies.

TABLE 1

Number of 293PMS134 and 293vec cells containing functional β-galactosidase gene as a result of MMR deficiency.

| Cells | White Colonies | Blue Colonies | % Clones with altered β-gal |
|---|---|---|---|
| 293vec | 95 +/− 17 | 0 | 0/95 = 0% |
| 293PMS134 | 88 +/− 13 | 44 +/− 8 | 44/132 = 33% |

Example 2

Generation of Targeting Cassettes for Altered Gene Expression or Tagged Exons for Expression Profiling of Host Organisms.

It has been previously reported that MMR defective cells have a higher rate of homologous recombination due to the decreased stringency for identical basepair matches of the target vector to the chromosomal locus. We observed the ability to generate an increased rate of homologous recombination of fragments containing very short regions of homology in MMR defective cells obtained from colorectal cancer patents, such as the HCT116 cell line (N. Nicolaides personal observation), while homologous recombination in cells that were MMR proficient had undetectable integration of this type of fragment into a targeted locus such as the wild type HEK293 cell line.

To address the ability to use LSTFs containing short areas of homology for rapid genome targeting of chromosomal loci, we employed the use of MMR defective 293 cells (293PMS134) that express the PMS134 dominant negative allele as described in Example 1. We then employed a LSTF that containing the Cytomegalovirus (CMV) promoter downstream of a constitutively expressed hygromycin cassette to monitor integration in the MMR defective line (see FIG. 1).

Generation of Promoter Locus-specific Targeting Fragments and Cell Lines.

PCR products were amplified from the p$^4$ plasmid, which contains a DNA insert with the Thymidine Kinase (Tk) promoter upstream of the hygromycin resistance (Hyg) gene followed by the SV40 polyadenylation signal and the cytomegalovirus (CMV) promoter. Plasmid was amplified with primers containing 3' sequences that are homologous to the plasmid vector sequence region upstream of the Tk promoter and downstream of the CMV promoter. Each primer also contained 70 nt that were homologous to the genomic locus of various target genes at the start site of transcription. PCRs were typically carried out using buffers as previously described (Grasso, L. et al. (1998) "Molecular analysis of human interleukin-9 receptor transcripts in peripheral blood mononuclear cells. Identification of a splice variant encoding for a nonfunctional cell surface receptor" J. Biol. Chem. 273: 24016-24024). Amplification conditions consisted of one cycle of 95° C. for 5minutes, 30 cycles of 94° C. for 30 seconds/47° C. for 30 seconds/72° C. for 1 minute, and one cycle of 72° C. for 2 minutes. Primers pairs used for each gene are indicated in Table 2. LSTFs were analyzed by gel electrophoresis to ensure molecular weight. Products were then purified by spin column to remove primers, salts and unincorporated dNTPs from fragments.

The generation of stable cell lines with promoter locus-specific targeted knock-in fragments was performed as follows. Briefly, 1×10$^5$ HEK293 (human embryonic kidney) cells stably expressing the PMS134 gene (see Example 1) were transfected with 1 µg of purified PCR products from above using 3 µl Fugene6 (Invitrogen) and stable transfectant pools were generated by co-selection with 100 µg/ml hygromycin B and G418 (neomycin). Cultures were selected for 14 days in neomycin and hygromycin. Pools and clones were analyzed for locus specific integration using reverse transcriptase coupled PCR as described (Nicolaides, N. C. et al. (1997) "Interleukin 9: a candidate gene for asthma" Proc. Natl. Acad. Sci. USA 94:13175-13180). Briefly, 1×10$^5$ hygromycin/neomycin resistant cells transfected with various PCR fragments were lysed in 50 µl lysis buffer containing tris-edta and NP40 and incubated for 10 minutes on ice. Samples were added to oligo d(T) tubes in the presence of 50 µl binding buffer and incubated 15' at RT with shaking. Lysates were aspirated and washed 2× each with high salt wash buffer followed by low salt wash buffer. 33 µls 1× First-strand cDNA mix containing NTPs and reverse transcriptase was added to tubes and incubated 1 hr at 37° C. 67 µl of a dH$_2$O/TAQ mixture was aliquoted into each sample along with appropriate gene-specific primers from Table 2. Amplification conditions consisted of one cycle of 95° C. for 5 minutes, 30 cycles of 94° C. for 30 seconds/47° C for 30 seconds/72° C. for 1 minute, and one cycle of 72° C. for 2 minutes.

Figure 2:
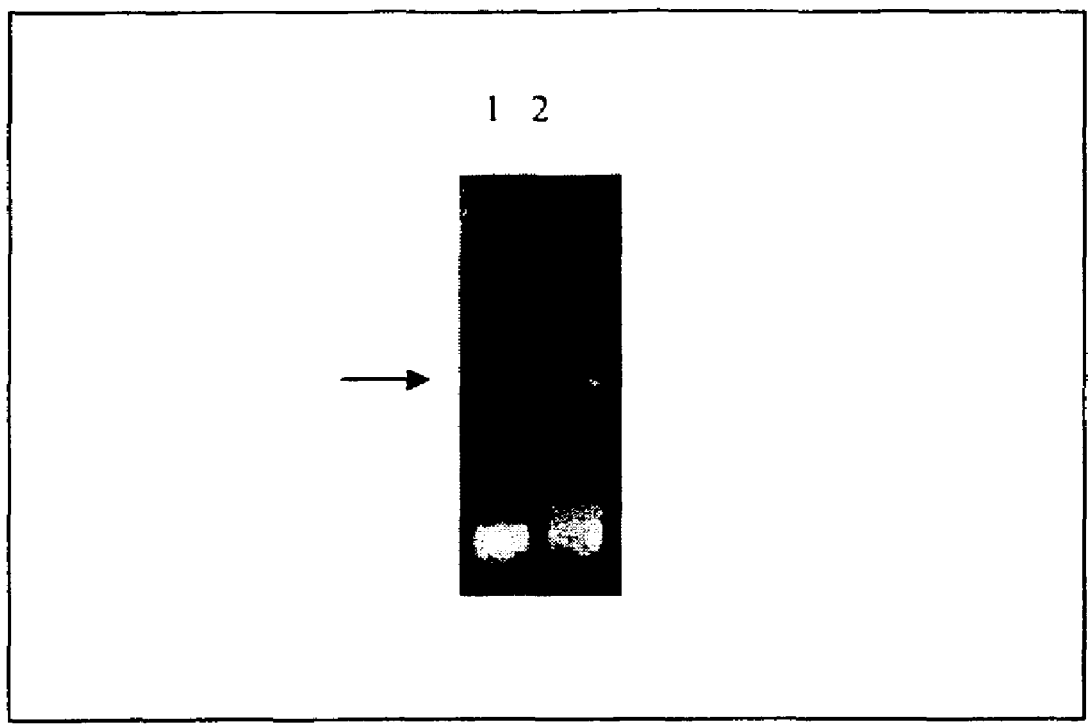
FIG. 2 shows expression of β-globin in HEK293 cells transfected with LSTFs. RT-PCR analysis of RNA extracted from 293PMS134 cells transfected with mock LSTF or Hyg-CMV β-globin LSTF. Reverse transcriptase PCR was carried out using equal amounts of total RNA from each cell line and a 5' primer located in the leader sequence downstream of the CMV promoter (SEQ ID NO:21) and a 3' primer located in the coding region of the beta-globin gene (SEQ ID NO:25). PCR reactions were electrophoresed on 2% agarose gels, ethidium bromide stained and visualized using a UV light box. The arrow indicates a product of the expected molecular weight.

Analysis of site-specific integration was carried out using four different previously studied loci that are expressed at undetectable levels in the HEK293 cell line and growth conditions used in these studies. The target genes were the human N-Ras (a signal transduction gene), beta-globin (a structural protein), INF-gamma (a secreted growth factor), and galanin receptor (a seven transmembrane G-coupled receptor). The primers used for each 5' flanking locus is given below in Table 2 where the last 30 nts of each primer is specific for the 5' and 3' ends of the targeting fragment containing the Tk promoter driving hygromycin expression followed by the CMV promoter, while the 5' ends of each primer pair are specific to the 5' flanking region of each locus, N-RAS (SEQ ID NO: 13 and 14); beta-globin (SEQ ID NO: 15 and 16); Interferon gamma (SEQ ID NO: 17 and 18); and galanin receptor (SEQ ID NO: 19 and 20). Transfected cells were first analyzed by RT-PCR analysis to identify increased steady-state gene expression using primer pairs that were capable of detecting spliced mRNA (primers listed in Table 3). These primer combinations can detect the endogenous gene expression of a target gene independent of LSTF integration. Expression analysis of transfected cells failed to reveal robust expression levels of any of these four loci in parental HEK293 or control HEK293 cells transfected with the different fragments. Conversely, robust expression was observed for all targeted loci in transfected 293PMS134 cells containing the appropriate LSTF. A representative example is shown using cells where the beta-globin locus was targeted. HEK293 cells, which are derived from embryonic kidney have not been found to express the erythroid-specific beta-globin. Shown in FIG. 2 is expression analysis of beta-globin using cDNA specific primers (SEQ ID NO:24 and SEQ ID NO:25, Table 3) in targeted cells containing the beta-globin LSTF, while none was observed in cells transfected with targeting vectors to other loci, which served as negative controls. An independent RT-PCR was carried using cDNA from the positive cultures using a 5' primer that was located in the distal leader sequence of he CMV promoter (SEQ ID NO: 21, Table 3) and a 3' primer located within the coding region of the beta-globin gene (SEQ ID NO: 25, Table 3). This primer set is only capable of producing a product with an expected molecular weight if the LSTF is integrated within the specific targeted locus because the resultant product consists of a hybrid transcript consisting of a cDNA comprised of a CMV leader fused to the initiating start codon for the targeted gene, which can only occur by correct genome integration for formation of this hybrid message. Similar results were found using targeting fragments to other chromosomal loci as well as using primers containing 50 nts of flanking sequence, whereas no locus specific expression was observed in HEK293 control cells transfected with similar fragments (data not shown).

Analysis of cell lines transfected with promoter-specific LSTFs can be carried out by any number of methods that measure levels of RNA or proteins. Such methods of analysis may include but are not limited to microarray analysis, in situ RT-PCR, Northern blot, western blotting, immunostaining, fluorescent Activated Cell Sorting, etc. Cell lines over expressing a gene of interest may be analyzed by functional assays using biological systems that are sensitive to the production of certain biochemicals of growth factors. These methods are routinely used by those skilled in the art of high throughput screening and are useful for analyzing the expression levels of target genes in cells transfected with LSTFs.

Generation of Exon Locus-specific Targeting Fragments and Cell Lines.

The ability to target an exon of a specific gene in any given host organism enables the generation of exon specific tags to monitor gene expression profiles of a target gene upon exposure to biological factors and/or pharmaceutical compounds.

TABLE 2

Transfection construct primers.

| Gene | 5' primer name | 5' primer sequence | 3' primer name | 3' primer sequence |
| --- | --- | --- | --- | --- |
| N-Ras | NRAS-564674 (SEQ ID NO:13) | TTCAGAGTAGAAAACTAAATATGAT GAATAACTAAAAATAATTTCTCAAA TTTTTTCTGATGGTTCCTTCGCTTC ATCCCCGTGGCCCGTTGCTCGCG | NRAS-567492R (SEQ ID NO:14) | GCCCCAGTTGGACCCTG AGGTCGTACTCACCCCA ACAGCTCAGCGCCCCCT CTCCAGCGCCGCCATAA GCTACCCAGCTTCTAGA GATCTGACGGTTCAC |
| β-globin | HBB-59479 (SEQ ID NO:15) | TGTGTGTGTGTTGTGGTCAGTGGGG CTGGAATAAAAGTAGAATAGACCTG CACCTGCTGTGGCATCCATTCTGCTT CATCCCCGTGGCCCGTTGCTCGCG | HBB-62206R (SEQ ID NO:16) | TCAGGAGTCAGGTGCAC CATGGTGTCTGTTTGAGG TTGCTAGTGAACACAGT TGTGTCAGAAGCAAATG TTACCCAGCTTCTAGAG ATCTGACGGTTCAC |
| INF-γ | IFNG-1626972 (SEQ ID NO:17) | GTTCTCTGGACGTAATTTTTCTTGAG CAGAGCAACAGTAGAGCTTTGTATG CAACAATGTAATTTTTACACTGCTTC ATCCCCGTGGCCCGTTGCTCGCG | IFNG-1629791R (SEQ ID NO:18) | ATCAGGTCCAAAGGACT TAACTGATCTTTCTCTTC TAATAGCTGATCTTCAG ATGATCAGAACAATGTG CTACCCAGCTTCTAGAG ATCTGACGGTTCAC |
| GalaninI Receptor | GalR-283026F (SEQ ID NO:19) | TGGCAGGAGCGGAAGCAAGAGAGG GAAGGGAGGAGGTGCCACACACTTT CAAACAACCAGATCTTCAGACCTGC TTCATCCCCGTGGCCCGTTGCTCGCG | GalR-280208R (SEQ ID NO:20) | GCTCGGCTGAAATCCGC GCCCCTTAGAAGTCACG GTGCGCGAGCAGAGACT GGACGGATTCTAGCGGG ATTACCCAGCTTCTAGA GATCTGACGGTTCAC |

TABLE 3

RT-PCR primers.

| 5' primer name | 5' primer sequence | 3' primer name | 3' primer sequence |
| --- | --- | --- | --- |
| (SEQ ID NO:21) | CAGATCTCTAGAAGCTGGGT | | |
| Nras (SEQ ID NO:22) | ATGACTGAGTACAAACTGGTGGTGG | Nras-R (SEQ ID NO:23) | CATTCGGTACTGGCGTATTTCTC |
| Globin (SEQ ID NO:24) | ATGGTGCACCTGACTCCTGAGGAG | Globin (SEQ ID NO:25) | GTTGGACTTAGGGAACAAAGGA AC |
| Glanin (SEQ ID NO:26) | ATGCTGGTGAGCATCTTCACCCTG | Glanin (SEQ ID NO:27) | CTGAAGAGGAAGGAAGCCGGCG TC |
| IFNg (SEQ ID NO:28) | ATGAAATATACAAGTTATATCTTGGC | IFNg (SEQ ID NO:29) | CAGGACAACCATTACTGGGATGC |

This application teaches the use of inhibitors of MMR in somatic cells that can enhance the recombination of fragments with as little as 50 nts of homologous sequence to a chromosomal target within complex genomes including those derived of human materials (see above). To take advantage of the ability to generate locus specific targets, we teach of the use of a exon locus specific targeting (LST) vectors that can be used to generate knock-ins within an exon of a specific locus, whereby the LST fragment contains a selectable marker fused to a reporter gene that can be used in combination with any number of analytical systems to monitor gene expression in situ or in vitro. An example of one such fusion cassette is presented in FIG. 3, whereby the hygromycin resistance gene is fused in-frame with the luciferase gene. Using a similar strategy as described above, we generated a number of fusion expression cassettes that contain a selectable maker fused in-frame with a reporter gene. These vectors can consist of any selectable marker that can be used to select for stable transformants and any reporter gene that can be monitored to analyze expression levels of particular locus or loci.

Figure 4:
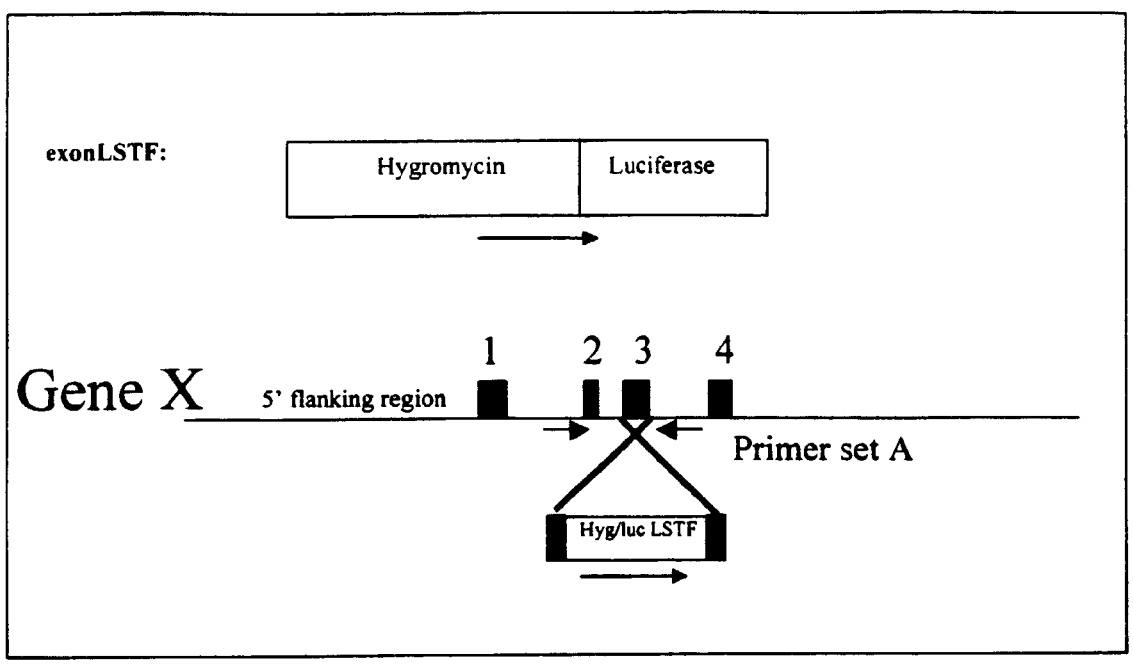
FIG. 4 shows a schematic diagram of exon locus-specific targeting fragments (LSTF) and the genomic organization of a target gene. The LSTF contains a selectable marker gene (i.e., hygromycin, neomycin, zeocin, etc.) that is in frame with a reporter gene, (i.e., luciferase, Green Fluorescent Protein, etc.). Primer Set A indicates the primer position of oligonucleotides used to analyze each target gene to confirm locus specific integration where the 5' primer is located in the exon preceding the targeted exon and the 3' primer is located proximal to the site of integration. The box below each gene represents the LSTF, where the shaded areas represent the areas of homology to the target gene, whereby the homologous region is 50-70 nts in length. The black boxes in the gene diagrams represent exons whereby RT-PCR can be used to assay for fusion of spliced cDNAs consisting of the selectable marker-reporter cDNA within the targeted gene's encoded transcript.

Exon LSTFs is generated by PCR using 80-100 nt primers that contain 50-70 nts of 5' sequence that are homologous to the 5' and 3' boarders of a given gene's exon, while the terminal 30nts are specific for the first and last codons of the fusion protein, such as those given as examples in FIG. 3. PCR products are amplified from the pFusion plasmid, containing a DNA insert with the selectable marker/reporter gene. PCRs are carried out using buffers as previously described (Grasso, L. et al. (1998) "Molecular analysis of human interleukin-9 receptor transcripts in peripheral blood mononuclear cells. Identification of a splice variant encoding for a nonfunctional cell surface receptor" *J. Biol. Chem.* 273: 24016-24024). Amplification conditions consisted of one cycle of 95C for 5', 30 cycles of 94° C. for 30 seconds/47° C. for 30 seconds/72° C. for 1 minute, and one cycle of 72° C. for 2 minutes. Primers pairs used for each exon LSTF are indicated in Table 4. LST fragments are analyzed by gel electrophoresis to ensure correct size. Reactions with correct size are then purified by spin column to remove primers from fragments Generation of stable cell lines with exon locus-specific targeted knock-in fragments are performed as follows. Briefly, $1 \times 10^5$ MMR defective cells (stably expressing the PMS134 gene (see Example 1) are transfected with 1 µg of purified PCR products from above using 3 µl Fugene 6 (Invitrogen) and stable transfectant pools are generated by co-selection with 100 µg/ml hygromycin B and G418 (neomycin). Cultures are selected for 14 days in neomycin and hygromycin. Pools and clones are analyzed for locus specific integration using reverse transcriptase coupled PCR as described (Nicolaides, N. C. et al. (1997) "Interleukin 9: a candidate gene for asthma" *Proc. Natl. Acad. Sci. USA* 94:13175-13180). Briefly, $1 \times 10^5$ hygromycin/neomycin resistant cells transfected with various PCR fragments are lysed in 50 µl lysis buffer containing tris-edta and NP40 and incubated 10 minutes on ice. Samples are added to oligo d(T) tubes in the presence of 50 µl binding buffer and incubated 15' at RT with shaking. Lysates are aspirated and washed 2× each with high salt wash buffer followed by low salt wash buffer. 33 µls 1× First-strand cDNA mix containing NTPs and reverse transcriptase is added to tubes and incubated 1 hr at 37° C. 67 µl of a dH$_2$0/TAQ mixture was aliquoted into each sample along with appropriate gene-specific primers that target sequences contained within the proceeding exon and a 3' primer that targets sequence proximal to the fusion integration site. A schematic description of the exon LSTF and PCR analysis for integration are shown in FIG. 4.

TABLE 4

Primers for exon locus specific targeting fragments. The $N_{(50-70)}$ indicates sequence to be added to each primer for a specific exon.

| Fusion LSTF | 5' primer | | 3' primer | |
|---|---|---|---|---|
| Hyg-GFP | 5'-N$_{(50-70)}$-atgaaaaagc ctgaactcaccgcgacgtct-3' | (SEQ ID NO:30) | 5'-N$_{(50-70)}$- tttatataattcatccata ccatgtgtgtg-3' | (SEQ ID NO:31) |
| Hyg-Luc | 5'-N$_{(50-70)}$-atgaaaaagc ctgaactcaccgcgacgtct-3' | (SEQ ID NO:32) | 5'-N$_{(50-70)}$-caatttggactttccg cccttcttggcctt-3' | (SEQ ID NO:33) |

Example 3

Generation of Targeting Cassettes for Altered Gene Expression or Tagged Chromosomes for Site-specific Gene Amplification.

Another means for enhancing gene expression from the genome of a host organism is through the process of gene amplification. A number of studies have reported the use of expression vectors consisting of a gene of interest linked to a DHFR expression cassette. Once the expression vector has been inserted into the genome of a host cell line, expression cassettes can be amplified by selecting for clonal resistance to methotrexate, a process that occurs through gene amplification of the DHFR gene and surrounding proximal and distal loci (Ma, C. et al. (1993) "Sister chromatid fusion initiates amplification of the dihydrofolate reductase gene in Chinese hamster cells" *Genes Dev.* 7:605-620). A method is taught here that employs the use of LSTFs in MMR defective cells via the use of MMR inhibitors, whereby the LSTF contains a constitutively expressed DHFR gene juxtaposed to selectable markers with the ends of the LSTF containing 50-70 bps of homologous sequence to an endogenous gene locus. The target site may be proximal, intragenic or distal to the target locus. Briefly, the LSTF is generated from a Hyg-DHFR cassette via PCR using the pHYG-DHFR vector as template. Amplifications are generated using primers that are 5' to the TK promoter, which controls the HYG expression and a primer that is directed to the sequence 3' of the DHFR gene, which consists of the SV40polyA signal. Each primer contains 50-70 nts that are homologous to the chromosomal target site. Cells are transfected with a dominant negative MMR expression vector, which contains a neomycin resistance marker as described in Example 1 along with the LSTF.

Upon cotransfection, cells are coselected in hygromycin and neomycin for 14 days. Cells are analyzed for chromosomal specific integration using primers that flank the targeted site of integration. Analysis can be in pooled cultures or in single clones. Upon confirmation of integration, cells are selected for chromosomal site-specific amplification by methotrexate (MTX) selection. Briefly, $1.0 \times 10^6$ cells are seeded in 10cm culture dishes with complete growth medium supplemented with 10% dialyzed fetal bovine serum 24 h prior to drug selection. Next, MTX is added at 15 times the calculated $IC_{50}$ and the plates are incubated at 37° C. Cells are grown in the presence of continuous MTX selection for 14 to 21 days. Colonies are selected and analyzed for DHFR and chromosome amplification. Analysis of genomic DNA is carried out using the modified salting out method. Briefly, cells are isolated from parental or MTX exposed clones. Cells are pelleted and lysed in 1 ml of lysis buffer (25 mM Tris-HCl pH 8.0, 25 mM EDTA, 1% SDS, 0.5 mg/ml proteinase K). Cell lysates are incubated at 50° C. 12 hrs to overnight. Following ethanol precipitation and resuspension, RNaseA was added to 100 μg/ml and the mixture was kept at 37° C. for 30 min. Next, DNAs are phenol extracted and precipitated by the addition of 3 M NaOAc and ethanol. DNA pellets are washed once with 70% ethanol, air-dried and resuspended in TE buffer. DNAs are digested with different restriction enzymes and probed for DHFR and the locus of interest for amplification as compared to the control cells. MMR activity is restored in amplified clones and the cells are used for experimentation or production.

A benefit taught by this application is the combined use of MMR deficiency, enhanced homologous recombination with LSTFs and the ability to produce site-specific gene amplification within a host's genomic locus. Recently, a report by Lin, C. T. et al. ((2001) "Suppression of gene amplification and chromosomal DNA integration by the DNA mismatch repair system" *Nucl. Acid Res.* 29:3304-3310) found the lack of MMR results in increased gene amplification using a reporter gene system. The approach taught here describes a method that allows for enhanced locus amplification within a specific chromosomal site a hosts genome.

Discussion

The results and observation described here lead to several conclusions. First, expression of PMS134 results in an increase in microsatellite instability in HEK293 through the dominant negative blockage in mismatch repair. Second, that the inhibition of MMR in somatic cells can lead to increased rates of homologous recombination between short nucleotide sequences 50-70 nts in length. Finally, the combination of blocking MMR with dominant negative inhibitors such as polypeptides or chemical inhibitors can lead to a rapid process that can be used to genetically engineer somatic mammalian cells to alter the expression of a particular locus at the chromosomal level as well as tag exons of genes whereby the expression of a chromosomal locus can be monitored in response to biochemicals and pharmaceutical compound exposure.

While previous reports have taught the use of inhibiting MMR can lead to increased homologous recombination w ith divergent sequences, this application teaches t he use of employing MMR deficient somatic cell lines along with targeting fragments containing 50-70 nts of homology to a gene locus to alter and/or monitor its expression.

The blockade of MMR in cells to increase LSTF integration can be through the use of dominant negative MMR gene alleles from any species including bacteria, yeast, protozoa, insects, rodents, primates, mammalian cells, and man. Blockade of MMR can also be generated through the use of antisense RNA or deoxynucleotides directed to any of the genes involved in the MMR biochemical pathway. Blockade of MMR can be through the use of polypeptides that interfere with subunits of the MMR complex including but not limited to antibodies. Finally, the blockade of MMR may be through the use of chemicals such as but not limited tononhydrolyzable ATP analogs, which have been shown to block MMR (Galio, L. et al. (1999) "ATP hydrolysis-dependent formation of a dynamic ternary nucleoprotein complex with MutS and MutL" *Nucl. Acids Res.* 27:2325-2331; Spampinato, C. and P. Modrich (2000) "The MutL ATPase is required for mismatch repair" *J. Biol. Chem.* 275:9863-9869.

What is claimed is:

1. A method of introducing a locus specific targeting fragment into the genome of a cell in vitro through homologous recombination comprising:
inhibiting endogenous mismatch repair in cells of a cell population by introducing into said cells a polynucleotide comprising a dominant negative form of the human PMS2 gene, wherein the dominant negative form of said human PMS2 gene is PMS2-134, PMSR2, or PMSR3 and wherein said polynucleotide is expressed, thereby generating mismatch repair-inhibited cells;
contacting said mismatch repair-inhibited cells with a locus specific targeting fragment, wherein said locus specific targeting fragment is a polynucleotide comprising at least one promoter, a sequence encoding a selectable marker, and 5' and 3' flanking regions of about 20 to about 120 nucleotides; wherein said 5' and 3' flanking regions are homologous to a selected portion of the genome of said cells; and wherein said locus specific targeting fragment integrates into the genome of said cells by homologous recombination; and
selecting a cell comprising said locus specific targeting fragment.

2. The method of claim 1, further comprising restoring mismatch repair activity of said cell comprising said locus specific targeting fragment.

3. The method of claim 1, wherein said promoter is selected from the group consisting of a CMV promoter, an SV40 promoter, elongation factor promoter, LTR sequence, a pIND promoter sequence, a tetracycline promoter sequence, and a MMTV promoter sequence.

4. The method of claim 1, wherein said selectable marker is selected from the group consisting of a hygromycin resistance gene, a neomycin resistance gene and a zeocin resistance gene.

5. The method of claim 1, wherein said 5' and 3' flanking regions are about 30 to about 100 nucleotides in length.

6. The method of claim 1, wherein said 5' and 3' flanking regions are about 40 to about 90 nucleotides in length.

7. The method of claim 1, wherein said 5' and 3' flanking regions are about 50 to about 80 nucleotides in length.

8. The method of claim 1, wherein said 5' and 3' flanking regions are about 50 to about 70 nucleotides in length.

9. The method of claim 1, wherein said cell population comprises vertebrate cells, invertebrate cells, mammalian cells, reptilian cells, fungal cells, or yeast cells.

10. The method of claim 1, wherein said 5' and 3' flanking regions are homologous to a 5' flanking region of a selected chromosomal locus of said cell comprising said locus specific targeting fragment.

11. The method of claim 1 wherein said locus specific targeting fragment comprises a second protein-encoding sequence operatively linked to a second promoter.

12. The method of claim 11 wherein said second protein-encoding sequence is a dihydrofolate reductase sequence.

13. The method of claim 1 wherein said cells are somatic cells.

14. A method of genetically altering a cell to overproduce a selected polypeptide in vitro comprising:
inhibiting endogenous mismatch repair of cells of a cell population by introducing into said cells a polynucleotide comprising a dominant negative form of the human PMS2 gene, wherein the dominant negative form of said human PMS2 gene is PMS2-134, PMSR2, or PMSR3 and wherein said polynucleotide is expressed, thereby generating mismatch repair-inhibited cells;

introducing a locus specific targeting fragment into said mismatch repair-inhibited cells, wherein said locus specific targeting fragment is a polynucleotide comprising at least one promoter sequence, a sequence encoding a selectable marker, a sequence encoding the selected polypeptide, and 5' and 3' flanking regions of about 20 to about 120 nucleotides, wherein said 5' and 3' flanking regions are homologous to a selected portion of the genome of said cell, and wherein said locus specific targeting fragment integrates into the genome of said cell by homologous recombination; and selecting a cell that overproduces said selected polypeptide.

15. The method of claim 14, further comprising restoring mismatch repair activity of said cell.

16. The method of claim 14, wherein said promoter is selected from the group consisting of a CMV promoter, an SV40 promoter, elongation factor promoter, LTR sequence, a pIND promoter sequence, a tetracycline promoter sequence, and a MMTV promoter sequence.

17. The method of claim 14, wherein said selectable marker is selected from the group consisting of a hygromycin resistance gene, a neomycin resistance gene and a zeocin resistance gene.

18. The method of claim 14, wherein said 5' and 3' flanking regions are about 30 to about 100 nucleotides in length.

19. The method of claim 14, wherein said 5' and 3' flanking regions are about 40 to about 90 nucleotides in length.

20. The method of claim 14, wherein said 5' and 3' flanking regions are about 50 to about 80 nucleotides in length.

21. The method of claim 14, wherein said 5' and 3' flanking regions are 50 to 70 nucleotides in length.

22. The method of claim 14, wherein said cell population comprises vertebrate cells, invertebrate cells, mammalian cells, reptilian cells, fungal cells, or yeast cells.

23. The method of claim 14 wherein said cells are somatic cells.

24. A method of introducing a locus specific targeting fragment into the genome of a cell in vitro through homologous recombination comprising:

inhibiting endogenous mismatch repair in cells of a cell population by contacting said cells with a chemical inhibitor of mismatch repair, wherein said chemical inhibitor of mismatch repair is an anthracene, wherein said anthracene has the formula:

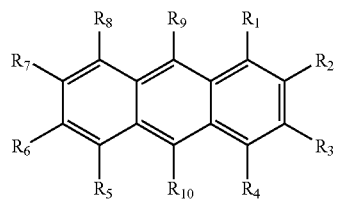

wherein $R_1$-$R_{10}$ are independently hydrogen, hydroxyl, amino group, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroaryl and substituted heteroaryl contain at least one heteroatom that is oxygen, sulfur, a metal atom, phosphorus, silicon or nitrogen; and wherein the substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkyloxy, guanidino, alkoxycarbonyl, alkoxy, hydroxy, carboxy or amino group; and wherein said amino group is optionally substituted with an acyl group, or 1 to 3 aryl or lower alkyl groups; or wherein any two of $R_1$-$R_{10}$ can together form a polyether; or wherein any two of $R_1$-$R_{10}$ can, together with intervening carbon atoms of the anthracene, form a crown ether, thereby generating mismatch repair-inhibited cells;

contacting said mismatch repair-inhibited cells with a locus specific targeting fragment, wherein said locus specific targeting fragment is a polynucleotide comprising at least one promoter, a sequence encoding a selectable marker, and 5' and 3' flanking regions of about 20 to about 120 nucleotides; wherein said 5' and 3' flanking regions are homologous to a selected portion of the genome of said cells; and wherein said locus specific targeting fragment integrates into the genome of said cells by homologous recombination; and selecting a cell comprising said locus specific targeting fragment.

25. The method of claim 24, further comprising restoring mismatch repair activity of said cell comprising said locus specific targeting fragment.

26. The method of claim 24, wherein said promoter is selected from the group consisting of a CMV promoter, an SV40 promoter, elongation factor promoter, LTR sequence, a pIND promoter sequence, a tetracycline promoter sequence, and a MMTV promoter sequence.

27. The method of claim 24, wherein said selectable marker is selected from the group consisting of a hygromycin resistance gene, a neomycin resistance gene and a zeocin resistance gene.

28. The method of claim 24, wherein said 5' and 3' flanking regions are about 30 to about 100 nucleotides in length.

29. The method of claim 24, wherein said 5' and 3' flanking regions are about 40 to about 90 nucleotides in length.

30. The method of claim 24, wherein said 5' and 3' flanking regions are about 50 to about 80 nucleotides in length.

31. The method of claim 24, wherein said 5' and 3' flanking regions are about 50 to about 70 nucleotides in length.

32. The method of claim 24, wherein said cell population comprises vertebrate cells, invertebrate cells, mammalian cells, reptilian cells, fungal cells, or yeast cells.

33. The method of claim 24, wherein said 5' and 3' flanking regions are homologous to a 5' flanking region of a selected chromosomal locus of said cell comprising said locus specific targeting fragment.

34. The method of claim 24 wherein said locus specific targeting fragment comprises a second protein-encoding sequence operatively linked to a second promoter.

35. The method of claim 34 wherein said second protein-encoding sequence is a dihydrofolate reductase sequence.

36. The method of claim 24 wherein said cells are somatic cells.

37. A method of genetically altering a cell to overproduce a selected polypeptide in vitro comprising:

inhibiting endogenous mismatch repair of cells of a cell population by contacting said cells with a chemical inhibitor of mismatch repair, wherein said chemical inhibitor of mismatch repair is an anthracene, wherein said anthracene has the formula:

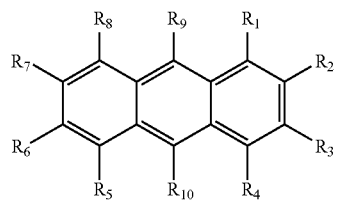

wherein $R_1$-$R_{10}$ are independently hydrogen, hydroxyl, amino group, alkyl, substituted alkyl, alkenyl, substituted alkenyl, alkynyl, substituted alkynyl, O-alkyl, S-alkyl, N-alkyl, O-alkenyl, S-alkenyl, N-alkenyl, O-alkynyl, S-alkynyl, N-alkynyl, aryl, substituted aryl, aryloxy, substituted aryloxy, heteroaryl, substituted heteroaryl, aralkyloxy, arylalkyl, alkylaryl, alkylaryloxy, arylsulfonyl, alkylsulfonyl, alkoxycarbonyl, aryloxycarbonyl, guanidino, carboxy, an alcohol, an amino acid, sulfonate, alkyl sulfonate, CN, $NO_2$, an aldehyde group, an ester, an ether, a crown ether, a ketone, an organosulfur compound, an organometallic group, a carboxylic acid, an organosilicon or a carbohydrate that optionally contains one or more alkylated hydroxyl groups;

wherein said heteroaryl and substituted heteroaryl contain at least one heteroatom that is oxygen, sulfur, a metal atom, phosphorus, silicon or nitrogen; and wherein the substituents of said substituted alkyl, substituted alkenyl, substituted alkynyl, substituted aryl, and substituted heteroaryl are halogen, CN, $NO_2$, lower alkyl, aryl, heteroaryl, aralkyl, aralkyloxy, guanidino, alkoxycarbonyl, alkoxy, hydroxy, carboxy or amino group; and wherein said amino group is optionally substituted with an acyl group, or 1 to 3 aryl or lower alkyl groups; or wherein any two of $R_1$-$R_{10}$ can together form a polyether; or wherein any two of $R_1$-$R_{10}$ can, together with intervening carbon atoms of the anthracene, form a crown ether, thereby generating mismatch repair-inhibited cells;

introducing a locus specific targeting fragment into said mismatch repair-inhibited cells, wherein said locus specific targeting fragment is a polynucleotide comprising at least one promoter sequence, a sequence encoding a selectable marker, a sequence encoding the selected polypeptide, and 5' and 3' flanking regions of about 20 to about 120 nucleotides, wherein said 5' and 3' flanking regions are homologous to a selected portion of the genome of said cell, and wherein said locus specific targeting fragment integrates into the genome of said cell by homologous recombination; and selecting a cell that overproduces said selected polypeptide.

38. The method of claim 37, further comprising restoring mismatch repair activity of said cell.

39. The method of claim 37, wherein said promoter is selected from the group consisting of a CMV promoter, an SV40 promoter, elongation factor promoter, LTR sequence, a pIND promoter sequence, a tetracycline promoter sequence, and a MMTV promoter sequence.

40. The method of claim 37, wherein said selectable marker is selected from the group consisting of a hygromycin resistance gene, a neomycin resistance gene and a zeocin resistance gene.

41. The method of claim 37, wherein said 5' and 3' flanking regions are about 30 to about 100 nucleotides in length.

42. The method of claim 37, wherein said 5' and 3' flanking regions are about 40 to about 90 nucleotides in length.

43. The method of claim 37, wherein said 5' and 3' flanking regions are about 50 to about 80 nucleotides in length.

44. The method of claim 37, wherein said 5' and 3' flanking regions are 50 to 70 nucleotides in length.

45. The method of claim 37, wherein said cell population comprises vertebrate cells, invertebrate cells, mammalian cells, reptilian cells, fungal cells, or yeast cells.

46. The method of claim 37 wherein said cells are somatic cells.

* * * * *